US007273726B2

(12) United States Patent
Fong et al.

(10) Patent No.: US 7,273,726 B2
(45) Date of Patent: Sep. 25, 2007

(54) COMPOUNDS, COMPOSITIONS AND METHODS FOR THE TREATMENT OF DISEASES CHARACTERIZED BY A-33 RELATED ANTIGENS

(75) Inventors: Sherman Fong, Alameda, CA (US); Audrey Goddard, San Francisco, CA (US); Austin L. Gurney, Belmont, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 219 days.

(21) Appl. No.: 10/785,221

(22) Filed: Feb. 24, 2004

(65) Prior Publication Data

US 2004/0141971 A1 Jul. 22, 2004

Related U.S. Application Data

(60) Division of application No. 09/953,499, filed on Sep. 14, 2001, now Pat. No. 6,838,554, which is a continuation of application No. 09/254,465, filed on Mar. 5, 1999, now Pat. No. 6,410,708, which is a continuation of application No. PCT/US98/24855, filed on Nov. 20, 1998, and a continuation-in-part of application No. PCT/US98/19437, filed on Sep. 17, 1998.

(60) Provisional application No. 60/066,364, filed on Nov. 21, 1997.

(51) Int. Cl.
C07H 21/04 (2006.01)
C12P 21/06 (2006.01)
C12N 1/20 (2006.01)
C12N 15/74 (2006.01)

(52) U.S. Cl. ............... 435/69.1; 435/252.3; 435/320.1; 536/23.1

(58) Field of Classification Search ............... 536/23.1; 435/69.1, 252.3, 320.1
See application file for complete search history.

(56) References Cited

U.S. PATENT DOCUMENTS

| | | | |
|---|---|---|---|
| 4,579,827 A | 4/1986 | Sakamoto et al. | |
| 5,650,295 A | 7/1997 | Li et al. | |
| 6,022,708 A | 2/2000 | de Sauvage et al. | |
| 6,410,708 B1 | 6/2002 | Ashkenazi et al. | |

FOREIGN PATENT DOCUMENTS

| | | |
|---|---|---|
| EP | 199141 | 10/1986 |
| EP | 317050 | 5/1989 |
| WO | WO90/05537 | 5/1990 |
| WO | WO96/34943 | 11/1996 |
| WO | WO98/24897 | 6/1998 |
| WO | WO98/40483 | 9/1998 |
| WO | WO98/42739 | 10/1998 |
| WO | WO99/02561 | 1/1999 |
| WO | WO 00/29583 A2 | 5/2000 |

OTHER PUBLICATIONS

Bonaldo et al., Normalization and subtraction: two approaches to facilitate gene discovery. Genome Res. Sep. 1996;6(9):791-806.*
Darnell et al. Molecular Cell Biology. New York: W H Freeman & Co; pp. 248-260, 1986.*
Tsukita et al Multifunctional strands in tight junctions. Nat Rev Mol Cell Biol. Apr. 2001,2(4):281-93.*
Palmeri et al. Vascular endothelial junction-associated molecule, a novel member of the immunoglobulin superfamily, is localized to intercellular boundaries of endothelial cells. J Biol Chem. Jun. 23, 2000,275(25):19139-45.*
Martin-Padura et al., "Junctional Adhesion Molecule , A Novel Member of the Immunoglobulin Superfamily that Distributes at Intercellular Junctions and Modulates Monocyte Transmigration", J. Cell Biology, vol. 142, No. 1, pp. 117-127, Jul. 13, 1998.
Ozaki et al, "Cutting Edge: Combined Treatment of the TNF-alpha and IFN-gamma causes Redistribution of Junctional Adhesion Molecule in Human Endothelial Cells", J. Immunol., vol. 163, No. 2, Jul. 15, 1999.
Alderson et al., "Molecular and Biological Characterization of Human 4-1BB and Its Ligand." European Journal of Immunology. 24(9):2219-2227 (Sep. 1994).
Altschul and Gish, "Local Alignment Statistics" Methods in Enzymology 266:460-480 (1996).
Auffray et al., "H. sapiens partial cDNA sequence; clone c-0xd10. partial cDNA sequence; transcribed sequence fragment" (Database EMBL—EMEST16 Accession No. F02373) (Jan. 28, 1995).
Chambers and Allison., "Co-Stimulation in T Cell Responses." Current Opinion in Immunology. 9(3):396-404 (Jun. 1997).
De Smet et al., "The Activation of Human Gene MAGE-1 in Tumor Cells is Correlated with Genome-Wide Demethylation." Proc. Natl. Acad. Sci. USA 93(14):7149-7153 (Jul. 9, 1996).
Finn and Lotze., "Introduction: Third Keystone Sympsoium on Cellular Immunology and the Immunotherapy of Cancer." Journal of Immunotherapy. 21(2):114-118 (Mar. 1998).
GBTRANS Database, Accession No. AF172398 (blast results) (Direct Submission Feb. 26, 2001).
GBTRANS Database, Accession No. AF191495 (blast results) (Direct Submission Oct. 1, 1999).
GBTRANS Database, Accession No. AJ132502, "HSA132502_1 Z39Ig protein—Homo sapiens" (blast results) (Direct Submission Jan. 25, 1999).
GBTRANS Database, Accession No. AL034397, "HS159A1_1 dA159A1.1 (novel protein)—Homo sapiens" (blast results) (Direct Submission Dec. 4, 1998).

(Continued)

Primary Examiner—Maher M. Haddad
(74) Attorney, Agent, or Firm—Mark T. Kresnak; Elizabeth M. Barnes; Ginger R. Dreger, Esq.

(57) ABSTRACT

The present invention relates to compositions and methods of treating and diagnosing disorders characterized the by the presence of antigens associated with inflammatory diseases and/or cancer, and nucleotide sequences, including expressed sequence tags (ESTs), oligonucleotide probes, polypeptides, vectors and host cells expressing such antigens PRO301, PRO362 or PRO245.

5 Claims, 24 Drawing Sheets

OTHER PUBLICATIONS

GBTRANS Database, Accession No. AL136649, "HSMB01619_1 hypothetical protein" (blast results) (Direct Submission Jan. 18, 2000).
GBTRANS Database, Accession No. AY016009 (blast results) (Direct Submission Dec. 4, 2000).
GBTRANS Database, Search Date Aug. 25, 2003 *Accession No. AAD43794* (Schnell,F.J. et al.), May 25, 1999.
GBTRANS Database, Search Date Aug. 25, 2003 *Accession No. AAF22829* (Sobocka,M.B. et al.), Nov. 19, 1999.
GBTRANS Database, Search Date Aug. 25, 2003 *Accession No. AAF81223* (Palmeri,D et al.), Apr. 14, 2000.
GBTRANS Database, Search Date Aug. 25, 2003 *Accession No. AAG28379* (Gupta,S.K. et al.), Oct. 1, 1999.
GBTRANS Database, Search Date Aug. 25, 2003 *Accession No. AAG49022* (Cunningham,S.A. et al.), Dec. 4, 2000.
GBTRANS Database, Search Date Aug. 25, 2003 *Accession No. AAH01533* (Strausberg,R. et al.), Dec. 21, 2000.
GBTRANS Database, Search Date Aug. 25, 2003 *Accession No. AAH10525* (Strausberg,R et al.), Jul. 10, 2001.
GBTRANS Database, Search Date Aug. 25, 2003 *Accession No. AAH17779* (Strausberg,R et al.), Dec. 3, 2001.
GBTRANS Database, Search Date Aug. 25, 2003 *Accession No. AAL82538* (Slavov,D et al.), Jan. 30, 2002.
GBTRANS Database, Search Date Aug. 25, 2003 *Accession No. AAO84556* (Wenzel,K et al.), Mar. 6, 2002.
GBTRANS Database, Search Date Aug. 25, 2003 *Accession No. BAC11436* (Isogai,T et al.), Mar. 25, 2002.
GBTRANS Database, Search Date Aug. 25, 2003 *Accession No. CAB51536* (Langnaese,K et al.), Jan. 25, 1999.
GBTRANS Database, Search Date Aug. 25, 2003 *Accession No. CAB66584* (Blum,H. et al.), Jul. 10, 2002.
GBTRANS Database, Search Date Aug. 25, 2003 *Accession No. CAE06261* (Bejanin,S. et al.), Jun. 5, 2003.
GBTRANS Database, Search Date Aug. 25, 2003 *Accession No. P AAY23321* (Ashkenazi A et al.), Pub Date Jun. 3, 1999.
GBTRANS Database, Search Date Aug. 25, 2003 *Accession No. P AAY23322* (Ashkenazi A et al.), Pub Date Jun. 3, 1999.
GBTRANS Database, Search Date Aug. 25, 2003 *Accession No. P AAY23326* (Ashkenazi A et al.), Pub Date Jun. 3, 1999.
GBTRANS Database, Search Date Aug. 25, 2003 *Accession No. P AAY23328* (Ashkenazi A et al.), Pub Date Jun. 3, 1999.
GBTRANS Database, Search Date Aug. 25, 2003 *Acession No. AAD48877* (Naik,U.P. et al.), Feb. 26, 2001.
GBTRANS Database, Search Date Aug. 25, 2003 *Accession No. AAD42050* (Ozaki,H et al.), Dec. 6, 1998.
GENESEQ Database, Search Date Sep. 8, 2003 *Accession No. JAM1 HUMAN* (Ozaki H. et al.), Jan. 11, 2003.
GENESEQ Database, Search Date Sep. 8, 2003 *Accession No. JAM2 HUMAN* (Palmeri D. et al.), 2000.
GENESEQ Database, Search Date Sep. 8, 2003 *Accession No. NP 009199* (Langnaese,K et al.), 2000.
GENESEQ Database, Search Date Sep. 8, 2003 *Accession No. NP 058642* (Kornecki,E. et al.), 1990.
GENESEQ Database, Search Date Sep. 8, 2003 *Accession No. NP 067042* (Palmeri,D et al.), 2000.
GENESEQ Database, Search Date Sep. 8, 2003 *Accession No. NP 653084* (Kornecki,E. et al.), 1990.
GENESEQ Database, Search Date Sep. 8, 2003 *Accession No. NP 653085* (Kornecki,E. et al.), 1990.
GENESEQ Database, Search Date Sep. 8, 2003 *Accession No. NP 653086* (Kornecki,E. et al.), 1990.
GENESEQ Database, Search Date Sep. 8, 2003 *Accession No. NP 653087* (Kornecki,E. et al.), 1990.
GENESEQ Database, Search Date Sep. 8, 2003 *Accession No. P AAB19396* (Garcia PD et al.), Pub Date Oct. 19, 2000.
GENESEQ Database, Search Date Sep. 8, 2003 *Accession No. P AAB24047* (Baker KP et al.), Pub Date Sep. 14, 2000.
GENESEQ Database, Search Date Sep. 8, 2003 *Accession No. P AAB24401* (Ashkenazi AJ et al.), Pub Date Jun. 8, 2000.
GENESEQ Database, Search Date Sep. 8, 2003 *Accession No. P AAB24405* (Ashkenazi AJ et al.), Pub Date Jun. 8, 2000.
GENESEQ Database, Search Date Sep. 8, 2003 *Accession No. P AAB31202* (Ashkenazi AJ et al.), Pub Date Dec. 21, 2000.
GENESEQ Database, Search Date Sep. 8, 2003 *Accession No. P AAB33421* (Ashkenazi AJ et al.), Pub Date Sep. 14, 2000.
GENESEQ Database, Search Date Sep. 8, 2003 *Accession No. P AAB44247* (Ashkenazi AJ et al.), Pub Date Sep. 14, 2000.
GENESEQ Database, Search Date Sep. 8, 2003 *Accession No. P AAB50904* (Ashkenazi AJ et al.), Pub Date Dec. 7, 2000.
GENESEQ Database, Search Date Sep. 8, 2003 *Accession No. P AAB53081* (Ashkenazi AJ et al.), Pub Date Sep. 14, 2000.
GENESEQ Database, Search Date Sep. 8, 2003 *Accession No. P AAB53086* (Ashkenazi AJ et al.), Pub Date Sep. 14, 2000.
GENESEQ Database, Search Date Sep. 8, 2003 *Accession No. P AAB55950* (Watson JD et al.), Pub Date Nov. 23, 2000.
GENESEQ Database, Search Date Sep. 8, 2003 *Accession No. P AAB56015* (Watson JD et al.), Pub Date Nov. 23, 2000.
GENESEQ Database, Search Date Sep. 8, 2003 *Accession No. P AAB80222* (Ashkenazi AJ et al.), Pub Date: Jan. 18, 2001.
GENESEQ Database, Search Date Sep. 8, 2003 *Accession No. P AAB80232* (Ashkenazi AJ et al.), Pub Date Jan. 18, 2001.
GENESEQ Database, Search Date Sep. 8, 2003 *Accession No. P AAE03840* (Ruben SM et al.), Pub Date May 25, 2001.
GENESEQ Database, Search Date Sep. 8, 2003 *Accession No. P AAE03870* (Ruben SM et al.), Pub Date May 25, 2001.
GENESEQ Database, Search Date Sep. 8, 2003 *Accession No. P AAE03896* (Ruben SM et al.), Pub Date May 25, 2001.
GENESEQ Database, Search Date Sep. 8, 2003 *Accession No. P AAE04208* (Ruben SM et al.), Pub Date May 25, 2001.
GENESEQ Database, Search Date Sep. 8, 2003 *Accession No. P AAE04230* (Ruben SM et al.), Pub Date May 25, 2001.
GENESEQ Database, Search Date Sep. 8, 2003 *Accession No. P AAE04290* (Ruben SM et al.), Pub Date May 25, 2001.
GENESEQ Database, Search Date Sep. 8, 2003 *Accession No. P AAE26983* (Ruben SM et al.), Pub Date Jun. 20, 2002.
GENESEQ Database, Search Date Sep. 8, 2003 *Accession No. P AAE27121*. (Ruben SM et al.), Pub Date Jun. 20, 2002.
GENESEQ Database, Search Date Sep. 8, 2003 *Accession No. P AAM23693* (Tang YT et al.), Pub Date Aug. 2, 2001.
GENESEQ Database, Search Date Sep. 8, 2003 *Accession No. P AAM93577* (Ota T et al.), Pub Date Sep. 5, 2001.
GENESEQ Database, Search Date Sep. 8, 2003 *Accession No. P AAM93874* (Ota T et al.), Pub Date Sep. 5, 2001.
GENESEQ Database, Search Date Sep. 8, 2003 *Accession No. P AAO16451* (Heuer JG et al.), Pub Date Jan. 30, 2003.
GENESEQ Database, Search Date Sep. 8, 2003 *Accession No. P AAO16452* (Heuer JG et al.), Pub Date Jan. 30, 2003.
GENESEQ Database, Search Date Sep. 8, 2003 *Accession No. P AAU00512* (Cunningham S et al.), Pub Date Mar. 1, 2001.
GENESEQ Database, Search Date Sep. 8, 2003 *Accession No. P AAU00821* (Fong S et al.), Pub Date Mar. 22, 2001.
GENESEQ Database, Search Date Sep. 8, 2003 *Accession No. P AAU00823* (Fong S et al.), Pub Date Mar. 22, 2001.
GENESEQ Database, Search Date Sep. 8, 2003 *Accession No. P AAU12339* (Baker KP et al.), Pub Date Jun. 7, 2001.
GENESEQ Database, Search Date Sep. 8, 2003 *Accession No. P AAU12354* (Baker KP et al.), Pub Date Jun. 7, 2001.
GENESEQ Database, Search Date Sep. 8, 2003 *Accession No. P AAU14168* (Tang YT et al.), Pub Date Aug. 2, 2001.
GENESEQ Database, Search Date Sep. 8, 2003 *Accession No. P AAU14169* (Tang YT et al.), Pub Date Aug. 2, 2001.
GENESEQ Database, Search Date Sep. 8, 2003 *Accession No. P AAU14404* (Tang YT et al.), Pub Date Aug. 2, 2001.
GENESEQ Database, Search Date Sep. 8, 2003 *Accession No. P AAU14405* (Tang YT et al.), Pub Date Aug. 2, 2001.
GENESEQ Database, Search Date Sep. 8, 2003 *Accession No. P AAU17996* (Rosen CA et al.), Pub Date Aug. 2, 2001.
GENESEQ Database, Search Date Sep. 8, 2003 *Accession No. P AAW61379* (Dejana E et al.), Pub Date Jun. 11, 1998.
GENESEQ Database, Search Date Sep. 8, 2003 *Accession No. P AAW74464* (Gupta SK et al.), Pub Date Jan. 21, 1999.
GENESEQ Database, Search Date Sep. 8, 2003 *Accession No. P AAW75220* (Ferrie AM et al.), Pub Date Sep. 17, 1998.

GENESEQ Database, Search Date Sep. 8, 2003 *Accession No. P AAW85457* (Agostino MJ et al.), Pub Date Oct. 1, 1998.
GENESEQ Database, Search Date Sep. 8, 2003 *Accession No. P AAY08060* (Fong S et al.), Pub Date: Mar. 25, 1999.
GENESEQ Database, Search Date Sep. 8, 2003 *Accession No. P AAY08071* (Fong S et al.), Pub Date Mar. 25, 1999.
GENESEQ Database, Search Date Sep. 8, 2003 *Accession No. P AAY08072* (Fong S et al.), Pub Date Mar. 25, 1999.
GENESEQ Database, Search Date Sep. 8, 2003 *Accession No. P AAY08074* (Fong S et al.), Pub Date Mar. 25, 1999.
GENESEQ Database, Search Date Sep. 8, 2003 *Accession No. P AAY13354* (Chen J et al.), Pub Date Mar. 25, 1999.
GENESEQ Database, Search Date Sep. 8, 2003 *Accession No. P AAY13364* (Chen J et al.), Pub Date Mar. 25, 1999.
GENESEQ Database, Search Date Sep. 8, 2003 *Accession No. P AAY23324* (Ashkenazi A et al.), Pub Date: Jun. 3, 1999.
GENESEQ Database, Search Date Sep. 8, 2003 *Accession No. P AAY41691* (Wood WI et al.), Pub Date Sep. 16, 1999.
GENESEQ Database, Search Date Sep. 8, 2003 *Accession No. P AAY70668* (Fong S et al.), Pub Date Mar. 23, 2000.
GENESEQ Database, Search Date Sep. 8, 2003 *Accession No. P AAY70670* (Fong S et al.), Pub Date Mar. 23, 2000.
GENESEQ Database, Search Date Sep. 8, 2003 *Accession No. P AAY76011* (Strachan L et al.), Pub Date Nov. 4, 1999.
GENESEQ Database, Search Date Sep. 8, 2003 *Accession No. P AAY76076* (Strachan L et al.), Pub Date Nov. 4, 1999.
GENESEQ Database, Search Date Sep. 8, 2003 *Accession No. P AAY95344* (Ashkenazi AJ et al.), Pub Date Jun. 29, 2000.
GENESEQ Database, Search Date Sep. 8, 2003 *Accession No. P AAY95346* (Ashkenazi AJ et al.), Pub Date Jun. 29, 2000.
GENESEQ Database, Search Date Sep. 8, 2003 *Accession No. P ABB10232* (Rosen CA et al.), Pub Date Aug. 2, 2001.
GENESEQ Database, Search Date Sep. 8, 2003 *Accession No. P ABB72150* (Watson JD et al.), Pub Date Nov. 29, 2001.
GENESEQ Database, Search Date Sep. 8, 2003 *Accession No. P ABB72215* ( Watson JD et al.), Pub Date Nov. 29, 2001.
GENESEQ Database, Search Date Sep. 8, 2003 *Accession No. P ABB84843* (Baker KP et al.), Pub Date Jan. 3, 2002.
GENESEQ Database, Search Date Sep. 8, 2003 *Accession No. P ABB90290* (Birse CE et al.), Pub Date Nov. 29, 2001.
GENESEQ Database, Search Date Sep. 8, 2003 *Accession No. P ABB95449* (Baker KP et al.), Pub Date Jan. 31, 2002.
GENESEQ Database, Search Date Sep. 8, 2003 *Accession No. P ABG22341* (Drmanac RT et al.), Pub Date Oct. 11, 2001.
GENESEQ Database, Search Date Sep. 8, 2003 *Accession No. P ABG64487* (Rosen CA et al.), Pub Date Oct. 18, 2001.
GENESEQ Database, Search Date Sep. 8, 2003 *Accession No. P ABG64488* (Rosen CA et al.), Pub Date Oct. 18, 2001.
GENESEQ Database, Search Date Sep. 8, 2003 *Accession No. P ABG64551* (Rosen CA et al.), Pub Date Oct. 18, 2001.
GENESEQ Database, Search Date Sep. 8, 2003 *Accession No. P ABG64552* (Rosen CA et al.), Pub Date Oct. 18, 2001.
GENESEQ Database, Search Date Sep. 8, 2003 *Accession No. P ABO01784* (Ashkenazi A et al.), Pub Date Dec. 26, 2002.
GENESEQ Database, Search Date Sep. 8, 2003 *Accession No. P ABO01794* (Ashkenazi A et al.), Pub Date Dec. 26, 2002.
GENESEQ Database, Search Date Sep. 8, 2003 *Accession No. P ABO14814* (Ashkenazi A et al.), Pub Date Feb. 6, 2003.
GENESEQ Database, Search Date Sep. 8, 2003 *Accession No. P ABO14824* (Ashkenazi A et al.), Pub Date Feb. 6, 2003.
GENESEQ Database, Search Date Sep. 8, 2003 *Accession No. P ABP61801* (Jacobs K et al.), Pub Date May 30, 2002.
GENESEQ Database, Search Date Sep. 8, 2003 *Accession No. P ABP66819* (Rosen CA et al.), Pub Date Jul. 11, 2002.
GENESEQ Database, Search Date Sep. 8, 2003 *Accession No. P ABR00157* (Rosen CA et al.), Pub Date Oct. 3, 2002.
GENESEQ Database, Search Date Sep. 8, 2003 *Accession No. P ABR00172* (Rosen CA et al.), Pub Date Oct. 3, 2002.
GENESEQ Database, Search Date Sep. 8, 2003 *Accession No. P ABR47904* (Rosen CA et al.), Pub Date Nov. 28, 2002.
GENESEQ Database, Search Date Sep. 8, 2003 *Accession No. P ABR47926* (Rosen CA et al.), Pub Date Nov. 28, 2002.
GENESEQ Database, Search Date Sep. 8, 2003 *Accession No. P ABR58532* (Afar D et al.), Pub Date Mar. 27, 2003.
GENESEQ Database, Search Date Sep. 8, 2003 *Accession No. P ABU03567* (Murray R et al.), Pub Date Oct. 10, 2002.
GENESEQ Database, Search Date Sep. 8, 2003 *Accession No. P ABU07736* (Ashkenazi A et al.), Pub Date Dec. 5, 2002.
GENESEQ Database, Search Date Sep. 8, 2003 *Accession No. P ABU07737* (Ashkenazi A et al.), Pub Date Dec. 5, 2002.
GENESEQ Database, Search Date Sep. 8, 2003 *Accession No. P ABU07738* (Ashkenazi A et al.), Pub Date Dec. 5, 2002.
GENESEQ Database, Search Date Sep. 8, 2003 *Accession No. P ABU54357* (Ashkenazi A et al.), Pub Date: Sep. 19, 2002.
GENESEQ Database, Search Date Sep. 8, 2003 *Accession No. P ABU54367* (Ashkenazi A et al.), Pub Date Sep. 19, 2002.
GENESEQ Database, Search Date Sep. 8, 2003 *Accession No. P ABU59818* (Baker KP et al.), Pub Date Jan. 23, 2003.
GENESEQ Database, Search Date Sep. 8, 2003 *Accession No. P ABU59833* (Baker KP et al.), Pub Date Jan. 23, 2003.
GENESEQ Database, Search Date Sep. 8, 2003 *Accession No. P ABU61077* (Ashkenazi A et al.), Pub Date Nov. 14, 2002.
GENESEQ Database, Search Date Sep. 8, 2003 *Accession No. P ABU64519* (Ashkenazi A et al.), Pub Date Oct. 31, 2002.
GENESEQ Database, Search Date Sep. 8, 2003 *Accession No. P ABU64994* (Ruben SM et al.), Pub Date Nov. 21, 2002.
GENESEQ Database, Search Date Sep. 8, 2003 *Accession No. P ABU66737* (Baker KP et al.), Pub Date Feb. 20, 2003.
GENESEQ Database, Search Date Sep. 8, 2003 *Accession No. P ABU66752* (Baker KP et al.), Pub Date Feb. 20, 2003.
GENESEQ Database, Search Date Sep. 8, 2003 *Accession No. P ABU67013* (Baker KP et al.), Pub Date Feb. 13, 2003.
GENESEQ Database, Search Date Sep. 8, 2003 *Accession No. P ABU67028* (Baker KP et al.), Pub Date Feb. 13, 2003.
GENESEQ Database, Search Date Sep. 8, 2003 *Accession No. P ABU67160* (Ashkenazi AJ et al.), Pub Date Feb. 13, 2003.
GENESEQ Database, Search Date Sep. 8, 2003 *Accession No. P ABU67291* (Ashkenazi AJ et al.), Pub Date Feb. 13, 2003.
GENESEQ Database, Search Date Sep. 8, 2003 *Accession No. P ABU67365* (Ashkenazi A et al.), Pub Date: Jan. 30, 2003.
GENESEQ Database, Search Date Sep. 8, 2003 *Accession No. P ABU69632* (Ashkenazi A et al.), Pub Date Jan. 23, 2003.
GENESEQ Database, Search Date Sep. 8, 2003 *Accession No. P ABU69642* (Ashkenazi A et al.), Pub Date Jan. 23, 2003.
GENESEQ Database, Search Date Sep. 8, 2003 *Accession No. P ABU71455* (Ashkenazi A et al.), Pub Date Dec. 19, 2002.
GENESEQ Database, Search Date Sep. 8, 2003 *Accession No. P ABU71465* (Ashkenazi A et al.), Pub Date Dec. 19, 2002.
GENESEQ Database, Search Date Sep. 8, 2003 *Accession No. P ABU71600* (Ashkenazi A et al.), Pub Date Oct. 10, 2002.
GENESEQ Database, Search Date Sep. 8, 2003 *Accession No. P ABU71610* (Ashkenazi A et al.), Pub Date Oct. 10, 2002.
GENESEQ Database, Search Date Sep. 8, 2003 *Accession No. P ABU71901* (Ashkenazi A et al.), Pub Date Jan. 2, 2003.
GENESEQ Database, Search Date Sep. 8, 2003 *Accession No. P ABU71911* (Ashkenazi A et al.), Pub Date Jan. 2, 2003.
GENESEQ Database, Search Date Sep. 8, 2003 *Accession No. P ABU72059* (Ashkenazi AJ et al.), Pub Date Nov. 28, 2002.
GENESEQ Database, Search Date Sep. 8, 2003 *Accession No. P ABU72199* (Ashkenazi AJ et al.), Pub Date Dec. 19, 2002.
GENESEQ Database, Search Date Sep. 8, 2003 *Accession No. P ABU79802* (Ashkenazi AJ et al.), Pub Date Feb. 13, 2003.
GENESEQ Database, Search Date Sep. 8, 2003 *Accession No. P ABU80346* (Ashkenazi AJ et al.), Pub Date Jan. 2, 2003.
GENESEQ Database, Search Date Sep. 8, 2003 *Accession No. P ABU81037* (Baker KP et al.), Pub Date Jan. 2, 2003.
GENESEQ Database, Search Date Sep. 8, 2003 *Accession No. P ABU81052* (Baker KP et al.), Pub Date Jan. 2, 2003.
GENESEQ Database, Search Date Sep. 8, 2003 *Acession No. P ABU67355* (Ashkenazi A et al.), Pub Date Jan. 30, 2003.
GENESEQ Database, Search Date Sep. 8, 2003, *Accession No. P ABU64509* (Ashkenazi A et al.), Pub Date Oct. 31, 2002.
GENESEQ Patent Database, Accession No. P_B19396 (blast results) (Oct. 19, 2000).

GENESEQ Patent Database, Accession No. P_B24047 (blast results) (Sep. 14, 2000).
GENESEQ Patent Database, Accession No. P_B24401 (blast results) (Jun. 8, 2000).
GENESEQ Patent Database, Accession No. P_B24405 (blast results) (Jun. 8, 2000).
GENESEQ Patent Database, Accession No. P_B33421 (blast results) (Sep. 14, 2000).
GENESEQ Patent Database, Accession No. P_B33429 (blast results) (Sep. 14, 2000).
GENESEQ Patent Database, Accession No. P_B44247 (blast results) (Sep. 14, 2000).
GENESEQ Patent Database, Accession No. P_B53081 (blast results) (Sep. 14, 2000).
GENESEQ Patent Database, Accession No. P_B53086 (blast results) (Sep. 14, 2000).
GENESEQ Patent Database, Accession No. P_B55950 (blast results) (Nov. 23, 2000).
GENESEQ Patent Database, Accession No. P_B56015 (blast results) (Nov. 23, 2000).
GENESEQ Patent Database, Accession No. P_W61379 (blast results) (Jun. 11, 1998).
GENESEQ Patent Database, Accession No. P_W74464 (blast results) (Jan. 21, 1999).
GENESEQ Patent Database, Accession No. P_W75220 (blast results) (Sep. 17, 1998).
GENESEQ Patent Database, Accession No. P_W85457 (blast results) (Oct. 1, 1998).
GENESEQ Patent Database, Accession No. P_Y08060 (blast results) (Mar. 25, 1999).
GENESEQ Patent Database, Accession No. P_Y08071 (blast results) (Mar. 25, 1999).
GENESEQ Patent Database, Accession No. P_Y08072 (blast results) (Mar. 25, 1999).
GENESEQ Patent Database, Accession No. P_Y08074 (blast results) (Mar. 25, 1999).
GENESEQ Patent Database, Accession No. P_Y13354 (blast results) (Mar. 25, 1999).
GENESEQ Patent Database, Accession No. P_Y13364 (blast results) (Mar. 25, 1999).
GENESEQ Patent Database, Accession No. P_Y23321 (blast results) (Jun. 3, 1999).
GENESEQ Patent Database, Accession No. P_Y23322 (blast results) (Jun. 3, 1999).
GENESEQ Patent Database, Accession No. P_Y23324 (blast results) (Jun. 3, 1999).
GENESEQ Patent Database, Accession No. P_Y23326 (blast results) (Jun. 3, 1999).
GENESEQ Patent Database, Accession No. P_Y23328 (blast results) (Jun. 3, 1999).
GENESEQ Patent Database, Accession No. P_Y41691 (blast results) (Sep. 16, 1999).
GENESEQ Patent Database, Accession No. P_Y70668 (blast results) (Mar. 23, 2000).
GENESEQ Patent Database, Accession No. P_Y70670 (blast results) (Mar. 23, 2000).
GENESEQ Patent Database, Accession No. P_Y76011 (blast results) (Nov. 4, 1999).
GENESEQ Patent Database, Accession No. P_Y76076 (blast results) (Nov. 4, 1999).
GENESEQ Patent Database, Accession No. P_Y95344 (blast results) (Jun. 29, 2000).
GENESEQ Patent Database, Accession No. P_Y95346 (blast results) (Jun. 29, 2000).
Heath et al., "The human A33 antigen is a transmembrane glycoprotein and a novel member of the immunoglobulin superfamily" *Proc. Natl. Acad. Sci. USA* 94(2):469-474 (Jan. 21, 1997).
Hellstrom and Hellstrom., "T Cell Immunity to Tumor Antigens." *Critical Reviews in Immunology*. 18(1-2):1-6 (1998).
Hiller et al., "zb18h08.r1 Soares fetal lung NbHL19W *Homo sapiens* cDNA clone 302463 5'" (Database EMBL—EMEST13 Accession No. W17367) (May 4, 1996).
Hiller et al., "zd74g06.r1 Soares fetal heart NbHH19W *Homo sapiens* cDNA clone 346426 5'" (Database EMBL—EMEST14 Accession No. W79882) (Jun. 27, 1996).
"Isolation of Mouse Mononuclear Cells" *Current Protocols in Immunology*, Coligan et al. eds., John Wiley & Sons, Inc. vol. 1:unit 3.1.2 (1993).
Jenkins, M., "The Ups and Downs of T Cell Costimulation." *Immunity*. 1(6):443-446 (Sep. 1994).
June et al., "The B7 and CD28 Receptor Families." *Immunology Today*. 15(7):321-331 (Jul. 1994).
Kwon et al., "Manipulation of T Cell Costimulatory and Inhibitory Signals for Immunotherapy of Prostate Cancer." *Proc. Natl. Acad. Sci. USA* 94(15):8099-8103 (Jul. 22, 1997).
Linsley and Ledbetter., "The Role of the CD28 Receptor During T Cell Responses to Antigen." *Annu. Rev. Immunol.* 11:191-212 (1993).
Lynch et al., "Flt3 Ligand Induces Tumor Regression and Antitumor Immune Responses In Vivo." *Nature Medicine*. 3(6):625-631 (Jun. 1997).
Martin-Padura et al., "Junctional adhesion molecule, a novel member of the immunoglobulin superfamily that distributes at intercellular junctions and modulates monocyte transmigration" *Journal of Cell Biology* 142(1):117-127 (Jul. 13, 1998).
Melero et al., "Monoclonal Antibodies Against the 4-1BB T-cell Activation Molecule Eradicate Established Tumors." *Nature Medicine*. 3(6):682-685 (Jun. 1997).
Monks et al., "Feasibility of a High-Flux Anticancer Drug Screen Using a Diverse Panel of Cultured Human Tumor Cell Lines" *J. Natl. Cancer Institute* 83(11):757-766 (Jun. 5, 1991).
REFSEQ Database, Accession No. NM_01646 (blast results) (1999).
REFSEQ Database, Accession No. NM_021219 (blast results) (2000).
Schwartz, R., "Costimulation of T Lymphocyte: The Role of CD28, CTLA-4, and B7/BB1 in Interleukin-2 Production and Immunotherapy." *Cell*. 71(7):1065-1068 (Dec. 24, 1992).
Skehan et al., "New Colorimetric Cytotoxicity Assay for Anticancer-Drug Screening" *J. Natl. Cancer Institute* 82(13):1107-1112 (Jul. 4, 1990).
Swissprot (SPROT) Database, Accession No. P57087, "VEJA_HUMAN Vascular endothelial junction-associated molecule precursor—*Homo sapiens*" (blast results) (2000).
Swissprot (SPROT) Database, Accession No. Q9Y624, "JAM1_HUMAN Junctional adhesion molecule precursor—*Homo sapiens*" (blast results) (1999).
Walunas et al., "CTLA-4 Can Function as a Negative Regulator of T Cell Activation." *Immunity*. 1(5):405-413 (Aug. 1994).
Welt et al., "Phase I/II study of iodine 131-labeled monoclonal antibody A33 in patients with advanced colon cancer" *Journal of Clinical Oncology* 12(8):1561-1571 (Aug. 1994).
Welt et al., "Quantitative analysis of antibody localization in human metastatic colon cancer: a phase I study of monoclonal antibody A33" *Journal of Clinical Oncology* 8(11):1894-1906 (Nov. 1990).

* cited by examiner

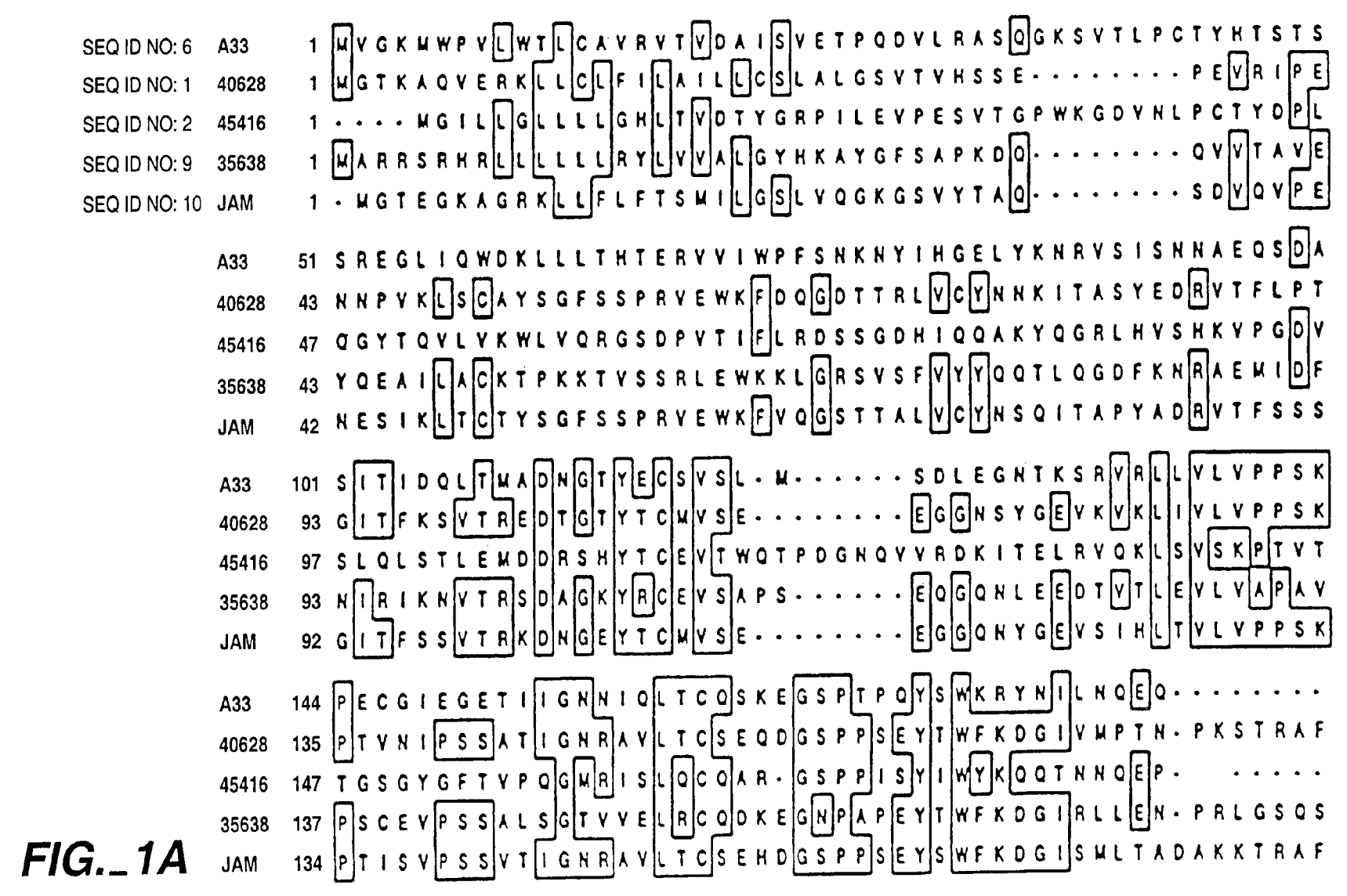

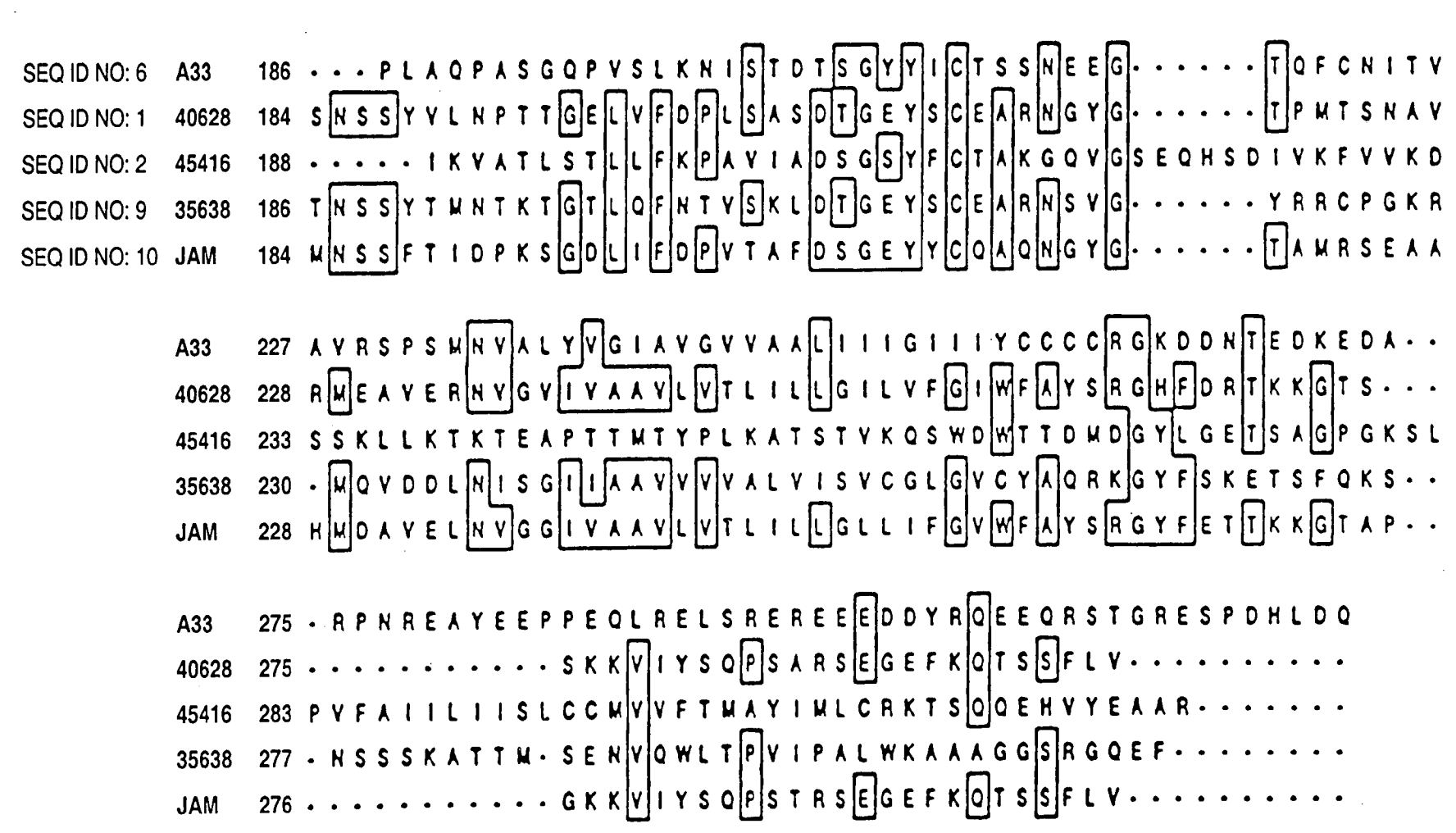

SEQ ID NO:1

Met Gly Thr Lys Ala Gln Val Glu Arg Lys Leu Leu Cys Leu Phe Ile Leu Ala Ile Leu Leu Cys Ser Leu Ala Leu Gly Ser Val Thr
1                                   5                                  10                                  15                                  20                                  25                                  30

Val His Ser Ser Glu Pro Glu Val Arg Ile Pro Glu Asn Asn Pro Val Lys Leu Ser Cys Ala Tyr Ser Gly Phe Ser Ser Pro Arg Val
                                    35                                  40                                  45                                  50                                  55                                  60

Glu Trp Lys Phe Asp Gln Gly Asp Thr Thr Arg Leu Val Cys Tyr Asn Asn Lys Ile Thr Ala Ser Tyr Glu Asp Arg Val Thr Phe Leu
                                    65                                  70                                  75                                  80                                  85                                  90

Pro Thr Gly Ile Thr Phe Lys Ser Val Thr Arg Glu Asp Thr Gly Thr Tyr Thr Cys Met Val Ser Glu Glu Gly Asn Ser Tyr Gly
                                    95                                  100                                 105                                 110                                 115                                 120

Glu Val Lys Val Lys Leu Ile Val Leu Val Pro Pro Ser Lys Pro Thr Val Asn Ile Pro Ser Ser Ala Thr Ile Gly Asn Arg Ala Val
                                    125                                 130                                 135                                 140                                 145                                 150

Leu Thr Cys Ser Glu Gln Asp Gly Ser Pro Pro Ser Glu Tyr Thr Trp Phe Lys Asp Gly Ile Val Met Pro Thr Asn Pro Lys Ser Thr
                                    155                                 160                                 165                                 170                                 175                                 180

Arg Ala Phe Ser Asn Ser Ser Tyr Val Leu Asn Pro Thr Thr Gly Glu Leu Val Phe Asp Pro Leu Ser Ala Ser Asp Thr Gly Glu Tyr
                                    185                                 190                                 195                                 200                                 205                                 210

Ser Cys Glu Ala Arg Asn Gly Tyr Gly Thr Pro Met Thr Ser Asn Ala Val Arg Met Glu Ala Val Glu Arg Asn Val Gly Val Ile Val
                                    215                                 220                                 225                                 230                                 235                                 240

Ala Ala Val Leu Val Thr Leu Ile Leu Leu Gly Ile Leu Val Phe Gly Ile Trp Phe Ala Tyr Ser Arg Gly His Phe Asp Arg Thr Lys
                                    245                                 250                                 255                                 260                                 265                                 270

Lys Gly Thr Ser Ser Lys Lys Val Ile Tyr Ser Gln Pro Ser Ala Arg Ser Glu Gly Glu Phe Lys Gln Thr Ser Ser Phe Leu Val
                                    275                                 280                                 285                                 290                                 295                                 299

FIG._2

SEQ ID NO:2

1   MGILLGLLLL GHLTVDTYGR PILEVPESVT GPWKGDVNLP CTYDPLQGYT QVLVKWLVQR GSDPVTIFLR DSSGDHIQQA KYQGRLHVSH KVPGDVSLQL

101 STLEMDDRSH YTCEVTWQTP DCNQVVRDKI TELRVQKLSV SKPTVTTGSG YGFTVPQGMR ISLQCQARGS PPISYIWYKQ QTNNQEPIKV ATLSTLLFKP
                                                        ‾Glycosaminoglycan attachment site 201 AVIADSGSYF CTAKGQVGSE QHSDIVKFVV KDSSKLLKTK TEAPTMTYP LKATSTVKQS WDWTTDMDGY LGETSAGPGK SLPVFAIILI ISLCCMVVFT
                                                                                                    ‾Transmembrane domain

301 MAYIMLCRKT SQQEHVYEAA R

FIG._3

OLI2162 (35936.f1)
SEQ ID NO:12

TCGCGGAGCTGTGTTCTGTTCCC

OLI2163 (35936.p1)
SEQ ID NO:13

TGATCGCGATGGGGACAAAGGGCGCAAGCTCGAGAGAGGAAACTGTTGTGCCT

OLI2164 (35936.f2)
SEQ ID NO:14

ACACCTGGTTCAAAGATGGG

OLI2165 (35936.r1)
SEQ ID NO:15

TAGGAAGAGTTGCTGAAGGCACGG

OLI2166 (35936.f3)
SEQ ID NO:16

TTGCCTTACTCAGGTGCTAC

OLI2167 (35936.r2)
SEQ ID NO:17

ACTCAGCAGTGGTAGGAAAG

FIG._8

DNA35936   SEQ ID NO:3

```
CTTCTTGCCA ACTGGTATCA CCTTCAAGTC CGTGACACGG GAAGACACTG 50
GGACATACAC TTGTATGGTC TCTGAGGAAG GCGGCAACAG CTATGGGGAG 100
GTCAAGGTCA AGCTCATCGT GCTTGTGCCT CCATCCAAGC CTACAGTTAA 150
CATCCCCTCC TCTGCCACCA TGGGAACCGG GCAGTGCTG ACATGCTCAG 200
AACAAGATGG TTCCCCACCT TCTGAATACA CCTGGTTCAA AGATGGATA 250
GTGATGCCTA CGAATCCCAA AAGCACCCGT GCCTTCAGCA ACTCTTCCTA 300
TGTCCTGAAT CCCACAACAG GAGAGCTGGT CTTTGATCCC CTGTCAGCCT 350
CTGATACTGG AGAATACAGC TGTGAGGCAC GGAATGGGTA 390
```

FIG._4A consen01   SEQ ID NO:4

```
TCTCAGTCCC CTCGCTGTAG TCGCGGAGCT GTGTTCTGTT TCCCAGGAGT 50
CCTTCGGCGG CTGTTGTGCT CAGGTGCGCC TGATCGCGAT GGGGACAAAG 100
GCGCAAGCTC GAGAGGAAAC TGTTGTGCCT CTTCATATTG GCGATCCTGT 150
TGTGCTCCCT GGCATTGGGC AGTGTTACAG TTGCACTCTT CTGAACCTGA 200
AGTCAGAATT CCTGAGAATA ATCCTGTGAA GTTGTCCTGT GCCTACTCGG 250
GCTTTTCTTC TCCCCGTGTG GAGTGGAAGT TTGACCAAGG AGACACCACC 300
AGACTCGTTT GCTATAATAA CAAGATCACA GCTTCCTATG AGGACCGGGT 350
GACCTTCTTG CCAACTGGTA TCACCTTCAA GTCCGTGACA CGGGAAGACA 400
CTGGGACATA CACTTGTATG GTCTCTGAGG AAGGCGGCAA CAGCTATGGG 450
GAGGTCAAGG TCAAGCTCAT CGTGCTTGTG CCTCCATCCA AGCCTACAGT 500
TAACATCCCC TCCTCTGCCA CCATTGGGAA CCGGGCAGTG CTGACATGCT 550
CAGAACAAGA TGGTTCCCCA CCTTCTGAAT ACACCTGGTT CAAAGATGGG 600
ATAGTGATGC CTACGAATCC CAAAAGCACC CGTGCCTTCA GCAACTCTTC 650
CTATGTCCTG AATCCCACAA CAGGAGAGCT GGTCTTTGAT CCCCTGTCAG 700
CCTCTGATAC TGGAGAATAC AGCTGT 726
```

FIG._4B consen02    SEQ ID NO:5

```
GCAGGCAAAG TACCAGGGCC GCCTGCATGT GAGCCACAAG GTTCCAGGAG   50
ATGTATCCCT CCAATTGAGC ACCCTGGAGA TGGATGACCG GAGCCACTAC  100
ACGTGTGAAG TCACCTGGCA GACTCCTGAT GGCAACCAAG TCGTGAGAGA  150
TAAGATTACT GAGCTCCGTG TCCAGAAACT CTCTGTCTCC AAGCCCACAG  200
TGACAACTGG CAGCGGTTAT GGCTTCACGG TGCCCCAGGG AATGAGGATT  250
AGCCTTCAAT GCCAGGGTTC GGGGTTCTCC TCCCATCAGT TATATTTGGT  300
ATAAGCAACA GACTAATAAC CAGGGAACCC ATCAAAGTAG CAACCCTAAG  350
TACCTTACTC TTCAAGCCTG CGGTGATAGC CGACTCAGGC TCCTATTTCT  400
GCACTGCCAA GGGCCAGGTT GGCTCTGAGC AGCACAGCGA CATTGTGAAG  450
TTTGTGGTCA AAGACTCCTC AAAGCTACTC AAGACCAAGA CTGAGGCACC  500
TACAACCATG ACATACCCCT TGAAAGCAAC ATCTACAGTG AAGCAGTCCT  550
GGGACTGGAC CACTGACATG GATGGCTACC TTGGAGAGAC CAGTGCTGGG  600
CCAGGAAAGA GCCTGCCTGT CTTTGCCATC ATCCTCATCA TCTCCTTGTG  650
CTGTATGGTG GTTTTACCA TGGCCTATAT CATGCTCTGT CGGAAGACAT  700
CCCAACAAGA GCATGTCTAC GAAGCAGCCA GGGCACATGC CAGAGAGGCC  750
AACGACTCTG GAGAAACCAT GAGGGTGGCC ATCTTCGCAA GTGGCTGCTC  800
CAGTGATGAG CCAACTTCCC AGAATCTGGG GCAACAACTA CTCTGATGAG  850
CCCTGCATAG GACAGGAGTA CCAGATCATC GCCCAGATCA ATGGCAACTA  900
CGCCCGCCTG CTGGACACAG TTCCTCTGGA TTATGAGTTT CTGGCCACTG  950
AGGGCAAAAG TGTCTGTTAA AAATGCCCCA TTAGGCCAGG ATCTGCTGAC 1000
ATAATTGCCT AGTCAGTCCT TGCCTTCTGC ATGGCCTTCT TCCCTGCTAC 1050
CTCTCTTCCT GGATAGCCCA AAGTGTCCGC CTACCAACAC TGGAGCCGCT 1100
GGGAGTCACT GGCTTTGCCC TGGAATTTGC CAGATGCATC TCAAGTAAGC 1150
CAGCTGCTGG ATTTGGCTCT GGGCCTTCT AGTATCTCTG CCGGGGGCTT 1200
CTGGTACTCC TCTCTAAATA CCAGAGGGAA GATGCCCATA GCACTAGGAC 1250
TTGGTCATCA TGCCTACAGA CACTATTCAA CTTTGGCATC TTGCCACCAG 1300
AAGACCCGAG GGGAGGCTCA GCTCTGCCAG CTCAGAGGAC CAGCTATATC 1350
CAGGATCATT TCTCTTTCTT CAGGGCCAGA CAGCTTTTAA TTGAAATTGT 1400
TATTTCACAG GCCAGGGTTC AGTTCTGCTC CTCCACTATA AGTCTAATGT 1450
TCTGACTCTC TCCTGGTGCT CAATAAATAT CTAATCATAA CAGCAAAAAA 1500
AAA 1503
```

FIG._4C

SEQ ID NO:11

```
GTCTGTTCCC AGGAGTCCTT CGGCGGGCTGT CTGGCATTGG GCAGTGTTAC AGTGCACTCT TCTGAACCTG AAGTCAGAAT TCCTGAGAAT AATCCTGTGA AGTTGTCCTG  200
TGCCTACTCG GGCTTTTCTT CTCCCCGTGT GGAGTGGAAG TTTGACCAAG GAGACACCAC CAGACTCGTT TGCTATAATA ACAAGATCAC AGCTTCCTAT  300
GAGGACCGGG TGACCTTCTT GCCAACTTCA AGTCCGTGAC ACGGAAAGAC ACTGGGACAT ACACTTGTAT GGTCTCTGAG GAAGGCGGCA  400
ACAGCTATGG GGAGGTCAAG GTCAAGCTCA TCGTGCTTGT GCCTCCATCC AAGCCTACAG TTAACATCCC CTCCCTCTGC ACCATTGGGA ACCGGGCAGT  500
GCTGACATGC TCAGAACAAG ATGGTTCCCC ACCTTCTGAA TACACCTGGT TCAAAGATGG GATAGTGATG CCTACGAATC CCAAAAGCAC CCGTGCCTTC  600
AGCAACTCTT CCTATGTCCT GAATCCCACA ACAGGAGAGC TGGTCTTTGA TCCCCTGTCA GCCTCTGATA CTGGAGAATA CAGCTGTGAG GCACGGAATG  700
GGTATGGGAC ACCCATGACT TCAAATGCTG TGCGCATGGA AGCTGTGGAG CGGAATGTGG GGGTCATCGT GAAATGGGAC CTTGTAACCC TGATTCTCCT  800
GGGAATCTTG GTTTTTGGCA TCTGGTTTGC CTATAGCCGA GGCCACTTTG ACAGAACAAA GAAAGGGACT TCGAGTAAGA AGGTGATTTA CAGCCAGCCT  900
AGTCCCCGAA GTGAAGGAGA ATTCAAACAG ACCTCGTCAT TCCTGGGTGTG AGCCTGGTCG GCTCACCGCC TATCATCTGC ATTTGCCTTA CTCAGGTGCT  1000
ACCGGACTCG GGCCCCTGAT GTCTGTAGTT TCACAGGATG CTTCTACACC CCCTACTTCT TGTTAAAGT GTTTATTCCC CATTCTTTG  1200
GTCAGCTATG TGCCCCATCC TCCTTCATGC CCTCCCCTCC CTGCTGAGTG GCCTGGAACT CTGCTGAGTG GCCTGGAACT TGTTAAAGT GTTTATTCCC CATTCTTTG  1200
AGGGATCAGG AAGGAAATCCT GGGTATGCCA TTGACTTCCC TTCTAAGTAG ACAGCAAAAA TGGGCGGGGT CGCAGGAATC TGCACTCAAC TGCCCACCTG  1300
GCTGGCAGGG ATCTTTGAAT AGTATCTTG TGGGCTCTTT CCTTGTGTAC TGACGACCAG GGCCAGCTGT TCTAGAGCGG GAATTAGAGG  1400
CTAGAGCGGC TGAAATGGTT GTTTGGTGAT GACACTGGTG TCCTTCCATC TCTGGGGCCC ACTCTCTTCT GTCTTCCCAT GGGAAGTGCC ACTGGGATCC  1500
CTCTGCCCTG TCCTTCCTGA TACAAGCTGA CTGACATTGA CTGTGTCTGT AGCTCTTGTT GTGGAGAGCA TAGTAAATTT TCAGAGAACT  1600
TGAAGCCAAA AGGATTTAAA ACCGCTGCTC TAAAGAAAAG GCTGGGCGCA GTGGCTCACG CCTGTAATCC CAGAGGCTGA GGCAGGCGGA  1700
TCACCTGAGG TCGGGAGTTC GGGATCAGCC TGACCAACAT GGAGAAACCC TACTGGAAAT ACAAAGTTAG CCAAGGCATGG TGGTGCATGC CTGTAGTCCC  1800
AGCTGCTCAG GAGCCTGGCA ACAAGAGCAA AACTCCAGCT CA 1842
```

Figure 5

SEQ ID NO:7

```
  1 CCCAGCGCTC CGCCCACGCG TCCGCCCACG GGTCCGCCCA CGCGTCCGGG CCACCAGGAA GTTTGGTAGCA GGAGGCTGGA AGAAAGGACA
    GGGTGCGCGAG GCGGGTGCGC AGGGCGGGTGC CCAGGAGCC GCGCAGGGCCC CGTGGTCCTT CAAACCATCGT CCTCCGACCT TCTTTCCTGT

101 GAAGTAGCTC TGGCTGTGAT GGGGATCTTA CTGGGCCTGC TACTCCTGGG GCACCTAACA GTGGACACTT ATGGCCGTCC CATCCTGGAA GTGCCAGGA GA
    CTTCATCGAG ACCGACACTA CCCCTAGAAT GACCCGGACG ATGAGGACCC CGTGGATTGT CACCTGTGAA TACCGGCAGG GTAGGACCTT CACGGTCTCT
  1                       M  G  I  L  L  G  L  L  L  L  G  H  L  T  V  D  T  Y  G  R  P  I  L  E  V  P  E  S
                         ^MET

201 GTGTAACAGG ACCTTGGAAA GGGGATGTGA ATCTTCCCTG CACCTATGAC CCCCTCCAAG GCTACACCCA AGTCTTGGTG AAGTGGCTGG TACAACGTGG
    CACATTGTCC TGGAACCTTT CCCCTACACT TAGAAGGGAC GTGGATACTG GGGGAGGTTC CGATGTGGGT TCAGAACCAC TTCACGGACC ATGTTGCACC
 29  V  T  G  P  W  K  G  D  V  N  L  P  C  T  Y  D  P  L  Q  G  Y  T  Q  V  L  V  K  W  L  V  Q  R  G

301 CTCTTCTGGA CTCTTCTGGA CTCTTCTGGA GACCATATCC AGCAGGCAAA GTACCAGGGC CGCCTGCATG TGAGCCACAA GGTTCCAGGA
    GAGTCTGGA CAGTGGATAGG AGAGACACCT CTGGTATAGG TCGTCCGTTT CATGGTCCCG GCGGACGTAC ACTCGGTGTT CCAAGGTCCT
 62  S  D  P  V  T  I  F  L  R  D  S  S  G  D  H  I  Q  Q  A  K  Y  Q  G  R  L  H  V  S  H  K  V  P  G

401 GATGATCGCC TCCAATTGAG CACCCTGGAG ATGGATGACC GGAGCCACTA CACCGAGGTG ACAGACTGGCAG CCACTGGACCT TCTCAGGACT ACCGTTGGTT CAGCACTCTC
    CTACTAGCGG AGTTAACTC GTGGGACCTC TACCTACTGG CCTCGGTGAT CTGGATATTC TGGTCACACTT GTCCACACGTT GGTGACCGACTGA AGTCGTGAGAC
 95  D  V  S  L  Q  L  S  T  L  E  M  D  D  R  S  H  Y  T  C  E  V  T  W  Q  T  P  D  G  N  Q  V  V  R  D

501 ATAAGATTAC TGAGCTCCGT GTCCAGAAAC TCTCTGTCTC CAAGCCCACA GTTCGGGTGT GCAGCAGGGTTA TGGCTTCACG ACCGAAGTCC CACGGGGTCC GAATGAGGAT
    TATTCTAATG ACTCGAGGCA CAGGTCTTTG AGAGACAGAG GTTCGGGTGT CAAGCCCACA GTCCCCAAT ACCGAAGTGC CACGGGGTCC CTTACTCCTA
129  K  I  T  E  L  R  V  Q  K  L  S  V  S  K  P  T  V  T  T  G  S  G  Y  G  F  T  V  P  Q  G  M  R  I

601 TAGCCCTTCAA TGCCAGGCTC GGGGTTCTC TCCCATCAGT TATATTTGGT ATAAGCAACA GACTAATAAC CAGGAACCCA TCAAAGTAGC AACCCTAAGT
    ATCGGAAGTT ACGGTCCGAG CCCAAGAGG AGGGTAGTCA ATATAAACCA TATTCGTTGT CTGATTATTG GTCCTTGGGT AGTTTCATCG TTGGGATTCA
162  S  L  Q  C  Q  A  R  G  S  P  P  I  S  Y  I  W  Y  K  Q  Q  T  N  N  Q  E  P  I  K  V  A  T  L  S
```

FIG._6A

```
SEQ ID NO:7  701 ACCTTACTCT TCAAGCCTGC GGTGATAGCC GACTCAGGCT CCTATTTCTG CACTGCCAAG GGCCAGGTTG GCTCTCAGCA GCACAGGCAC ATTGTGAAGT
                 TGGAATGAGA AGTTCGGACG CCACTATCCG CTGAGTCCGA GGATAAAGAC GTGACGGTTC CCGGTCCAAC CGAGACTCGT CGTGTCCGTG TAACACTTCA
SEQ ID NO:2  195  T  L  L  F   K  P  A  V   I  A  D  S   G  S  Y  F   C  T  A  K   G  Q  V  G   S  E  Q  H   S  D  I  V   K  F

801 TTGTGGTCAA AGACTCCTCA AAGCTACTCA AGACCAAGAC TGAGGCCACT ACAACCATGA CATACCCCTT GAAAGCAACA TCTACAGTGA AGCAGTCCTG
                 AACACCAGTT TCTGAGGAGT TTCGATGAGT TCTGGTTCTG ACTCCGGTGA TGTTGGTACT GTATGGGGAA CTTTCGTTGT AGATGTCACT TCGTCAGGAC
             229  V  V  K  D   S  S  K  L   L  K  T  K   T  E  A  P   T  T  M  T   Y  P  L  K   A  T  S  T   V  K  Q  S   W

901 GGACTGGACC ACTGACATGG ATGGCTACCT TGGAGAACCT AGTGCTGGGC CAGGAAAGAG CCTGCCTGTC TTTGCCATCA TCCTCATCAT CTCCTTGTGC
                 CCTGACCTGG TGACTGTACC TACCGATGGA ACCTCTTGGA TCACGACCCG GTCCTTTCTC GGACGGACAG AAACGGTAGT AGGAGTAGTA GAGGAACACG
             262  D  W  T  T   D  M  D  G   Y  L  G  E   T  S  A  G   P  G  K  S   L  P  V  F   A  I  I  L   I  I  S  L   C

1001 TGTATGGTGG TTTTTACCAT GGCCTATATC ATGCTCTGTC GGAAGACATC CCAACAAGAG GGTGTTCTC GTACAGATGC TTCGTCCGTC CATTCTTTCA GAGAGAA
                 ACATACCACC AAAAATGGTA CCGGATATAG TACGAGACAG CCTTCTGTAG GGTTGTTCTC CCACAAGAG CATGTCTACG AAGCAGGCAG GTAAGAAAGT CTCTCTTCTT
             295  C  M  V  V   F  T  M  A   Y  I  M  L   C  R  K  T   S  Q  Q  E   H  V  Y  E   A  A  R  Q

1101 CCATTTTGA CCCGTCCT GCCCTCAATT TTGATTACTG GCAGGAAATG TGGAGGAAGG ACAGACCCAA TCCTAAGGCC GGAGGCCTTC
                 GGTAAAACT GGGCAGGA CGGGAGTTAA AACTAATGAC CGTCCTTTAC ACCTCCTTCC TGTCTGGGTT AGGATTCCGG CCTCCGGAAG

1201 AGGGTCAGGA CATAGCTGCC TTCCCTCT CAGGCACCT CTGAGGTTGT TTTGGCCCTC TGAACACAAA GGATAATTTA GATCCATCTG CCTTCTGCTT
                 TCCCAGTCCT GTATCGACGG AAGGGAGAGA GTCCGTGGAA GACTCCAACA AAACCGGGAG ACTTGTGTTT CCTATTAAAT CTAGTAGAC GGAAGACGAA

1301 CCAGAATCCC TGGGTGGTAG GATCCTGATA ATTAATTCGG AGAGAGGCCA ACGACTCTGG GGGAAACCAG AGGTGGCCA TCTTCCAAG TGGCTGCTCG TCTTATGGT
                 GGTCTTAGGG ACCCACCATC CTAGGACTAT TAATTAAGCC TCTCTCCGGT TGCTGAGACC TCCTTGGTC CTGGTGTCGG GGTTCAGGA AGAACCGGT AGATACCCA

1401 GGTGGGCTCT TGGGCCATAG ACCGGTATC CCGTGTACGG AGAAACCATG TCCTTTGGTAC CAGGAGTACC TGCCTGATAGC CTGGATCATC AGTGATGAGC
                 CCACCCGAGA ACCCGGATA GGCCATATG GGCACATGCC TCTTTGGTAC AGAAGGCTTC ACCGACGAGG TCACTACTCG

1501 CAACTTCCCA GAATCTGGGC AACAACTACT CTGATGAGCC CTGCATAGGA CAGGAGTACC GTCCTAGTTA CCGTTGATGC CCCGCTGCT CCCGCTGCT GGGCGACGA
                 GTTGAAGGGT CTTAGACCCG TTGTTGATGA GACTACTCGG GACGTACCT GTCCTCATGG GACGATCAAG TCTAGTAGCG CCGATCAAT GGCAACTACG CCCGCTGCT GGGGGACGA
```

*FIG._6B*

SEQ ID NO:7

```
1601 GGACACAGTT CCTCTGCATT ATGAGTTTCT GGCCACTGAG GGCAAAAGTG TCTGTTAAAA ATGCCCCATT AGGCCAGGAT CTGCTGACAT AATTGCCTAG
     CCTGTGTCAA GGAGACCTAA TACTCAAAGA CCGGTGACTC CCGTTTTCAC AGACAATTTT TACGGGGTAA TCCGGTCCTA GACGACTGTA TTAACGGATC

1701 TCAGTCCTTG CCTTCTGCAT GGCCTTCTTC CCTGCTACCT CTCTTCCTGG ATAGCCCAAA GTGTCCGCCT ACCAACACTG GAGCCGGTGG GAGTCACTGG
     AGTCAGGAAC GGAAGACGTA CCGGAAGAAG GGACGATGGA GAGAAGGACC TATCGGGTTT CACAGGCCGA TGGTTGTGAC CTCGGCCACC CTCAGTGACC

1801 CTTTGCCCTG GAATTGCCA GATCCATCTC AAGTAAGCCA GCTGCTGGAT TTGGCTCTGG CCCCTTCTAG TATCCTGCC GGGGGCTTCT GGTACTCCTC
     GAAACGGGAC CTTAAACGGT CTAGCTAGAG TTCATTCGGT CGACGACCTA AACCGAGACC CGGGAAGATC ATAGAGACGG CCCCCGAAGA CCATGAGGAG

1901 TCTAAATACC AGAGGGAAGA TGCCCATAGC ACTAGGACTT GGTCATCATG CCTACAGACA CTATTCAACT TTGGCATCTT GCCACCAGAA GACCCGAGGG
     AGATTTATGG TCTCCCTTCT ACGGGTATCG TGATCCTGAA CCAGTAGTAC GGATGTCTGT GATAAGTTGA AACCGTAGAA CGGTGGTCTT CTGGGCTCCC

2001 AGGCTCAGT CTGCCTCAGT AGAGGAGAG TGCCAGAGTC AGAGGACCAG CTATATCCAG GATCATTTCT CTTTCTTCAG GGCCAGACAG CTTTTAATTG TTCACAGGCC
     TCCGAGTCGA GACGGTCGA TCTCCTGGTC GATATAGGTC CTAGTAAGA GAAAGAAGTC CCGGTCTGTC GAAAATTAAC TTTAACAATA AAGTGTCCGG

2101 AGGGTTCAGT TCTGCCTCTC CACTATAAGT GACTCTCTCC TGGTGCTCA TAAATATCTA ATCATAACAG C
     TCCCAAGTCA AGACGAGGAG GTGATATTCA GATTACAAGA ACCACGAGTT ATTTATAGAT TAGTATTGTC G
```

FIG._6C

SEQ ID NO:8

CCCAGAAGTTCAAGGGCCCCCGGCCTCCTGCGCTCCTGCCGCCGGGACCCTCGACCTCCT
CAGAGCAGCCGGCTGCCGCCCCGGGAAGATGGCGAGCAGGAGCCGCCACCGCCTCCTCCT
GCTGCTGCTGCGCTACCTGGTGGTCGCCCTGGGCTATCATAAGGCCTATGGGTTTTCTGC
CCCAAAAGACCAACAAGTAGTCACAGCAGTAGAGTACCAAGAGGCTATTTTAGCCTGCAA
AACCCCAAAGAAGACTGTTTCCTCCAGATTAGAGTGGAAGAAACTGGGTCGGAGTGTCTC
CTTTGTCTACTATCAACAGACTCTTCAAGGTGATTTTAAAAATCGAGCTGAGATGATAGA
TTTCAATATCCGGATCAAAAATGTGACAAGAAGTGATGCGGGGAAATATCGTTGTGAAGT
TAGTGCCCCATCTGAGCAAGGCCAAAACCTGGAAGAGGATACAGTCACTCTGGAAGTATT
AGTGGCTCCAGCAGTTCCATCATGTGAAGTACCCTCTTCTGCTCTGAGTGGAACTGTGGT
AGAGCTACGATGTCAAGACAAAGAAGGGAATCCAGCTCCTGAATACACATGGTTTAAGGA
TGGCATCCGTTTGCTAGAAAATCCCAGACTTGGCTCCCAAAGCACCAACAGCTCATACAC
AATGAATACAAAAACTGGAACTCTGCAATTTAATACTGTTTCCAAACTGGACACTGGAGA
ATATTCCTGTGAAGCCCGCAATTCTGTTGGATATCGCAGGTGTCCTGGGAAACGAATGCA
AGTAGATGATCTCAACATAAGTGGCATCATAGCAGCCGTAGTAGTTGTGGCCTTAGTGAT
TTCCGTTTGTGGCCTTGGTGTATGCTATGCTCAGAGGAAAGGCTACTTTTCAAAAGAAAC
CTCCTTCCAGAAGAGTAATTCTTCATCTAAAGCCACGACAATGAGTGAAAATGTGCAGTG
GCTCACGCCTGTAATCCCAGCACTTTGGAAGGCCGCGGCGGGCGGATCACGAGGTCAGGA
GTTCTAGACCAGTCTGGCCAATATGGTGAAACCCCATCTCTACTAAAATACAAAATTAG
CTGGGCATGGTGGCATGTGCCTGCAGTTCCAGCTGCTTGGGAGACAGGAGAATCACTTGA
ACCCGGGAGGCGGAGGTTGCAGTGAGCTGAGATCACGCCACTGCAGTCCAGCCTGGGTAA
CAGAGCAAGATTCCATCTCAAAAAATAAAATAAATAAATAAATAAATACTGGTTTTTACC
TGTAGAATTCTTACAATAAATATAGCTTGATATTC

FIG.—7

SEQ ID NO:9

MARRSRHRLLLLLLRYLVVALGYHKAYGFSAPKDQQVVTAVEYQEAILACKTPKKTVSSR
LEWKKLGRSVSFVYYQQTLQGDFKNRAEMIDFNIRIKNVTRSDAGKYRCEVSAPSEQGQN
LEEDTVTLEVLVAPAVPSCEVPSSALSGTVVELRCQDKEGNPAPEYTWFKDGIRLLENPR
LGSQSTNSSYTMNTKTGTLQFNTVSKLDTGEYSCEARNSVGYRRCPGKRMQVDDLNISGI
IAAVVVVALVISVCGLGVCYAQRKGYFSKETSFQKSNSSSKATTMSENVQWLTPVIPALW
KAAAGGSRGQEF

FIG.—11

SEQ ID NO:5

```
  1 GCAGGCAAAG TACCAGGGCC GCCTGCATGT GAGCCACAAG GTTCCAGGAG ATGTATCCCT CCAATTGAGC ACCCTGGAGA TGGATGACCG GAGCCACTAC
    CGTCCGTTTC ATGGTCCCGG CGGACGTACA CTCGGTGTTC CAAGGTCCTC TACATAGGGA GGTTAACTCG TGGGACCTCT ACCTACTGGC CTCGGTGATG
                                                                                                ^42257.p1  SEQ ID NO:22
                                                                       ^42257.f1 SEQ ID NO:18

101 ACGTGTGAAG TCACCTGGCA GACTCCTGAT GGCAACCAAG TCGTGAGAGA TAAGATTACT GACCTCCGTG TCCAGAAACT CTCTGTCTCC AAGCCCACAG
    TGCACACTTC AGTGGACCGT CTGAGGACTA CCGTTGGTTC AGCACTCTCT ATTCTAATGA CTGGAGGCAC AGGTCTTTGA GAGACAGAGG TTCGGGTGTC

201 TGACAACTGG CAGGGGTTAT GGCTTCACGG TGCCCCAGGG AATGAGGATT AGCCTTCAAT CCCAAGGTTC CGGGTTCTCC TCCCATCAGT TATATTTGGT
    ACTGTTGACC GTCCCCAATA CCGAAGTGCC ACGGGGTCCC TTACTCCTAA TCGGAAGTTA CGGGTTCCAAG GCCCAAGAGG AGGGTAGTCA ATATAACCA

301 ATAAGCAACA GACTAATAAC CAGGAACCC ATCAAAGTAG CAACCCTAAG TACCTTACTC TTCAAGCCTG AAGTTCGGAC GCCACTATCG TCCTATTTCT
    TATTCGTTGT CTGATTATTG GTCCCTTGGG TAGTTTCATC GTTGGGATTC ATGGAATGAG AAGTTCGGAC TTCAAGCCTG CTGAGTCCG AGGATAAGA

401 GCACTGCCAA GGGCCAGGTT GGCTCTGAGC AGCACAGGGA CATTGTGAAG TTTGTGGTCA AAGCACTCCT AAGACCAAGA CTGAGGCACC
    CGTGACGGTT CCCGGTCCAA CCGAGACTCG TCGTGTCCCT GTAACACTTC AAACACCAGT TTCGATGAG CTTAAGGAG TTCTGGTTCT GACTCCGTGG
                                           ^42257.r1 SEQ ID NO:20

501 TACACCATG ACATACCCCT TGAAAGCAAC ATCTACAGTG AAGCAGTCCT GGGACTGGAC CACTGACATG GATGGCTACC TTGGAGACAC CAGTGCTGGG
    ATGTGGTAC TGTATGGGGA ACTTTCGTTG TAGATGTCAC TTCGTCAGGA CCCTGACCTG GTGACTGTAC CTACCGATGG AACCTCTCTG GTCACGACCC

601 CCAGGAAAGA GCCTGCCTGT CTTTGCCATC ATCCTCATCA TCTCCCTTGT GTGTATGGTG GTTTTTACCA TGGCCTATAT CATGCTCTGT CGGAAGACAT
    GGTCCTTTCT CGGACGGACA GAAACGGTAG TAGGAGTAGT AGAGGGAACA CACATACCAC CAAAAATGGT ACCGGATATA GTACGAGACA GCCTTCTGTA
                                                                                            ^42257.f2 SEQ ID NO:19

701 CCCAACAAGA GCATGCTCTAC GAAGCAGCCA GGGCACATGC CAGAGAGGCC GAGAAACCAT GAGGGTGGCC ATCTTCGCAA GTGGCTGCTC
    GGGTTGTTCT CGTACGAGATG CTTCGTCGGT CCCGTGTACG GTCTCTCCGG CTCTTTGGTA CTCCCACCGG TAGAAGCGTT CACCGACGAG
```

FIG._9A

SEQ ID NO:5

```
 801 CAGTGATGAG CCAACTTCCC AGAATCTGGG GCAACAACTA CTCTGATGAG CCCTGCATAG GACAGGAGTA CCAGATCATC GCCCAGATCA ATGGCAACTA
     GTCACTACTC GGTTGAAGGG TCTTAGACCC CGTTGTTGAT GAGACTACTC CTGTCCTCAT GGTCCTAGTA CGGGTCTAGT TACCGTTGAT
 901 CGCCCGCCCTG CTGGACACAG TTCCTCTGGA TTATGAGTTT CTGGCCACTG AGGGCAAAAG TGTCTGTTAA AAATGCCCCA TTAGGCCAGG ATCTGCTGAC
     GCGGGGCGGAC GACCTGTGTC AAGGAGACCT AATACTCAAA GACCGGTGAC TCCCGTTTTC ACAGACAATT TTTACGGGGT AATCCGGTCC TAGACGACTG
1001 ATAATTGCCT AGTCAGTCCT TGCCTTCTCG ATGGCCTTCT CCCTGCTAC CTCTCTTCCT GGATAGCCCA AAGTGTCCGC CTACCAACAC TGGAGCCCGCT
     TATTAACGGA TCAGTCAGGA ACGGAAGACG TACCGGAAGA AGGGACGATG GAGAGAAGGA CCCTATCGGGT TTCACAGGCG GATGGTGTG ACCTCGGGCGA
1101 GGGAGTCACT GGCTTTGCCC TGGAATTTGC CAGATGCATC TCAAGTAAGC CAGCTGCTGG ATTTGGCTCT TAAACCGAGA CCCGGGAAGA TCATAGAGAC GCCCGGGCTT
     CCCTCAGTGA CCGAAACGGG ACCTTAAACG GTCTACGTAG AGTTCATTCG GTCGACGACC TAAACCGAGA CCCGGGAAGA TCATAGAGAC GCCCCCCGAA
                                                                 ^42257.r2  SEQ ID NO:21
1201 CTGGTACTCC TCTCTAAATA CCAGAGGGAA GATGCCCATA GCCACTAGGAC TTGGTCATCA TGCCTACAGA CACTATTCAA CTTTGGCATC TTGCCACCAG
     GACCATGAGG AGAGATTTAT GGTCTCCCTT CTACGGGTAT CGTGATCCTG AACCAGTAGT ACGGATGTCT GTGATAAGTT GAAACCGTAG AACGGTGGTC
1301 AAGACCCGAG GGGAGGCTCA GCTCTGCCAG CTCAGAGACC CAGCTATATC CAGGATCATT TCTCTTTCTT CAGGGCCAGA CAGCTTTTAA TTGAAATTGT
     TTCTGGGCTC CCCTCCGAGT CGAGACGGTC GAGTCTCCTG GTCGATATAG AGTCCTAGTAA AGAGAAAGAA GTCCCGGTCT GTCGAAAATT AACTTTAACA
1401 TATTTCACAG GCCAGGGTTC AGTTCTGCTC CTCCACTATA AGTCTAAATGT TCTGACTCTC TCCTGGTGCT CAATAAATAT CTAATCATAA CAGCAAAAAA
     ATAAAGTGTC CGGTCCCAAG TCAAGACGAG GAGGTGATAT TCAGATTACA AGACTGAGAG AGGACCACGA GTTATTTATA GATTAGTATT GTCGTTTTTT
1501 AAA
     TTT
```

*FIG._9B*

|  | FRAME | SCORE | MATCH | PCT |
|---|---|---|---|---|
| A33_HUMAN  A33 ANTIGEN PRECURSOR - HOMO SAPIENS | +1 | 246 | 81 | 30 |

A33_HUMAN - A33 ANTIGEN PRECURSOR - HOMO SAPIENS (319 aa)
SCORE = 246 (86.6 BITS), EXPECT = 2.8e-19, P = 2.8e-19
IDENTITIES = 81/268 (30%), POSITIVES = 131/268 (48%), AT 121,17, FRAME = +1

```
DNA40628      121 LALGSVTVHSSEPEVRIPENNPVKLSCAYSGFSSPR---VEW-KFDQGDTTRLVC--YNN
SEQ ID NO:23        .  .*   .    *       *  *    *  .*.    .*.*..*   .*
A33_human      17 VTVDAISVETPQDVLRASQGKSVTLPCTYHTSTSSREGLIQWDKLLLTHTERVVIWPFSN
SEQ ID NO:24

DNA40628      283 K--ITAS-YEDRVTFL-------PTGITFKSVTREDTGTYTCMVS---EEGGNSYGEVKVK
                   *  * . *  *.*.*        **  *   * * .* *     **.     .*.
A33_human      77 KNYIHGELYKNRVSISNNAEQSDASITIDQLTMADNGTYECSVSLMSDLEGNT--KSRVR DNA40628      427 LIVLVPPSKPTVNIPSSATIGNRAVLTCSEQDGSPPSEYTWFKDGIVMPTNPKSTRAFSN
                   .******       .*  . *     ..*   * * .*.   *
A33_human     135 LLVLVPPSKPECGIEGETIIGNNIQLTCQSKEGSPTPQYSWKRYNILNQEQP-------

DNA40628      607 SSYVLNPTTGELV-FDPLSASDTGEYSCEARNGYGTPMTSNAVRMEAVERNVGV---IVA
                     *  *.  *    .*.   .**.* ****     .**  *    .  **   .  *
A33_human     187 ---LAQPASGQPVSLKNISTDTSGYYICTSSNEEGTQFCNITVAVRSPSMNVALYVGIAV DNA40628      775 AVLVTLILLGILVFGIWFAYSRGHFDRT--KKGTSSKKVIYSQP
                   *. *  .**..     *      .   *  *.     *  *
A33_human     244 GVVAALIIIGIIIY----CCCCRGKDDNTEDKEDARPNREAYEEP
```

FIG._10A

SCORE = 245 (86.2 BITS), EXPECT =3.6e-19, P = 3.6e-19
IDENTITIES = 83/273 (30%), POSITIVES = 131/273 (47%), AT 112,12, FRAME = +1

```
DNA40628     112 LCSL--ALGSVTVHSSEPEVRIPENNPVKLSCAYSGFSSPR---VEW-KFDQGDTTRLVC
SEQ ID NO:25     **.:  . :::..* .   . *  .       *   ..*    * .*
A33_human     12 LCAVRVTVDAISVETPQDVLRASQGKSVTLPCTYHTSTSSREGLIQWDKLLLTHTERVVI
SEQ ID NO:26

DNA40628     274 --YNNK--ITAS-YEDRVTFL------PTGITFKSVTREDTGTYTCMVSEEGGNSYGEVK
                   .**   *:.  *..*:          ** . ** **  *  * ** .      *
A33_human     72 WPFSNKNYIHGELYKNRVSISNNAEQSDASITIDQLTMADNGTYECSVSLMS-DLEGNTK DNA40628     421 --VKLIVLVPPSKPTVNIPSSATIGNRAVLTCSEQDGSPPSEYTWFKDGIVMPTNPKSTR
                   *.*:*:******  .   .      *   .**  *. .  .    *
A33_human    131 SRVRLLVLVPPSKPECGIEGETIIGNNIQLTCQSKEGSPTPQYSWKRYNILNQEQP----

DNA40628     595 AFSNSSYVLNPTTGELV-FDPLSASDTGEYSCEARNGYGTPMTSNAVRMEAVERNVGV--
                           .    *  ** **     ..*:* *  ..  ..  *  ..*
A33_human    187 ------LAQPASGQPVSLKNISTDTSGYYICTSSNEEGTQFCNITVAVRSPSMNVALYV DNA40628     766 -IVAAVLVTLILLGILVFGIWFAYSRGHFDRT--KKGTSSKKVIYSQP
                  *. *:**:::   :.::..      ..*.    .*  *
A33_human    240 GIAVGVVAALIIGIIY---CCCCRGKDDNTEDKEDARPNREAYEEP
```

FIG._10B

```
SEQ ID NO: 6  A33_hum   1 .........MVGKMWPVLWT L CAVRVTVDAIS V ETPQDVLR ASQGKS V T L
SEQ ID NO: 1  40628     1 MGTKAQVERKLLCLFILAILCS..LALGSVT V HSSEPEVR I PENNP V K L A33_hum   42 PC T Y HTST S REGLIOWDK L LTHTERV V IWPFSNKNY I HGELY KNRVS I
              40628     49 SC A Y SGFS S PR...VEW.KF DQGDTTRL V C..YNNK..ITAS. Y EDRVTF A33_hum   92 SNNAEQSDAS I T I DQLT M A D NGTYEC S VSLMSDLEGNTKS R V R L L V L VPP
              40628     90 ..LPTG I TFKS V T R ED T GTYT C H V SEEGG.NSYGG N SYGE V K L I V L VPP A33_hum  142 SKPECG I EGETII GNN I Q LTCQSKE GS PT P QYS WKRYN I L NQEQP......
              40628    133 SKPTVN L PSSATI GNRAVL T C SEQDGS PP SE Y T WFKDG I VMPTN PK STRA A33_hum  187 ...LAQP A S G QPVSLKN I S T DTS G YY I CTSSNEE GT QFCN I T V AVRS
              40628    183 FSNSSYVLNP TT GE.LVFDPL S ASDT GE Y S CEARNGY GT PMTSNA V R M EA A33_hum  231 PSM NVALYVG I AVG V VAAL I I I G I I I YCC.CCRGKDDNTE DK EDARPNRE
              40628    232 VERNVGV...I VAA V LVT L I L L G I L VFGIWFAYSRGHFDRT K GTSSKKV A33_hum  280 A Y EEP PEQLRELSREREEEDDYRQEEQRSTGRESPQHLDQ
              40628    279 I Y SQ P SARSEGEFKQTSSFLV
```

FIG._12

```
SEQ ID NO: 6   A33_hum    1   MVGKMWPVLWTLCAVRVTVDAISVETPQDVLRASQGKSVTLPCTYHTSTS
SEQ ID NO: 2   45416      1   .MGILLGLLLLGHLTVDTIYGRPILEVPESVTGPWKG.DVNLPCTYDPLQG A33_hum    51  SREGLIQWDKLLTHTERVVIW.PFSNKNYIHGELYKNRVSISNNAEQSD
               45416      49  YTQVLVKW..LVQRGSDPVTIFLRDSSGDHVQQAKYQGRLHVSHKV.PGD A33_hum   100  ASITIDQLTWADNGTYECSVS.LMSDLEGNTKSRV.....RLLVLVPPS
               45416      96  VSLQLSTLEWDDRSHYTCEVTWQTPDGNQVVRDKITELRVQKLSVSKPTV A33_hum   143  KPECGIEGETIIGNNIQLTCQSKEGSPTPQYSWKRYNILNQEQPLAQPAS
               45416     146  TTGSGYGFTVPQGMR.IS.LQCQAR.GSPPISY.W..YKQQTNNEPIKVAT A33_hum   193  GQPVSLKNISTDTSGYYICTSSNEEGT.QFCNI.TVAVRSPSMNVALYVG
               45416     193  LSTLLFKPAVIADSGSYFCTAKGQVGSEQHSDIVKFVVKDSKLLKTKTE A33_hum   241  IAVGVVAALIIIGILIYCCCCRGKDQNTEDKEDARPNREAYEEPPEQLRE
               45416     243  APTTMTYPLKATSTVKQSWDWTTDWDGYLGETSAGPGKSLPVFAILLIS A33_hum   291  SREREEEDDYRQEEQRSTGRESPDHLDQ
               45416     293  LCCHVVFTHAYIMLCRKTSQQEHVYEAAR
```

FIG._13

```
SEQ ID NO: 6  A33_hum    1   ..MVGKMWPVLWTLCAVRVTVD....AISVETPQDVLRASQGKSVTLPC
SEQ ID NO: 9  35638      1   MARRSRHRLLLLRYLVVALGYHKAYGFSAPKDQQVTAVEYQEAILAC A33_hum   44   TYHTSTSSREGLIQMDKLLTHTERVVIWPFSNKNYIHGELYKNVSISN
              35638     51   ..KTPKKTVSSRLEWKKL.....GRSVSFVYYQQT.LQGD.FKNR...

A33_hum   94   NAEQSDASIT.IDQLTMADNGTYECSVSLMSDLEGN.TKSRVRLLVPPS
              35638     87   .AEMIDFNJRIKNVTRSDAGKYRCEVSAPSEQGQNLEEDTVTLEVLVAPA A33_hum  143   KPECGIEGETIIGNNIQLTCQSKEGSPTPQYSWKRYNILNQEQPLAQPAS
              35638    136   VPSCEVPSSALSGTVVELRCQDKEGNPAPEYTWFKDGIRLLENPRLGSQS A33_hum  193   GQPVSLKNIST.DTSGYYICTSSNEEGTQFCNITVAV...RSPSMNVALYV
              35638    186   TNSSYTMNTKTGTLQFNT.VSKLDTGEYSCEARNSVGYRRCPGKRMQVDD A33_hum  240   GIAVGVVAALIIIGIIIYCC...CRGKDDNTEDKEDARPNREAYEEPPE
              35638    235   LNISGIIAAVVVVALVISVCGLGVCYAQRKGYFSKETSFQKSNSSKATT A33_hum  287   QLRELSR.EREEEDDYRQEEQRSTGRESPDHLDQ
              35638    285   MSENVQWLTPVIPALWKAAAGGSRGQEF
```

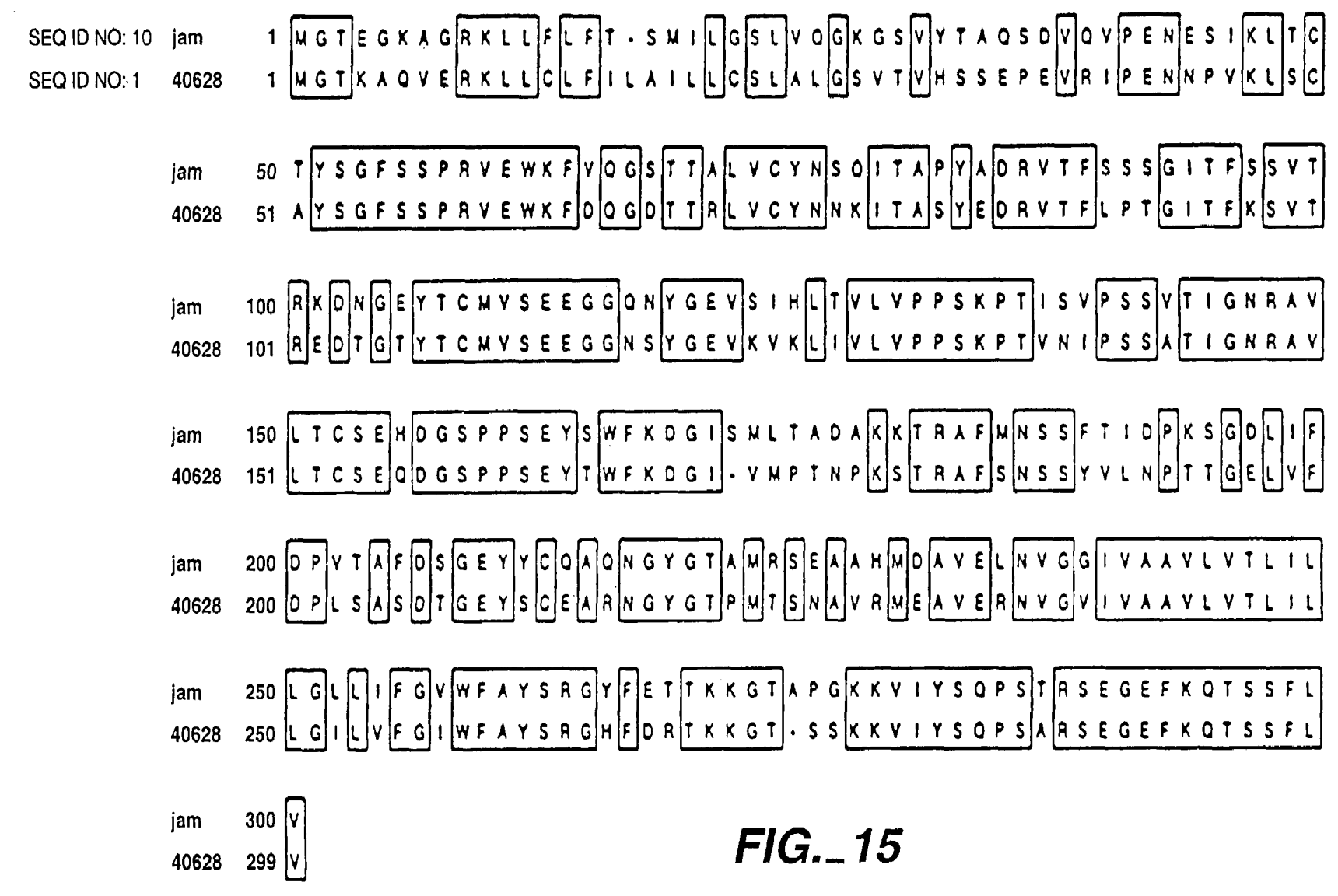

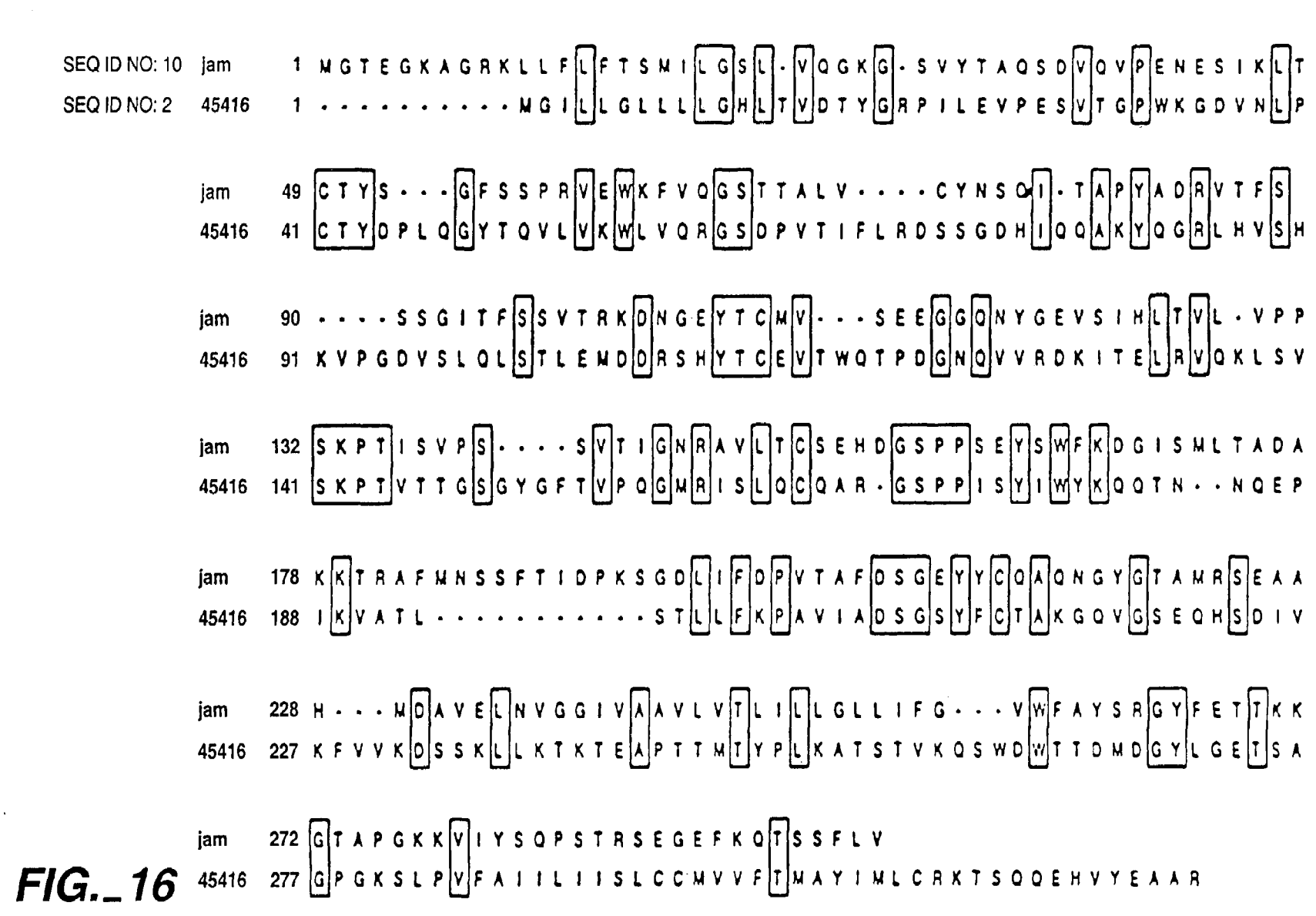

```
SEQ ID NO: 10   jam       1  MGTEGKAGRK LLFTSWILGS LVQGKGSVYT AQSDVQV... PENESIKL
SEQ ID NO: 29   35638     1  ..NARRSRHR LLLRYLVVAL GYHKAYGFS APKDQVTAVE YQEAIL jam      48  TC.TYSGFSS PRVEWKFVQG STTALVCYNS QITAPYADRV TFSSSGITFS
                35638    49  ACKTPKKTVS RLEWKKL.GR SVSFVYYQQT LQGDFKNRAE MIDFNIRIK jam      97  SVTRKDNGEY TCMVS..EEG GQNYGEVSIH LTVPPSKPTI SVPSSVTI
                35638    98  NVTRSDAGKY RCEVSAPSEQ GQNLEEDTVT LEVLVAPVPA SCEVPSSALS jam     145  GNRAVLTCSE HDGSPPSEYS WFKDGISMLT ADAKKTRAFM NSSFTIDPKS
                35638   148  GTVVELRCQD KEGNPAPEYT WFKDGIRLL. ENPRLGSQST NSSYTMNTKT jam     195  GQLIFDPVTA FDSGEYYCQA QNGYGTAMRS EAAHMDAVEL NVGGIVAAVL
                35638   197  GTLQFNTVSK LDTGEYSCEA RNSVG.YRRC PGKRMQVDDL NISGIIAAVV jam     245  VTLILLGLLI FGVWFAYSRG YFETTKKGTA PGKKVIYSQP STRSEGEFKQ
                35638   246  VALVISVCGL GVCYAQRKGYF... SKETSFQKSN SSKATTMSEN VQWL jam     295  TSSFLV
                35638   293  TPVIPALWKA AAGGSRGQEF
```

*FIG._17*

```
SEQ ID NO: 6    A33_hum    1    ......MVGKHWPVLWT·LCAVRVTVDAISVETPQDVLRASQGKSVTLPCT
SEQ ID NO: 10   jam        1    MGTEGKAGRKLLFLSMILGSLVQGKGSVTAQSDVQVPENESIKLTCT A33_hum    45   YHTSTSREGLIQWDKLLLTHTERVVIWPFSNKNYIHGELYKNRVSISNN
                jam        51   YSGFSSPR...VEW·KFVQGSTTALVC...YNSQ··ITAP·YADRVTFSS·

A33_hum    95   AEQSDAS·ITIDQLTMADNGTYECSVSLMSDLEGNTKSRVRLLVPPSKP
                jam        91   ...SGITFSSVTRKDNGEYTCMVSEEGG·QNYGEVSIHLTLVPPSKP A33_hum    145  ECGIEGETIIGNNIQLTCQSKEGSPTPQYSWKRYNILNQEQPLAQPASGQ
                jam        135  TISVPSSVTIGNRAVLTCSEHDGSPPSEYYSWFKDGISMLTADAKKTRAFH A33_hum    195  PVSLKNISTDTSGYYICTSSNEEGTQFCN····ITVAVRSPSMN···VAL
                jam        185  NSSFTIDPKSGDLIFDPVTAFDSGEYYCQAQNGYGTAMRSEAAHMDAVEL A33_hum    238  YV·GIAVGVAAL··IGI··YC···CCCRGKDDNTEDKEDARPNREAYEE
                jam        235  NVGIVAAVLVTLI·ILLGLLFGVWFAYSRGYFE·ITKGTAPGKKVIYSQ A33_hum    284  PPEQLRELSREREEEDDYRQEEQRSTGRESPDHLDQ
                jam        284  PSTRSEGEFKQTSSFLV
```

*FIG._18*

| TISSUE | EXPRESSION | TISSUE | EXPRESSION | TISSUE | EXPRESSION |
|---|---|---|---|---|---|
| WHOLE BRAIN | + | HEART | ++ | KIDNEY | +++ |
| AMYGDALA | + | AORTA | + | LIVER | ++ |
| CAUDATE NUCLEUS | + | SKELETAL MUSCLE | +++ | SMALL INTESTINE | ++ |
| CEREBELLUM | − | COLON | ++ | SPLEEN | ++ |
| CEREBRAL CORTEX | + | BLADDER | + | THYMUS | ++ |
| FRONTAL LOBE | + | UTERUS | +++ | PERIPHERAL LEUKOCYTE | + |
| HIPPOCAMPUS | + | PROSTATE | +++ | LYMPH NODE | + |
| MEDULLA OBLONGATA | + | STOMACH | ++ | BONE MARROW | + |
| OCCIPITAL LOBE | + | TESTIS | +++ | | |
| PUTAMEN | + | OVARY | ++ | APPENDIX | + |
| SUSTANTIA NIGRA | + | PANCREAS | ++ | LUNG | ++++ |
| TEMPORAL LOBE | + | PITUITARY GLAND | ++ | TRACHEA | ++++ |
| THALAMUS | + | ADRENAL GLAND | ++ | PLACENTA | ++++ |
| NUCLEUS ACCUMBEUS | + | THYROID GLAND | +++ | | |
| SPINAL CORD | − | SALIVARY GLAND | ++ | FETAL BRAIN | + |
| | | MAMMARY GLAND | ++ | FETAL HEART | + |
| | | | | FETAL KIDNEY | ++ |
| | | | | FETAL LIVER | +++ |
| | | | | FETAL SPLEEN | + |
| | | | | FETAL LUNG | ++++ |

FIG._19

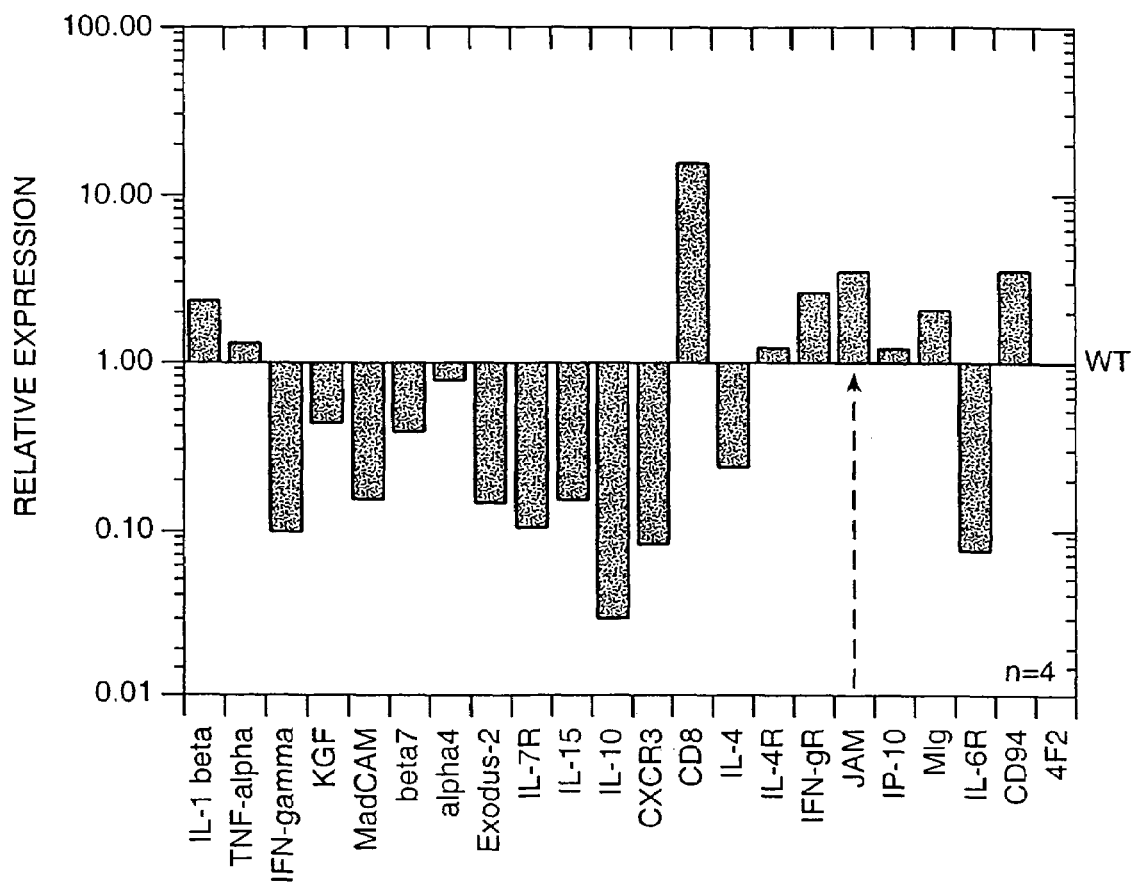
FIG._20
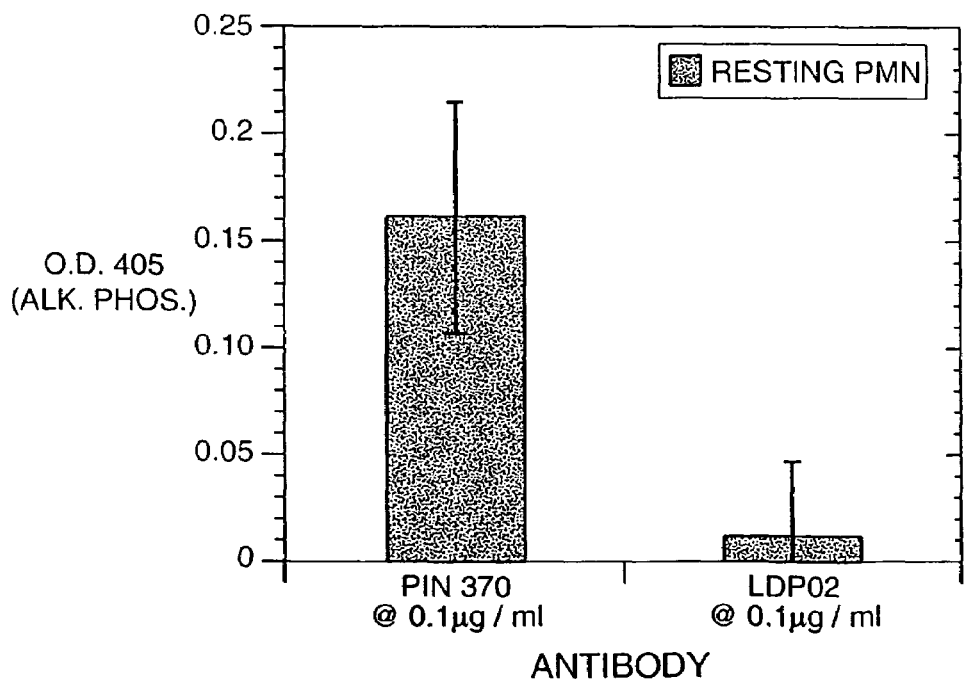
FIG._21

SEQUENCE LISTING

<160> NUMBER OF SEQ ID NOS: 30

<210> SEQ ID NO 1
<211> LENGTH: 299
<212> TYPE: PRT
<213> ORGANISM: Homo sapiens

<400> SEQUENCE: 1

```
Met Gly Thr Lys Ala Gln Val Glu Arg Lys Leu Leu Cys Leu Phe
 1               5                  10                  15

Ile Leu Ala Ile Leu Leu Cys Ser Leu Ala Leu Gly Ser Val Thr
                20                  25                  30

Val His Ser Ser Glu Pro Glu Val Arg Ile Pro Glu Asn Asn Pro
                35                  40                  45

Val Lys Leu Ser Cys Ala Tyr Ser Gly Phe Ser Ser Pro Arg Val
                50                  55                  60

Glu Trp Lys Phe Asp Gln Gly Asp Thr Thr Arg Leu Val Cys Tyr
                65                  70                  75

Asn Asn Lys Ile Thr Ala Ser Tyr Glu Asp Arg Val Thr Phe Leu
                80                  85                  90

Pro Thr Gly Ile Thr Phe Lys Ser Val Thr Arg Glu Asp Thr Gly
                95                  100                 105

Thr Tyr Thr Cys Met Val Ser Glu Glu Gly Gly Asn Ser Tyr Gly
                110                 115                 120
```

-continued

```
Glu Val Lys Val Lys Leu Ile Val Leu Val Pro Pro Ser Lys Pro
            125                 130                 135

Thr Val Asn Ile Pro Ser Ser Ala Thr Ile Gly Asn Arg Ala Val
            140                 145                 150

Leu Thr Cys Ser Glu Gln Asp Gly Ser Pro Pro Ser Glu Tyr Thr
            155                 160                 165

Trp Phe Lys Asp Gly Ile Val Met Pro Thr Asn Pro Lys Ser Thr
            170                 175                 180

Arg Ala Phe Ser Asn Ser Ser Tyr Val Leu Asn Pro Thr Thr Gly
            185                 190                 195

Glu Leu Val Phe Asp Pro Leu Ser Ala Ser Asp Thr Gly Glu Tyr
            200                 205                 210

Ser Cys Glu Ala Arg Asn Gly Tyr Gly Thr Pro Met Thr Ser Asn
            215                 220                 225

Ala Val Arg Met Glu Ala Val Glu Arg Asn Val Gly Val Ile Val
            230                 235                 240

Ala Ala Val Leu Val Thr Leu Ile Leu Leu Gly Ile Leu Val Phe
            245                 250                 255

Gly Ile Trp Phe Ala Tyr Ser Arg Gly His Phe Asp Arg Thr Lys
            260                 265                 270

Lys Gly Thr Ser Ser Lys Lys Val Ile Tyr Ser Gln Pro Ser Ala
            275                 280                 285

Arg Ser Glu Gly Glu Phe Lys Gln Thr Ser Ser Phe Leu Val
            290                 295

<210> SEQ ID NO 2
<211> LENGTH: 321
<212> TYPE: PRT
<213> ORGANISM: Homo sapiens

<400> SEQUENCE: 2

Met Gly Ile Leu Leu Gly Leu Leu Leu Gly His Leu Thr Val
  1               5                  10                  15

Asp Thr Tyr Gly Arg Pro Ile Leu Glu Val Pro Glu Ser Val Thr
             20                  25                  30

Gly Pro Trp Lys Gly Asp Val Asn Leu Pro Cys Thr Tyr Asp Pro
             35                  40                  45

Leu Gln Gly Tyr Thr Gln Val Leu Val Lys Trp Leu Val Gln Arg
             50                  55                  60

Gly Ser Asp Pro Val Thr Ile Phe Leu Arg Asp Ser Ser Gly Asp
             65                  70                  75

His Ile Gln Gln Ala Lys Tyr Gln Gly Arg Leu His Val Ser His
             80                  85                  90

Lys Val Pro Gly Asp Val Ser Leu Gln Leu Ser Thr Leu Glu Met
             95                 100                 105

Asp Asp Arg Ser His Tyr Thr Cys Glu Val Thr Trp Gln Thr Pro
            110                 115                 120

Asp Gly Asn Gln Val Val Arg Asp Lys Ile Thr Glu Leu Arg Val
            125                 130                 135

Gln Lys Leu Ser Val Ser Lys Pro Thr Val Thr Thr Gly Ser Gly
            140                 145                 150

Tyr Gly Phe Thr Val Pro Gln Gly Met Arg Ile Ser Leu Gln Cys
            155                 160                 165

Gln Ala Arg Gly Ser Pro Pro Ile Ser Tyr Ile Trp Tyr Lys Gln
            170                 175                 180
```

```
Gln Thr Asn Asn Gln Glu Pro Ile Lys Val Ala Thr Leu Ser Thr
            185                 190                 195

Leu Leu Phe Lys Pro Ala Val Ile Ala Asp Ser Gly Ser Tyr Phe
            200                 205                 210

Cys Thr Ala Lys Gly Gln Val Gly Ser Glu Gln His Ser Asp Ile
            215                 220                 225

Val Lys Phe Val Val Lys Asp Ser Ser Lys Leu Leu Lys Thr Lys
            230                 235                 240

Thr Glu Ala Pro Thr Thr Met Thr Tyr Pro Leu Lys Ala Thr Ser
            245                 250                 255

Thr Val Lys Gln Ser Trp Asp Trp Thr Thr Asp Met Asp Gly Tyr
            260                 265                 270

Leu Gly Glu Thr Ser Ala Gly Pro Gly Lys Ser Leu Pro Val Phe
            275                 280                 285

Ala Ile Ile Leu Ile Ile Ser Leu Cys Cys Met Val Val Phe Thr
            290                 295                 300

Met Ala Tyr Ile Met Leu Cys Arg Lys Thr Ser Gln Gln Glu His
            305                 310                 315

Val Tyr Glu Ala Ala Arg
            320

<210> SEQ ID NO 3
<211> LENGTH: 390
<212> TYPE: DNA
<213> ORGANISM: Homo Sapien

<400> SEQUENCE: 3
cttcttgcca actggtatca ccttcaagtc cgtgacacgg gaagacactg            50
ggacatacac ttgtatggtc tctgaggaag gcggcaacag ctatggggag           100
gtcaaggtca agctcatcgt gcttgtgcct ccatccaagc ctacagttaa           150
catcccctcc tctgccacca ttgggaaccg ggcagtgctg acatgctcag           200
aacaagatgg ttccccacct tctgaataca cctggttcaa agatgggata           250
gtgatgccta cgaatcccaa agcacccgt gccttcagca actcttccta            300
tgtcctgaat cccacaacag agagctggt ctttgatccc ctgtcagcct            350
ctgatactgg agaatacagc tgtgaggcac ggaatgggta                      390

<210> SEQ ID NO 4
<211> LENGTH: 726
<212> TYPE: DNA
<213> ORGANISM: Homo Sapien

<400> SEQUENCE: 4
tctcagtccc ctcgctgtag tcgcggagct gtgttctgtt tcccaggagt            50
ccttcggcgg ctgttgtgct caggtgcgcc tgatcgcgat ggggacaaag           100
gcgcaagctc gagaggaaac tgttgtgcct cttcatattg cgatcctgt            150
tgtgctccct ggcattgggc agtgttacag ttgcactctt ctgaacctga           200
agtcagaatt cctgagaata atcctgtgaa gttgtcctgt gcctactcgg           250
gcttttcttc tccccgtgtg gagtggaagt ttgaccaagg agacaccacc           300
agactcgttt gctataataa caagatcaca gcttcctatg aggaccgggt           350
gaccttcttg ccaactggta tcaccttcaa gtccgtgaca cgggaagaca           400
```

| | |
|---|---|
| ctgggacata cacttgtatg gtctctgagg aaggcggcaa cagctatggg | 450 |
| gaggtcaagg tcaagctcat cgtgcttgtg cctccatcca agcctacagt | 500 |
| taacatcccc tcctctgcca ccattgggaa ccgggcagtg ctgacatgct | 550 |
| cagaacaaga tggttcccca ccttctgaat acacctggtt caaagatggg | 600 |
| atagtgatgc ctacgaatcc caaaagcacc cgtgccttca gcaactcttc | 650 |
| ctatgtcctg aatcccacaa caggagagct ggtctttgat cccctgtcag | 700 |
| cctctgatac tggagaatac agctgt | 726 |

<210> SEQ ID NO 5
<211> LENGTH: 1503
<212> TYPE: DNA
<213> ORGANISM: Homo Sapien

<400> SEQUENCE: 5

| | |
|---|---|
| gcaggcaaag taccagggcc gcctgcatgt gagccacaag gttccaggag | 50 |
| atgtatccct ccaattgagc accctggaga tggatgaccg gagccactac | 100 |
| acgtgtgaag tcacctggca gactcctgat ggcaaccaag tcgtgagaga | 150 |
| taagattact gagctccgtg tccagaaact ctctgtctcc aagcccacag | 200 |
| tgacaactgg cagcggttat ggcttcacgg tgccccaggg aatgaggatt | 250 |
| agccttcaat gccagggttc ggggttctcc tcccatcagt tatatttggt | 300 |
| ataagcaaca gactaataac cagggaaccc atcaaagtag caaccctaag | 350 |
| taccttactc ttcaagcctg cggtgatagc cgactcaggc tcctatttct | 400 |
| gcactgccaa gggccaggtt ggctctgagc agcacagcga cattgtgaag | 450 |
| tttgtggtca aagactcctc aaagctactc aagaccaaga ctgaggcacc | 500 |
| tacaaccatg acatacccct gaaagcaac atctacagtg aagcagtcct | 550 |
| gggactggac cactgacatg gatggctacc ttggagagac cagtgctggg | 600 |
| ccaggaaaga gcctgcctgt ctttgccatc atcctcatca tctccttgtg | 650 |
| ctgtatggtg gtttttacca tggcctatat catgctctgt cggaagacat | 700 |
| cccaacaaga gcatgtctac gaagcagcca gggcacatgc cagagaggcc | 750 |
| aacgactctg gagaaaccat gagggtggcc atcttcgcaa gtggctgctc | 800 |
| cagtgatgag ccaacttccc agaatctggg gcaacaacta ctctgatgag | 850 |
| ccctgcatag gacaggagta ccagatcatc gcccagatca atggcaacta | 900 |
| cgcccgcctg ctggacacag ttcctctgga ttatgagttt ctggccactg | 950 |
| agggcaaaag tgtctgttaa aaatgcccca ttaggccagg atctgctgac | 1000 |
| ataattgcct agtcagtcct tgccttctgc atggccttct tccctgctac | 1050 |
| ctctcttcct ggatagccca aagtgtccgc taccaacac tggagccgct | 1100 |
| gggagtcact ggctttgccc tggaatttgc cagatgcatc tcaagtaagc | 1150 |
| cagctgctgg atttggctct gggcccttct agtatctctg ccgggggctt | 1200 |
| ctggtactcc tctctaaata ccagagggaa gatgcccata gcactaggac | 1250 |
| ttggtcatca tgcctacaga cactattcaa ctttggcatc ttgccaccag | 1300 |
| aagacccgag gggaggctca gctctgccag ctcagaggac cagctatatc | 1350 |
| caggatcatt tctctttctt cagggccaga cagcttttaa ttgaaattgt | 1400 |
| tatttcacag gccagggttc agttctgctc ctccactata agtctaatgt | 1450 |

-continued

```
tctgactctc tcctggtgct caataaatat ctaatcataa cagcaaaaaa        1500
aaa                                                           1503
```

<210> SEQ ID NO 6
<211> LENGTH: 319
<212> TYPE: PRT
<213> ORGANISM: Homo sapiens

<400> SEQUENCE: 6

```
Met Val Gly Lys Met Trp Pro Val Leu Trp Thr Leu Cys Ala Val
 1               5                  10                  15

Arg Val Thr Val Asp Ala Ile Ser Val Glu Thr Pro Gln Asp Val
                20                  25                  30

Leu Arg Ala Ser Gln Gly Lys Ser Val Thr Leu Pro Cys Thr Tyr
                35                  40                  45

His Thr Ser Thr Ser Ser Arg Glu Gly Leu Ile Gln Trp Asp Lys
                50                  55                  60

Leu Leu Leu Thr His Thr Glu Arg Val Val Ile Trp Pro Phe Ser
                65                  70                  75

Asn Lys Asn Tyr Ile His Gly Glu Leu Tyr Lys Asn Arg Val Ser
                80                  85                  90

Ile Ser Asn Asn Ala Glu Gln Ser Asp Ala Ser Ile Thr Ile Asp
                95                  100                 105

Gln Leu Thr Met Ala Asp Asn Gly Thr Tyr Glu Cys Ser Val Ser
                110                 115                 120

Leu Met Ser Asp Leu Glu Gly Asn Thr Lys Ser Arg Val Arg Leu
                125                 130                 135

Leu Val Leu Val Pro Pro Ser Lys Pro Glu Cys Gly Ile Glu Gly
                140                 145                 150

Glu Thr Ile Ile Gly Asn Asn Ile Gln Leu Thr Cys Gln Ser Lys
                155                 160                 165

Glu Gly Ser Pro Thr Pro Gln Tyr Ser Trp Lys Arg Tyr Asn Ile
                170                 175                 180

Leu Asn Gln Glu Gln Pro Leu Ala Gln Pro Ala Ser Gly Gln Pro
                185                 190                 195

Val Ser Leu Lys Asn Ile Ser Thr Asp Thr Ser Gly Tyr Tyr Ile
                200                 205                 210

Cys Thr Ser Ser Asn Glu Glu Gly Thr Gln Phe Cys Asn Ile Thr
                215                 220                 225

Val Ala Val Arg Ser Pro Ser Met Asn Val Ala Leu Tyr Val Gly
                230                 235                 240

Ile Ala Val Gly Val Val Ala Ala Leu Ile Ile Ile Gly Ile Ile
                245                 250                 255

Ile Tyr Cys Cys Cys Cys Arg Gly Lys Asp Asp Asn Thr Glu Asp
                260                 265                 270

Lys Glu Asp Ala Arg Pro Asn Arg Glu Ala Tyr Glu Glu Pro Pro
                275                 280                 285

Glu Gln Leu Arg Glu Leu Ser Arg Glu Arg Glu Glu Asp Asp
                290                 295                 300

Tyr Arg Gln Glu Glu Gln Arg Ser Thr Gly Arg Glu Ser Pro Asp
                305                 310                 315

His Leu Asp Gln
```

<210> SEQ ID NO 7
<211> LENGTH: 2181
<212> TYPE: DNA
<213> ORGANISM: Homo sapiens

<400> SEQUENCE: 7

| | | | | | |
|---|---|---|---|---|---|
| cccacgcgtc | cgcccacgcg | tccgcccacg | ggtccgccca | cgcgtccggg | 50 |
| ccaccagaag | tttgagcctc | tttggtagca | ggaggctgga | agaaaggaca | 100 |
| gaagtagctc | tggctgtgat | ggggatctta | ctgggcctgc | tactcctggg | 150 |
| gcacctaaca | gtggacactt | atggccgtcc | catcctggaa | gtgccagaga | 200 |
| gtgtaacagg | accttggaaa | ggggatgtga | atcttccctg | cacctatgac | 250 |
| cccctgcaag | gctacacccca | agtcttggtg | aagtggctgg | tacaacgtgg | 300 |
| ctcagaccct | gtcaccatct | ttctacgtga | ctcttctgga | gaccatatcc | 350 |
| agcaggcaaa | gtaccagggc | cgcctgcatg | tgagccacaa | ggttccagga | 400 |
| gatgtatccc | tccaattgag | caccctggag | atggatgacc | ggagccacta | 450 |
| cacgtgtgaa | gtcacctggc | agactcctga | tggcaaccaa | gtcgtgagag | 500 |
| ataagattac | tgagctccgt | gtccagaaac | tctctgtctc | caagcccaca | 550 |
| gtgacaactg | gcagcggtta | tggcttcacg | gtgcccagg | gaatgaggat | 600 |
| tagccttcaa | tgccaggctc | ggggttctcc | tcccatcagt | tatatttggt | 650 |
| ataagcaaca | gactaataac | caggaaccca | tcaaagtagc | aaccctaagt | 700 |
| accttactct | tcaagcctgc | ggtgatagcc | gactcaggct | cctatttctg | 750 |
| cactgccaag | ggccaggttg | gctctgagca | gcacagcgac | attgtgaagt | 800 |
| tgtggtcaa | agactcctca | aagctactca | agaccaagac | tgaggcacct | 850 |
| acaaccatga | cataccccctt | gaaagcaaca | tctacagtga | agcagtcctg | 900 |
| ggactggacc | actgacatgg | atggctacct | tggagagacc | agtgctgggc | 950 |
| caggaaagag | cctgcctgtc | tttgccatca | tcctcatcat | ctccttgtgc | 1000 |
| tgtatggtgg | ttttttaccat | ggcctatatc | atgctctgtc | ggaagacatc | 1050 |
| ccaacaagag | catgtctacg | aagcagccag | gtaagaaagt | ctctcctctt | 1100 |
| ccattttttga | ccccgtccct | gccctcaatt | ttgattactg | gcaggaaatg | 1150 |
| tggaggaagg | ggggtgtggc | acagacccaa | tcctaaggcc | ggaggccttc | 1200 |
| agggtcagga | catagctgcc | ttccctctct | caggcaccctt | ctgaggttgt | 1250 |
| tttggccctc | tgaacacaaa | ggataattta | gatccatctg | ccttctgctt | 1300 |
| ccagaatccc | tgggtggtag | gatcctgata | attaattggc | aagaattgag | 1350 |
| gcagaagggt | gggaaaccag | gaccacagcc | ccaagtccct | tcttatgggt | 1400 |
| ggtgggctct | tgggccatag | ggcacatgcc | agagaggcca | acgactctgg | 1450 |
| agaaaccatg | agggtggcca | tcttcgcaag | tggctgctcc | agtgatgagc | 1500 |
| caacttccca | gaatctgggc | aacaactact | ctgatgagcc | ctgcatagga | 1550 |
| caggagtacc | agatcatcgc | ccagatcaat | ggcaactacg | cccgcctgct | 1600 |
| ggacacagtt | cctctggatt | atgagtttct | ggccactgag | ggcaaaagtg | 1650 |
| tctgttaaaa | atgccccatt | aggccaggat | ctgctgacat | aattgcctag | 1700 |
| tcagtccttg | ccttctgcat | ggccttcttc | cctgctacct | ctcttcctgg | 1750 |
| atagcccaaa | gtgtccgcct | accaacactg | gagccgctgg | gagtcactgg | 1800 |

| | |
|---|---|
| ctttgccctg gaatttgcca gatgcatctc aagtaagcca gctgctggat | 1850 |
| ttggctctgg gcccttctag tatctctgcc gggggcttct ggtactcctc | 1900 |
| tctaaatacc agagggaaga tgcccatagc actaggactt ggtcatcatg | 1950 |
| cctacagaca ctattcaact ttggcatctt gccaccagaa gacccgaggg | 2000 |
| aggctcagct ctgccagctc agaggaccag ctatatccag gatcatttct | 2050 |
| cttcttcag ggccagacag cttttaattg aaattgttat ttcacaggcc | 2100 |
| agggttcagt tctgctcctc cactataagt ctaatgttct gactctctcc | 2150 |
| tggtgctcaa taaatatcta atcataacag c | 2181 |

<210> SEQ ID NO 8
<211> LENGTH: 1295
<212> TYPE: DNA
<213> ORGANISM: Homo sapiens

<400> SEQUENCE: 8

| | |
|---|---|
| cccagaagtt caagggcccc cggcctcctg cgctcctgcc gccgggaccc | 50 |
| tcgacctcct cagagcagcc ggctgccgcc ccgggaagat ggcgaggagg | 100 |
| agccgccacc gcctcctcct gctgctgctg cgctacctgg tggtcgccct | 150 |
| gggctatcat aaggcctatg gttttctgc cccaaaagac caacaagtag | 200 |
| tcacagcagt agagtaccaa gaggctattt agcctgcaa accccaaag | 250 |
| aagactgttt cctccagatt agagtggaag aaactgggtc ggagtgtctc | 300 |
| ctttgtctac tatcaacaga ctcttcaagg tgattttaaa aatcgagctg | 350 |
| agatgataga tttcaatatc cggatcaaaa atgtgacaag aagtgatgcg | 400 |
| gggaaatatc gttgtgaagt tagtgcccca tctgagcaag gccaaaacct | 450 |
| ggaagaggat acagtcactc tggaagtatt agtggctcca gcagttccat | 500 |
| catgtgaagt accctcttct gctctgagtg aactgtggt agagctacga | 550 |
| tgtcaagaca aagaagggaa tccagctcct gaatacacat ggtttaagga | 600 |
| tggcatccgt ttgctagaaa atcccagact tggctcccaa agcaccaaca | 650 |
| gctcatacac aatgaataca aaaactggaa ctctgcaatt taatactgtt | 700 |
| tccaaactgg acactggaga atattcctgt gaagcccgca attctgttgg | 750 |
| atatcgcagg tgtcctggga aacgaatgca agtagatgat ctcaacataa | 800 |
| gtggcatcat agcagccgta gtagttgtgg ccttagtgat ttccgtttgt | 850 |
| ggccttggtg tatgctatgc tcagaggaaa ggctactttt caaaagaaac | 900 |
| ctccttccag aagagtaatt cttcatctaa agccacgaca atgagtgaaa | 950 |
| atgtgcagtg gctcacgcct gtaatcccag cactttggaa ggccgcggcg | 1000 |
| gcggatcac gaggtcagga gttctagacc agtctggcca atatggtgaa | 1050 |
| accccatctc tactaaaata caaaaattag ctgggcatgg tggcatgtgc | 1100 |
| ctgcagttcc agctgcttgg gagacaggag aatcacttga acccgggagg | 1150 |
| cggaggttgc agtgagctga gatcacgcca ctgcagtcca gcctgggtaa | 1200 |
| cagagcaaga ttccatctca aaaataaaa taaataaata aataaatact | 1250 |
| ggtttttacc tgtagaattc ttacaataaa tatagcttga tattc | 1295 |

<210> SEQ ID NO 9
<211> LENGTH: 312

```
<212> TYPE: PRT
<213> ORGANISM: Homo sapiens

<400> SEQUENCE: 9

Met Ala Arg Arg Ser Arg His Arg Leu Leu Leu Leu Leu Leu Arg
 1               5                  10                  15

Tyr Leu Val Val Ala Leu Gly Tyr His Lys Ala Tyr Gly Phe Ser
             20                  25                  30

Ala Pro Lys Asp Gln Gln Val Val Thr Ala Val Glu Tyr Gln Glu
             35                  40                  45

Ala Ile Leu Ala Cys Lys Thr Pro Lys Lys Thr Val Ser Ser Arg
             50                  55                  60

Leu Glu Trp Lys Lys Leu Gly Arg Ser Val Ser Phe Val Tyr Tyr
             65                  70                  75

Gln Gln Thr Leu Gln Gly Asp Phe Lys Asn Arg Ala Glu Met Ile
             80                  85                  90

Asp Phe Asn Ile Arg Ile Lys Asn Val Thr Arg Ser Asp Ala Gly
             95                 100                 105

Lys Tyr Arg Cys Glu Val Ser Ala Pro Ser Glu Gln Gly Gln Asn
            110                 115                 120

Leu Glu Glu Asp Thr Val Thr Leu Glu Val Leu Val Ala Pro Ala
            125                 130                 135

Val Pro Ser Cys Glu Val Pro Ser Ser Ala Leu Ser Gly Thr Val
            140                 145                 150

Val Glu Leu Arg Cys Gln Asp Lys Glu Gly Asn Pro Ala Pro Glu
            155                 160                 165

Tyr Thr Trp Phe Lys Asp Gly Ile Arg Leu Leu Glu Asn Pro Arg
            170                 175                 180

Leu Gly Ser Gln Ser Thr Asn Ser Ser Tyr Thr Met Asn Thr Lys
            185                 190                 195

Thr Gly Thr Leu Gln Phe Asn Thr Val Ser Lys Leu Asp Thr Gly
            200                 205                 210

Glu Tyr Ser Cys Glu Ala Arg Asn Ser Val Gly Tyr Arg Arg Cys
            215                 220                 225

Pro Gly Lys Arg Met Gln Val Asp Asp Leu Asn Ile Ser Gly Ile
            230                 235                 240

Ile Ala Ala Val Val Val Val Ala Leu Val Ile Ser Val Cys Gly
            245                 250                 255

Leu Gly Val Cys Tyr Ala Gln Arg Lys Gly Tyr Phe Ser Lys Glu
            260                 265                 270

Thr Ser Phe Gln Lys Ser Asn Ser Ser Ser Lys Ala Thr Thr Met
            275                 280                 285

Ser Glu Asn Val Gln Trp Leu Thr Pro Val Ile Pro Ala Leu Trp
            290                 295                 300

Lys Ala Ala Ala Gly Gly Ser Arg Gly Gln Glu Phe
            305                 310

<210> SEQ ID NO 10
<211> LENGTH: 300
<212> TYPE: PRT
<213> ORGANISM: Mus musculus

<400> SEQUENCE: 10

Met Gly Thr Glu Gly Lys Ala Gly Arg Lys Leu Leu Phe Leu Phe
 1               5                  10                  15
```

```
Thr Ser Met Ile Leu Gly Ser Leu Val Gln Gly Lys Gly Ser Val
             20                  25                  30

Tyr Thr Ala Gln Ser Asp Val Gln Val Pro Glu Asn Glu Ser Ile
             35                  40                  45

Lys Leu Thr Cys Thr Tyr Ser Gly Phe Ser Ser Pro Arg Val Glu
             50                  55                  60

Trp Lys Phe Val Gln Gly Ser Thr Thr Ala Leu Val Cys Tyr Asn
             65                  70                  75

Ser Gln Ile Thr Ala Pro Tyr Ala Asp Arg Val Thr Phe Ser Ser
             80                  85                  90

Ser Gly Ile Thr Phe Ser Ser Val Thr Arg Lys Asp Asn Gly Glu
             95                 100                 105

Tyr Thr Cys Met Val Ser Glu Glu Gly Gly Gln Asn Tyr Gly Glu
            110                 115                 120

Val Ser Ile His Leu Thr Val Leu Val Pro Pro Ser Lys Pro Thr
            125                 130                 135

Ile Ser Val Pro Ser Ser Val Thr Ile Gly Asn Arg Ala Val Leu
            140                 145                 150

Thr Cys Ser Glu His Asp Gly Ser Pro Pro Ser Glu Tyr Ser Trp
            155                 160                 165

Phe Lys Asp Gly Ile Ser Met Leu Thr Ala Asp Ala Lys Lys Thr
            170                 175                 180

Arg Ala Phe Met Asn Ser Ser Phe Thr Ile Asp Pro Lys Ser Gly
            185                 190                 195

Asp Leu Ile Phe Asp Pro Val Thr Ala Phe Asp Ser Gly Glu Tyr
            200                 205                 210

Tyr Cys Gln Ala Gln Asn Gly Tyr Gly Thr Ala Met Arg Ser Glu
            215                 220                 225

Ala Ala His Met Asp Ala Val Glu Leu Asn Val Gly Gly Ile Val
            230                 235                 240

Ala Ala Val Leu Val Thr Leu Ile Leu Leu Gly Leu Leu Ile Phe
            245                 250                 255

Gly Val Trp Phe Ala Tyr Ser Arg Gly Tyr Phe Glu Thr Thr Lys
            260                 265                 270

Lys Gly Thr Ala Pro Gly Lys Lys Val Ile Tyr Ser Gln Pro Ser
            275                 280                 285

Thr Arg Ser Glu Gly Glu Phe Lys Gln Thr Ser Ser Phe Leu Val
            290                 295                 300

<210> SEQ ID NO 11
<211> LENGTH: 2181
<212> TYPE: DNA
<213> ORGANISM: Homo sapiens

<400> SEQUENCE: 11
cccacgcgtc cgcccacgcg tccgcccacg ggtccgccca cgcgtccggg         50
ccaccagaag tttgagcctc tttggtagca ggaggctgga agaaaggaca        100
gaagtagctc tggctgtgat ggggatctta ctgggcctgc tactcctggg        150
gcacctaaca gtggacactt atggccgtcc catcctggaa gtgccagaga        200
gtgtaacagg accttggaaa gggatgtgaa atcttccctg cacctatgac        250
cccctgcaag gctacaccca agtcttggtg aagtggctgg tacaacgtgg        300
ctcagaccct gtcaccatct ttctacgtga ctcttctgga gaccatatcc        350
```

-continued

| | | |
|---|---|---|
| agcaggcaaa gtaccagggc cgcctgcatg tgagccacaa ggttccagga | 400 | |
| gatgtatccc tccaattgag caccctggag atggatgacc ggagccacta | 450 | |
| cacgtgtgaa gtcacctggc agactcctga tggcaaccaa gtcgtgagag | 500 | |
| ataagattac tgagctccgt gtccagaaac tctctgtctc caagcccaca | 550 | |
| gtgacaactg gcagcggtta tggcttcacg gtgccccagg gaatgaggat | 600 | |
| tagccttcaa tgccaggctc ggggttctcc tcccatcagt tatatttggt | 650 | |
| ataagcaaca gactaataac caggaaccca tcaaagtagc aaccctaagt | 700 | |
| accttactct tcaagcctgc ggtgatagcc gactcaggct cctatttctg | 750 | |
| cactgccaag ggccaggttg gctctgagca gcacagcgac attgtgaagt | 800 | |
| ttgtggtcaa agactcctca aagctactca agaccaagac tgaggcacct | 850 | |
| acaaccatga cataccccctt gaaagcaaca tctacagtga agcagtcctg | 900 | |
| ggactggacc actgacatgg atggctacct tggagagacc agtgctgggc | 950 | |
| caggaaagag cctgcctgtc tttgccatca tcctcatcat ctccttgtgc | 1000 | |
| tgtatggtgg tttttaccat ggcctatatc atgctctgtc ggaagacatc | 1050 | |
| ccaacaagag catgtctacg aagcagccag gtaagaaagt ctctcctctt | 1100 | |
| ccattttga ccccgtccct gccctcaatt ttgattactg gcaggaaatg | 1150 | |
| tggaggaagg ggggtgtggc acagacccaa tcctaaggcc ggaggccttc | 1200 | |
| agggtcagga catagctgcc ttccctctct caggcacctt ctgaggttgt | 1250 | |
| tttggccctc tgaacacaaa ggataattta gatccatctg ccttctgctt | 1300 | |
| ccagaatccc tgggtggtag gatcctgata attaattggc aagaattgag | 1350 | |
| gcagaagggt gggaaaccag gaccacagcc ccaagtccct tcttatgggt | 1400 | |
| ggtgggctct tgggccatag ggcacatgcc agagaggcca acgactctgg | 1450 | |
| agaaaccatg agggtggcca tcttcgcaag tggctgctcc agtgatgagc | 1500 | |
| caacttccca gaatctgggc aacaactact ctgatgagcc ctgcatagga | 1550 | |
| caggagtacc agatcatcgc ccagatcaat ggcaactacg cccgcctgct | 1600 | |
| ggacacagtt cctctggatt atgagtttct ggccactgag ggcaaaagtg | 1650 | |
| tctgttaaaa atgccccatt aggccaggat ctgctgacat aattgcctag | 1700 | |
| tcagtccttg ccttctgcat ggccttcttc cctgctacct ctcttcctgg | 1750 | |
| atagcccaaa gtgtccgcct accaacactg gagccgctgg gagtcactgg | 1800 | |
| ctttgccctg gaatttgcca gatgcatctc aagtaagcca gctgctggat | 1850 | |
| ttggctctgg gccttctag tatctctgcc ggggcttct ggtactcctc | 1900 | |
| tctaaatacc agagggaaga tgcccatagc actaggactt ggtcatcatg | 1950 | |
| cctacagaca ctattcaact ttggcatctt gccaccagaa gacccgaggg | 2000 | |
| aggctcagct ctgccagctc agaggaccag ctatatccag gatcatttct | 2050 | |
| ctttcttcag ggccagacag cttttaattg aaattgttat ttcacaggcc | 2100 | |
| agggttcagt tctgctcctc cactataagt ctaatgttct gactctctcc | 2150 | |
| tggtgctcaa taaatatcta atcataacag c | 2181 | |

<210> SEQ ID NO 12
<211> LENGTH: 24
<212> TYPE: DNA
<213> ORGANISM: artificial sequence

```
<220> FEATURE:
<223> OTHER INFORMATION: Synthetic oligonucleotide probe

<400> SEQUENCE: 12
tcgcggagct gtgttctgtt tccc                                              24

<210> SEQ ID NO 13
<211> LENGTH: 50
<212> TYPE: DNA
<213> ORGANISM: artificial sequence
<220> FEATURE:
<223> OTHER INFORMATION: Synthetic oligonucleotide probe

<400> SEQUENCE: 13
tgatcgcgat ggggacaaag gcgcaagctc gagaggaaac tgttgtgcct                  50

<210> SEQ ID NO 14
<211> LENGTH: 20
<212> TYPE: DNA
<213> ORGANISM: artificial sequence
<220> FEATURE:
<223> OTHER INFORMATION: Synthetic oligonucleotide probe

<400> SEQUENCE: 14
acacctggtt caaagatggg                                                   20

<210> SEQ ID NO 15
<211> LENGTH: 24
<212> TYPE: DNA
<213> ORGANISM: artificial sequence
<220> FEATURE:
<223> OTHER INFORMATION: Synthetic oligonucleotide probe

<400> SEQUENCE: 15
taggaagagt tgctgaaggc acgg                                              24

<210> SEQ ID NO 16
<211> LENGTH: 20
<212> TYPE: DNA
<213> ORGANISM: artificial sequence
<220> FEATURE:
<223> OTHER INFORMATION: Synthetic oligonucleotide probe

<400> SEQUENCE: 16
ttgccttact caggtgctac                                                   20

<210> SEQ ID NO 17
<211> LENGTH: 20
<212> TYPE: DNA
<213> ORGANISM: artificial sequence
<220> FEATURE:
<223> OTHER INFORMATION: Synthetic oligonucleotide probe

<400> SEQUENCE: 17
actcagcagt ggtaggaaag                                                   20

<210> SEQ ID NO 18
<211> LENGTH: 24
<212> TYPE: DNA
<213> ORGANISM: artificial sequence
<220> FEATURE:
<223> OTHER INFORMATION: Synthetic oligonucleotide probe

<400> SEQUENCE: 18
tatccctcca attgagcacc ctgg                                              24
```

-continued

<210> SEQ ID NO 19
<211> LENGTH: 21
<212> TYPE: DNA
<213> ORGANISM: artificial sequence
<220> FEATURE:
<223> OTHER INFORMATION: Synthetic oligonucleotide probe

<400> SEQUENCE: 19
gtcggaagac atcccaacaa g                                             21

<210> SEQ ID NO 20
<211> LENGTH: 24
<212> TYPE: DNA
<213> ORGANISM: artificial sequence
<220> FEATURE:
<223> OTHER INFORMATION: Synthetic oligonucleotide probe

<400> SEQUENCE: 20
cttcacaatg tcgctgtgct gctc                                          24

<210> SEQ ID NO 21
<211> LENGTH: 24
<212> TYPE: DNA
<213> ORGANISM: artificial sequence
<220> FEATURE:
<223> OTHER INFORMATION: Synthetic oligonucleotide probe

<400> SEQUENCE: 21
agccaaatcc agcagctggc ttac                                          24

<210> SEQ ID NO 22
<211> LENGTH: 50
<212> TYPE: DNA
<213> ORGANISM: artificial sequence
<220> FEATURE:
<223> OTHER INFORMATION: Synthetic oligonucleotide probe

<400> SEQUENCE: 22
tggatgaccg gagccactac acgtgtgaag tcacctggca gactcctgat              50

<210> SEQ ID NO 23
<211> LENGTH: 260
<212> TYPE: PRT
<213> ORGANISM: Homo sapiens

<400> SEQUENCE: 23

Leu Ala Leu Gly Ser Val Thr Val His Ser Ser Glu Pro Glu Val
  1               5                  10                  15

Arg Ile Pro Glu Asn Asn Pro Val Lys Leu Ser Cys Ala Tyr Ser
                 20                  25                  30

Gly Phe Ser Ser Pro Arg Val Glu Trp Lys Phe Asp Gln Gly Asp
                 35                  40                  45

Thr Thr Arg Leu Val Cys Tyr Asn Asn Lys Ile Thr Ala Ser Tyr
                 50                  55                  60

Glu Asp Arg Val Thr Phe Leu Pro Thr Gly Ile Thr Phe Lys Ser
                 65                  70                  75

Val Thr Arg Glu Asp Thr Gly Thr Tyr Thr Cys Met Val Ser Glu
                 80                  85                  90

Glu Gly Gly Asn Ser Tyr Gly Glu Val Lys Val Lys Leu Ile Val
                 95                 100                 105

Leu Val Pro Pro Ser Lys Pro Thr Val Asn Ile Pro Ser Ser Ala
                110                 115                 120

```
Thr Ile Gly Asn Arg Ala Val Leu Thr Cys Ser Glu Gln Asp Gly
            125                 130                 135

Ser Pro Pro Ser Glu Tyr Thr Trp Phe Lys Asp Gly Ile Val Met
            140                 145                 150

Pro Thr Asn Pro Lys Ser Thr Arg Ala Phe Ser Asn Ser Ser Tyr
            155                 160                 165

Val Leu Asn Pro Thr Thr Gly Glu Leu Val Phe Asp Pro Leu Ser
            170                 175                 180

Ala Ser Asp Thr Gly Glu Tyr Ser Cys Glu Ala Arg Asn Gly Tyr
            185                 190                 195

Gly Thr Pro Met Thr Ser Asn Ala Val Arg Met Glu Ala Val Glu
            200                 205                 210

Arg Asn Val Gly Val Ile Val Ala Ala Val Leu Val Thr Leu Ile
            215                 220                 225

Leu Leu Gly Ile Leu Val Phe Gly Ile Trp Phe Ala Tyr Ser Arg
            230                 235                 240

Gly His Phe Asp Arg Thr Lys Lys Gly Thr Ser Ser Lys Lys Val
            245                 250                 255

Ile Tyr Ser Gln Pro
            260

<210> SEQ ID NO 24
<211> LENGTH: 270
<212> TYPE: PRT
<213> ORGANISM: Homo sapiens

<400> SEQUENCE: 24

Val Arg Val Thr Val Asp Ala Ile Ser Val Glu Thr Pro Gln Asp
  1               5                  10                  15

Val Leu Arg Ala Ser Gln Gly Lys Ser Val Thr Leu Pro Cys Thr
             20                  25                  30

Tyr His Thr Ser Thr Ser Ser Arg Glu Gly Leu Ile Gln Trp Asp
             35                  40                  45

Lys Leu Leu Leu Thr His Thr Glu Arg Val Val Ile Trp Pro Phe
             50                  55                  60

Ser Asn Lys Asn Tyr Ile His Gly Glu Leu Tyr Lys Asn Arg Val
             65                  70                  75

Ser Ile Ser Asn Asn Ala Glu Gln Ser Asp Ala Ser Ile Thr Ile
             80                  85                  90

Asp Gln Leu Thr Met Ala Asp Asn Gly Thr Tyr Glu Cys Ser Val
             95                 100                 105

Ser Leu Met Ser Asp Leu Glu Gly Asn Thr Lys Ser Arg Val Arg
            110                 115                 120

Leu Leu Val Leu Val Pro Pro Ser Lys Pro Glu Cys Gly Ile Glu
            125                 130                 135

Gly Glu Thr Ile Ile Gly Asn Asn Ile Gln Leu Thr Cys Gln Ser
            140                 145                 150

Lys Glu Gly Ser Pro Thr Pro Gln Tyr Ser Trp Lys Arg Tyr Asn
            155                 160                 165

Ile Leu Asn Gln Glu Gln Pro Leu Ala Gln Pro Ala Ser Gly Gln
            170                 175                 180

Pro Val Ser Leu Lys Asn Ile Ser Thr Asp Thr Ser Gly Tyr Tyr
            185                 190                 195

Ile Cys Thr Ser Ser Asn Glu Glu Gly Thr Gln Phe Cys Asn Ile
```

|  | 200 | | | | 205 | | | | 210 | |
|---|---|---|---|---|---|---|---|---|---|---|
| Thr | Val | Ala | Val | Arg | Ser | Pro | Ser | Met | Asn | Val | Ala | Leu | Tyr | Val |
| | | | | 215 | | | | | 220 | | | | | 225 |
| Gly | Ile | Ala | Val | Gly | Val | Val | Ala | Ala | Leu | Ile | Ile | Ile | Gly | Ile |
| | | | | 230 | | | | | 235 | | | | | 240 |
| Ile | Ile | Tyr | Cys | Cys | Cys | Cys | Arg | Gly | Lys | Asp | Asp | Asn | Thr | Glu |
| | | | | 245 | | | | | 250 | | | | | 255 |
| Asp | Lys | Glu | Asp | Ala | Arg | Pro | Asn | Arg | Glu | Ala | Tyr | Glu | Glu | Pro |
| | | | | 260 | | | | | 265 | | | | | 270 |

<210> SEQ ID NO 25
<211> LENGTH: 263
<212> TYPE: PRT
<213> ORGANISM: Homo sapiens

<400> SEQUENCE: 25

Leu Cys Ser Leu Ala Leu Gly Ser Val Thr Val His Ser Ser Glu
 1               5                  10                  15
Pro Glu Val Arg Ile Pro Glu Asn Asn Pro Val Lys Leu Ser Cys
                20                  25                  30
Ala Tyr Ser Gly Phe Ser Ser Pro Arg Val Glu Trp Lys Phe Asp
                35                  40                  45
Gln Gly Asp Thr Thr Arg Leu Val Cys Tyr Asn Asn Lys Ile Thr
                50                  55                  60
Ala Ser Tyr Glu Asp Arg Val Thr Phe Leu Pro Thr Gly Ile Thr
                65                  70                  75
Phe Lys Ser Val Thr Arg Glu Asp Thr Gly Thr Tyr Thr Cys Met
                80                  85                  90
Val Ser Glu Glu Gly Gly Asn Ser Tyr Gly Glu Val Lys Val Lys
                95                  100                 105
Leu Ile Val Leu Val Pro Pro Ser Lys Pro Thr Val Asn Ile Pro
                110                 115                 120
Ser Ser Ala Thr Ile Gly Asn Arg Ala Val Leu Thr Cys Ser Glu
                125                 130                 135
Gln Asp Gly Ser Pro Pro Ser Glu Tyr Thr Trp Phe Lys Asp Gly
                140                 145                 150
Ile Val Met Pro Thr Asn Pro Lys Ser Thr Arg Ala Phe Ser Asn
                155                 160                 165
Ser Ser Tyr Val Leu Asn Pro Thr Thr Gly Glu Leu Val Phe Asp
                170                 175                 180
Pro Leu Ser Ala Ser Asp Thr Gly Glu Tyr Ser Cys Glu Ala Arg
                185                 190                 195
Asn Gly Tyr Gly Thr Pro Met Thr Ser Asn Ala Val Arg Met Glu
                200                 205                 210
Ala Val Glu Arg Asn Val Gly Val Ile Val Ala Ala Val Leu Val
                215                 220                 225
Thr Leu Ile Leu Leu Gly Ile Leu Val Phe Gly Ile Trp Phe Ala
                230                 235                 240
Tyr Ser Arg Gly His Phe Asp Arg Thr Lys Lys Gly Thr Ser Ser
                245                 250                 255
Lys Lys Val Ile Tyr Ser Gln Pro
                260

<210> SEQ ID NO 26
<211> LENGTH: 273

```
<212> TYPE: PRT
<213> ORGANISM: Homo sapiens

<400> SEQUENCE: 26

Leu Cys Ala Val Arg Val Thr Val Asp Ala Ile Ser Val Glu Thr
  1               5                  10                  15

Pro Gln Asp Val Leu Arg Ala Ser Gln Gly Lys Ser Val Thr Leu
                 20                  25                  30

Pro Cys Thr Tyr His Thr Ser Thr Ser Arg Glu Gly Leu Ile
                 35                  40                  45

Gln Trp Asp Lys Leu Leu Leu Thr His Thr Glu Arg Val Val Ile
                 50                  55                  60

Trp Pro Phe Ser Asn Lys Asn Tyr Ile His Gly Glu Leu Tyr Lys
                 65                  70                  75

Asn Arg Val Ser Ile Ser Asn Asn Ala Glu Gln Ser Asp Ala Ser
                 80                  85                  90

Ile Thr Ile Asp Gln Leu Thr Met Ala Asp Asn Gly Thr Tyr Glu
                 95                 100                 105

Cys Ser Val Ser Leu Met Ser Asp Leu Glu Gly Asn Thr Lys Ser
                110                 115                 120

Arg Val Arg Leu Leu Val Leu Val Pro Pro Ser Lys Pro Glu Cys
                125                 130                 135

Gly Ile Glu Gly Glu Thr Ile Ile Gly Asn Asn Ile Gln Leu Thr
                140                 145                 150

Cys Gln Ser Lys Glu Gly Ser Pro Thr Pro Gln Tyr Ser Trp Lys
                155                 160                 165

Arg Tyr Asn Ile Leu Asn Gln Glu Gln Pro Leu Ala Gln Pro Ala
                170                 175                 180

Ser Gly Gln Pro Val Ser Leu Lys Asn Ile Ser Thr Asp Thr Ser
                185                 190                 195

Gly Tyr Tyr Ile Cys Thr Ser Ser Asn Glu Glu Gly Thr Gln Phe
                200                 205                 210

Cys Asn Ile Thr Val Ala Val Arg Ser Pro Ser Met Asn Val Ala
                215                 220                 225

Leu Tyr Val Gly Ile Ala Val Gly Val Val Ala Ala Leu Ile Ile
                230                 235                 240

Ile Gly Ile Ile Ile Tyr Cys Cys Cys Cys Arg Gly Lys Asp Asp
                245                 250                 255

Asn Thr Glu Asp Lys Glu Asp Ala Arg Pro Asn Arg Glu Ala Tyr
                260                 265                 270

Glu Glu Pro

<210> SEQ ID NO 27
<211> LENGTH: 413
<212> TYPE: DNA
<213> ORGANISM: Homo Sapien

<400> SEQUENCE: 27
ctcgagccgc tcgagccgtg cggggaaata tcgttgtgaa gttagtgccc          50
catctgagca aggccaaaac ctggaagagg atacagtcac tctggaagta         100
ttagtggctc cagcagttcc atcatgtgaa gtaccctctt ctgctctgag         150
tggaactgtg gtagagctac gatgtcaaga caaagaaggg aatccagctc         200
ctgaatacac atggtttaag gatggcatcc gtttgctaga aaatcccaga         250
```

```
                                                    -continued
cttggctccc aaagcaccaa cagctcatac acaatgaata caaaaactgg              300
aactctgcaa tttaatactg tttccaaact ggacactgga gaatattcct              350
gtgaagcccg caattctgtt ggatatcgca ggtgtcctgg ggaaacgaat              400
gcaagtagat gat                                                      413

<210> SEQ ID NO 28
<211> LENGTH: 22
<212> TYPE: DNA
<213> ORGANISM: artificial sequence
<220> FEATURE:
<223> OTHER INFORMATION: Synthetic oligonucleotide probe

<400> SEQUENCE: 28
atcgttgtga agttagtgcc cc                                             22

<210> SEQ ID NO 29
<211> LENGTH: 23
<212> TYPE: DNA
<213> ORGANISM: artificial sequence
<220> FEATURE:
<223> OTHER INFORMATION: Synthetic oligonucleotide probe

<400> SEQUENCE: 29
acctgcgata tccaacagaa ttg                                            23

<210> SEQ ID NO 30
<211> LENGTH: 48
<212> TYPE: DNA
<213> ORGANISM: artificial sequence
<220> FEATURE:
<223> OTHER INFORMATION: Synthetic oligonucleotide probe

<400> SEQUENCE: 30
ggaagaggat acagtcactc tggaagtatt agtggctcca gcagttcc                 48
```

COMPOUNDS, COMPOSITIONS AND METHODS FOR THE TREATMENT OF DISEASES CHARACTERIZED BY A-33 RELATED ANTIGENS

This application is a divisional of U.S. application Ser. No. 09/953,499 filed Sep. 14, 2001 (now U.S. Pat. No. 6,838,554 issued Jan. 4, 2005), which is a continuation of, and claims priority under 35 USC §120 to, U.S. application Ser. No. 09/254,465 filed Mar. 5, 1999 (now U.S. Pat. No. 6,410,708 issued Jun. 25, 2005), which is a continuation of, and claims priority under 35 USC 120 to, PCT Application PCT/US98/24855 filed Nov. 20, 1998 which claims priority under 35 USC § 119 to U.S. Provisional Application 60/066,364 filed Nov. 21, 1997, and where PCT Application PCT/US98/24855 is also-a continuation-in-part of PCT/US98/19437 filed Sep. 17, 1998, the disclosures of which are expressly incorporated herein by reference.

FIELD OF THE INVENTION

The present invention relates generally to the identification, isolation and recombinant production of novel DNA and novel polypeptides the presence of which is associated with inflammatory diseases (inflammation associated antigens) and/or cancer, and to compositions and methods for the diagnosis and treatment of conditions characterized by such antigens.

BACKGROUND OF THE INVENTION

The inflammatory response is complex and is mediated by a variety of signaling molecules produced locally by mast cells, nerve endings, platelets, leucocytes and complement activation. Certain of these signaling molecules cause the endothelial cell lining to become more porous and/or even to express selections which act as cell surface molecules which -recognize and attract leucocytes through specific carbohydrate recognition. Stronger leucocyte binding is mediated by integrins, which mediate leucocyte movement through the endothelium. Additional signaling molecules act as chemoattractants, causing the bound leucocytes to crawl towards the source of the attractant. Other signaling molecules produced in the course of an inflammatory response escape into the blood and stimulate the bone marrow to produce more leucocytes and release them into the blood stream.

Inflammation is typically initiated by an antigen, which can be virtually any molecule capable of initiating an immune response. Under normal physiological conditions these are foreign molecules, but molecules generated by the organism itself can serve as the catalyst as is known to occur in various disease states.

T-cell proliferation in a mixed lymphocyte culture or mixed lymphocyte reaction (MLR) is an established indication of the ability of a compound to stimulate the immune system. In an inflammatory response, the responding leucocytes can be neutrophilic, eosinophilic, monocytic or lymphocytic. Histological examination of the affected tissues provides evidence of an immune stimulating or inhibiting response. See *Current Protocols in Immunology*, ed. John E. Coligan, 1994, John Wiley and Sons, Inc.

Inflammatory bowel disease (IBD) is a term used to collectively describe gut disorders including both ulcerative colitis (UC) and Crohn's disease, both of which are classified as distinct disorders, but share common features and likely share pathology. The commonality of the diagnostic criteria can make it difficult to precisely determine which of the two disorders a patients has; however the type and location of the lesion in each are typically different. UC lesions are characteristically a superficial ulcer of the mucosa and appear in the colon, proximal to the rectum. CD lesions are characteristically extensive linear fissures, and can appear anywhere in the bowel, occasionally involving the stomach, esophagus and duodenum.

Conventional treatments for IBD usually involve the administration of antiinflammatory or immunosuppressive agents, such as sulfasalazine, corticosteroids, 6-mercaptopurine/azathoprine, or cyclosporine all of which only bring partial relief to the afflicted patient. However when antiinflammatory/immunosuppresive therapies fail, colectomies are the last line of defense. Surgery is required for about 30% of CD patients within the first year after diagnosis, with the likelihood for operative procedure increasing about 5% annually thereafter. Unfortunately, CD also has a high rate of reoccurrence as about 5% of patients require subsequent surgery after the initial year. UC patients further have a substantially increased risk of developing colorectal cancer. Presumably this is due to the recurrent cycles of injury to the epithelium, followed by regrowth, which continually increases the risk of neoplastic transformation.

A recently discovered member of the immunoglobulin superfamily known as Junctional Adhesion Molecule (JAM) has been identified to be selectively concentrated at intercellular junctions of endothelial and epithelial cells of different origins. Martin-Padura, I. et al., *J. Cell Biol.* 142(1): 117-27 (1998). JAM is a type I integral membrane protein with two extracellular, intrachain disulfide loops of the V-type. JAM bears substantial homology to A33 antigen (FIG. 1 or FIG. 18). A monoclonal antibody directed to JAM was found to inhibit spontaneous and chemokine-induced monocyte transmigration through an endothelial cell monolayer in vitro. Martin-Padura, supra It has been recently discovered that JAM expression is increased in the colon of CRF2-4 −/− mice with colitis. CRF 24 −/− (IL-10R subunit knockout mice) develop a spontaneous colitis mediated by lymphocytes, monocytes and neutrophils. Several of the animals also developed colon adenocarcinoma. As a result, it is foreseeable likely that the compounds of the invention are expressed in elevated levels in or otherwise associated with human diseases such as inflammatory bowel disease, other inflammatory diseases of the gut as well as colorectal carcinoma.

The compounds of the invention also bear significant homology to A33 antigen, a known colorectal cancer-associated marker. The A33 antigen is expressed in more than 90% of primary or metastatic colon cancers as well as normal colon epithelium. In carcinomas originating from the colonic mucosa, the A33 antigen is expressed homogeneously in more than 95% of all cases. The A33 antigen, however, has not been detected in a wide range of other normal tissues, i.e., its expression appears to be organ specific. Therefore, the A33 antigen appears to play an important role in the induction of colorectal cancer.

Since colon cancer is a widespread disease, early diagnosis and treatment is an important medical goal. Diagnosis and treatment of colon cancer can be implemented using monoclonal antibodies (mAbs) specific therefore having fluorescent, nuclear magnetic or radioactive tags. Radioactive gene, toxins and/or drug tagged mAbs can be used for treatment in situ with minimal patient description. mAbs can also be used to diagnose during the diagnosis and treatment of colon cancers. For example, when the serum levels of the A33 antigen are elevated in a patient, a drop of the levels after surgery would indicate the tumor resection was successful. On the other hand, a subsequent rise in serum A33 antigen levels after surgery would indicate that metastases of the original tumor may have formed or that new primary tumors may have appeared.

Such monoclonal antibodies can be used in lieu of, or in conjunction with surgery and/or other chemotherapies. For example, preclinical analysis and localization studies in patients infected with colorectal carcinoma with a mAb to A33 are described in Welt et al., *J. Clin. Oncol.* 8: 1894-1906 (1990) and Welt et al., *J. Clin. Oncol.* 12: 1561-1571 (1994), while U.S. Pat. No. 4,579,827 and U.S. Ser. No. 424,991 (E.P. 199,141) are directed to the therapeutic administration of monoclonal antibodies, the latter of which relates to the application of anti-A33 mAb.

SUMMARY OF THE INVENTION

The present invention further concerns compositions and methods for the diagnosis and treatment of inflammatory diseases in mammals, including humans. The present invention is based on the identification of proteins (including agonist and antagonist antibodies) which either stimulate or inhibit the immune response in mammals. Inflammatory diseases can be treated by suppressing the inflammatory response. Molecules that enhance an inflammatory response stimulate or potentiate the immune response to an antigen. Molecules which stimulate an inflammatory response can be inhibited where suppression of the inflammatory response would be beneficial. Molecules which stimulate the inflammatory response can be used therapeutically where enhancement of the inflammatory response would be beneficial. Such stimulatory molecules can also be inhibited where suppression of the inflammatory response would be of value. Neutralizing antibodies are examples of molecules that inhibit molecules having immune stimulatory activity and which would be beneficial in the treatment of inflammatory diseases. Molecules which inhibit the inflammatory response can also be utilized (proteins directly or via the use of antibody agonists) to inhibit the inflammatory response and thus ameliorate inflammatory diseases.

Accordingly, the proteins of the invention are useful for the diagnosis and/or treatment (including prevention) of immune related diseases. Antibodies which bind to stimulatory proteins are useful to suppress the inflammatory response. Antibodies which bind to inhibitory proteins are useful to stimulate inflammatory response and the immune system. The proteins and antibodies of the invention are also useful to prepare medicines and medicaments for the treatment of inflammatory and immune related diseases.

In one embodiment, the invention concerns antagonists and agonists of a PRO301, PRO362 or PRO245 polypeptide that inhibits one or more of the functions or activities of PRO301, PRO362 or PRO245 polypeptide.

In another embodiment, the invention concerns a method for determining the presence of a PRO301, PRO362 or PRO245 polypeptide comprising exposing a cell suspected of containing the polypeptide to an anti-PRO301, anti-PRO362 or anti-PRO245 antibody and determining binding of the antibody to the cell.

In yet another embodiment, the present invention relates to a method of diagnosing an inflammatory related disease in a mammal, comprising detecting the level of expression of a gene encoding a PRO301, PRO362 or PRO245 polypeptide (a) in a test sample of tissue cells obtained from the mammal, and (b) in a control sample of known normal tissue cells of the same cell type, wherein a higher expression level in the test sample indicates the presence of an inflammatory disease in the mammal.

In another embodiment, the present invention relates to method of diagnosing an inflammatory disease in a mammal, comprising (a) contacting an anti-PRO301, anti-PRO362 or anti-PRO245 antibody with a test sample of tissue culture cells obtained from the mammal, and (b) detecting the formation of a complex between the antibody and the PRO301, PRO362 or PRO245 polypeptide. The detection may be qualitative or quantitative, and may be performed in comparison with monitoring the complex formation in a control sample of known normal tissue cells of the same cell type. A larger quantity of complexes formed in the test sample indicates the presence of tumor in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected of having a deficiency or abnormality relating to the inflammatory response.

In another embodiment, the present invention relates to a diagnostic kit, containing an anti-PRO301, anti-PRO362 or anti-PRO245 antibody and a carrier (e.g., a buffer) in suitable packaging. The kit preferably contains instructions for using the antibody to detect the PRO301, PRO362 polypeptide.

In a further embodiment, the invention concerns an article of manufacture, comprising:

a container;

a label on the container; and a composition comprising an active agent contained within the container; wherein the composition is effective for stimulating or inhibiting an inflammatory response in a mammal, the label on the container indicates that the composition can be used to treat an inflammatory disease, and the active agent in the composition is an agent stimulating or inhibiting the expression and/or activity of the PRO301, PRO362 or PRO245 polypeptide. In a preferred aspect, the active agent is a PRO301, PRO362 or PRO245 polypeptide or an anti-PRO301, anti-PRO362 or anti-PRO245 antibody.

A further embodiment is a method for identifying a compound capable of inhibiting the expression and/or activity of a PRO301, PRO362 or PRO245 polypeptide by contacting a candidate compound with a PRO301, PRO362 or PRO245 polypeptide under conditions and for time sufficient to allow these two compounds to interact. In a specific aspect, either the candidate compound or the PRO301, PRO362 or PRO245 polypeptide is immobilized on a solid support. In another aspect, the non-immobilized component carries a detectable label.

In yet a further aspect, the invention relates to a method of treating an inflammatory disease, by administration of an effective therapeutic amount of a PRO301, PRO362 or PRO245 antagonist to a patient in need thereof for the treatment of a disease selected from: inflammatory bowel disease, systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis, eosinophilic pneumonias, idiopathic pulmonary fibrosis and hypersensitivity pneumonitis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonias, idiopathic pulmonary fibrosis and hypersensitivity pneumonitis, transplantation associated diseases including graft rejection and graft-verus host disease.

In a further embodiment, the present invention provides a method of diagnosing tumor in a mammal, comprising detecting the level of expression of a gene encoding a PRO201, 362 or PRO245 polypeptide (a) in a test sample of tissue cells obtained from the mammal, and (b) in a control sample of known normal tissue cells of the same cell type, wherein a higher expression level in the test sample indicates the presence of tumor in the mammal from which the test tissue cells were obtained.

In another embodiment, the present invention provides a method of diagnosing tumor in a mammal, comprising (a) contacting an anti-PRO301, anti-PRO362 or anti-PRO245 antibody with a test sample of the tissue cells obtained from the mammal, and (b) detecting the formation of a complex between the anti-PRO301, anti-PRO362 or anti-PRO245 and the PRO301, PRO362 or PRO245 polypeptide in the test sample. The detection may be qualitative or quantitative, and may be performed in comparison with monitoring the complex formation in a control sample of known normal tissue cells of the same cell type. A larger quantity of complexes formed in the test sample indicates the presence of tumor in the mammal from which the test tissue cells were obtained. The antibody preferably carries a detectable label. Complex formation can be monitored, for example, by light microscopy, flow cytometry, fluorimetry, or other techniques known in the art. Preferably, the test sample is obtained from an individual mammal suspected to have neoplastic cell growth or proliferation (e.g., cancerous cells).

In another embodiment, the present invention provides a cancer diagnostic kit, comprising an anti-PRO301, PRO362 or PRO245 antibody and a carrier (e.g. a buffer) in suitable packaging. The kit preferably contains instructions for using the antibody to detect the PRO301, PRO362 or PRO245 polypeptide.

In yet another embodiment, the invention provides a method for inhibiting the growth of tumor cells comprising exposing a cell which overexpresses a PRO301, PRO362 or PRO245 polypeptide to an effective amount of an agent inhibiting the expression and/or activity of the PRO301, PRO362 or PRO245 polypeptide. The agent preferably is an anti-PRO301, anti-PRO362 or anti-PRO245 polypeptide, a small organic and inorganic peptide, phosphopeptide, antisense or ribozyme molecule, or a triple helix molecule. In a specific aspect, the agent, e.g., anti-PRO301, anti-PRO362 or anti-PRO245 antibody induces cell death. In a further aspect, the tumor cells are further exposed to radiation treatment and/or a cytotoxic or chemotherapeutic agent.

In a further embodiment, the invention concerns an article of manufacture, comprising:
a container;
a label on the container, and
a composition comprising an active agent contained within the container; wherein the composition is effective for inhibiting the growth of tumor cells, the label on the container indicates that the composition can be used for treating conditions characterized by overexpression of a PRO301, PRO362 or PRO245 polypeptide, and the active agent in the composition is an agent inhibiting the expression and/or activity of the PRO301, PRO362 or PRO245 polypeptide. In a preferred aspect, the active agent is an anti-PRO301, anti-PRO362 or anti-PRO245 antibody.

In a further embodiment, the invention provides an isolated nucleic acid molecule having at least about 80% sequence identity to (a) a DNA molecule encoding a PRO301 polypeptide comprising the sequence of amino acids 28 to 258 of FIG. 2 (SEQ ID NO: 1), or (b) the complement of the DNA molecule of (a). The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues about 28 to 235 of FIG. 2 (SEQ ID NO: 1). Preferably, the highest degree of sequence identity occurs within the extracellular domains (amino acids 28 to 235 of FIG. 2, SEQ ID NO: 1). In a further embodiment, the isolated nucleic acid molecule comprises DNA encoding a PRO301 polypeptide having amino acid residues 28 to 299 of FIG. 2 (SEQ ID NO: 1), or is complementary to such encoding nucleic acid sequence, and remains stably bound to it under at least moderate, and optionally, under high stringency conditions. In another aspect, the invention provides a nucleic acid of the full length protein of clone DNA40628, deposited with the ATCC under accession number ATCC 209432, alternatively the coding sequence of clone DNA40628, deposited under accession number ATCC 209432.

In another embodiment, the invention provides an isolated nucleic acid molecule comprising DNA encoding a PRO362 polypeptide. In one aspect, the isolated nucleic acid comprises DNA encoding the PRO362 polypeptide having amino acid residues 1 to 321 of FIG. 3 (SEQ ID NO: 2), or is complementary to such encoding nucleic acid sequence, and remains stably bound to it under at least moderate, and optionally, under high stringency conditions. In another aspect, the isolated nucleic acid comprises DNA encoding the PRO362 polypeptide having amino acid residues 1 to X or FIG. 3 (SEQ ID NO: 2), where X is any amino acid residue from 271 to 280, or is complementary to such encoding nucleic acid sequence, and remains stably bound to it under at least moderate, and optionally, under high stringency conditions. The isolated nucleic acid sequence may comprise the cDNA insert of the DNA45416-1251 vector deposited on Feb. 5, 1998 as ATCC 209620 which includes the nucleotide sequence encoding PRO362.

In yet another embodiment, the invention provides isolated nucleic acid molecules that hybridize to the complement of the nucleic acid molecules encoding the PRO301, PRO362 or PRO245 polypeptides. The nucleic acid preferably is DNA, and hybridization occurs under stringent conditions. Such nucleic acid molecules can act as antisense molecules of the inflammation associated antigens identified herein, which, in turn, can find use in the modulation of the inflammation associated antigens, or as antisense primers in amplification reactions. Furthermore, such sequences can be used as part of ribozyme and/or triple helix sequence which, in turn, may be used in regulation of the inflammation associated antigens.

In yet another embodiment, the invention provides a vector comprising DNA encoding PRO301 or a PRO362 polypeptide. A host cell comprising such a vector is also provided. By way of example, the host cells may be CHO cells, *E. coli*, or yeast. A process for producing PRO301 or PRO362 polypeptides is further provided and comprises culturing host cells under conditions suitable for expression of PRO301 or PRO362 and recovering the same from the cell culture.

In yet another embodiment, the invention provides isolated PRO301 polypeptide. In particular, the invention provides isolated native sequence PRO301 polypeptide, which in one embodiment, includes an amino acid sequence comprising the extracellular domain residues 28 to 235 of FIG. 2 (SEQ ID NO: 1). Native PRO301 polypeptides with or without the native signal sequence (amino acids 1 to 27 in FIG. 2 (SEQ ID NO: 1), and with or without the initiating methionine are specifically included. Additionally, the sequences of the invention may also comprise the transmembrane domain (residues 236 to 258 in FIG. 2)(SEQ ID NO: 1) and/or the intracellular domain (residue 259 to 299 in FIG. 2)(SEQ ID NO: 1). Alternatively, the invention provides a PRO301 polypeptide encoded by the nucleic acid deposited under accession number ATCC 209432.

In yet another embodiment, the invention provides isolated PRO362 polypeptide. In particular, the invention provides isolated native sequence PRO362, which in one aspect, includes an amino acid sequence comprising residues 1 to 321 of FIG. 3 (SEQ ID NO: 2). An additional embodiment of the present invention is directed to an isolated extracellular domain of a PRO362 polypeptide comprising amino acids 1 to X of the FIG. 2 (SEQ ID NO: 2), wherein X is any amino acid residue 271-280. Optionally, the PRO362 polypeptide is obtained or is obtainable by expressing the polypeptide encoded by the cDNA insert of the DNA45416-1251 vector deposited on Feb. 5, 1998 as ATCC Deposit No. 209620.

In yet another embodiment, the invention provides chimeric molecules comprising a PRO301 or PRO362 polypeptide fused to a heterologous polypeptide or amino acid sequence. An example of such a chimeric molecule comprises a PRO301 or PRO362 polypeptide fused to an epitope tag sequence or a Fc region of an immunoglobulin.

In yet another embodiment, the invention provides an expressed sequence tag (EST) comprising the nucleotide sequences identified as: DNA35936 (SEQ ID NO: 3) in FIG. 4A, consen01 (SEQ ID NO: 4) in FIG. 4B and consen02 (DNA42257)(SEQ ID NO: 5).

In another embodiment, the present invention provides an isolated antibody which binds a PRO301 or PRO362 polypeptide. In one aspect, the antibody mimics the activity of a PRO301 or PRO362 polypeptide (an agonist antibody) or conversely the antibody inhibits or neutralizes the activity of a PRO301 or PRO362 polypeptide (antagonist antibody). In another aspect, the antibody is a monoclonal antibody, which preferably contains nonhuman complementarity determining region (CDR) residues and human framework region (FR) residues. The antibody may be labeled and/or immobilized on a solid support. In a further aspect, the antibody is affinity matured, an antibody fragment, a single-chain antibody, or an anti-idiotypic antibody.

In another embodiment, the invention provides a composition containing a PRO301 or PRO362 polypeptide or an agonist or antagonist antibody in admixture with a carrier or excipient. In one aspect, the composition contains a therapeutically affective amount of the peptide or antibody. In another aspect, when the composition contains an inflammation stimulating molecule, the composition is useful for: (a) increasing infiltration of inflammatory cells into a tissue of a mammal in need thereof, (b) stimulating or enhancing an immune response in a mammal in need thereof, or (c) increasing the proliferation of T-lymphocytes in a mammal in need thereof in response to an antigen. In a further aspect, when the composition contains an inflammatory inhibiting molecule, the composition is useful for: (a) decreasing infiltration of inflammatory cells into a tissue of a mammal in need thereof, (b) inhibiting or reducing an inflammatory response in a mammal in need thereof, or (c) decreasing the proliferation of T-lymphocytes in a mammal in need thereof in response to an antigen. In another aspect, the composition contains a further active ingredient, which may, for example, be a further antibody or a cytotoxic or chemotherapeutic agent. Preferably, the composition is sterile.

In a further embodiment, the invention concerns nucleic acid encoding an anti-PRO301 and anti-PRO362 antibody, and vectors and recombinant host cells comprising such nucleic acid. In a still further embodiment, the invention concerns a method for producing such an antibody by culturing a host cell transformed with nucleic acid encoding the antibody under conditions such that the antibody is expressed, and recovering the antibody from the cell culture.

BRIEF DESCRIPTION OF THE DRAWINGS

FIGS. 1A and 1B show a comparison between the polypeptides encoded by A33 antigen (SEQ ID NO: 6), DNA40628 (SEQ ID NO: 1), DNA45416 (SEQ ID NO: 2), DNA35638 (SEQ ID NO: 9) and JAM (SEQ ID NO: 10).

FIG. 2 shows the derived amino acid sequence (SEQ ID NO: 1) of a native sequence PRO301 polypeptide. This polypeptide is 299 amino acids long, having signal sequence at residue 1 to 27, an extracellular domain at residue 28 to about 235, Ig superfamily homology at residue 94 to 235, a potential transmembrane domain at residue 236 to about 258, and an intracellular domain at about residue 259 to 299.

FIG. 3 shows the amino acid sequence (SEQ ID NO: 2) derived from nucleotides 119-1081 of the nucleotide sequence shown in FIGS. 6A and 6B (DNA45416, SEQ ID NO: 7). Also shown in FIG. 3 as underlines are the locations of a glycosoaminoglycan site and a transmembrane domain.

FIG. 4A shows the consensus assembly DNA35936 (SEQ ID NO: 3), and FIG. 4B shows consen01 (SEQ ID NO: 4) which were both used in the isolation of DNA40628 (SEQ ID NO: 11). FIG. 4C shows consen02 (DNA42257) (SEQ ID NO: 5) which was used in the isolation of DNA45416 (SEQ ID NO: 7).

FIG. 5 shows the nucleotide sequence of a native sequence DNA40628 cDNA (SEQ ID NO: 11), which is a native sequence PRO301 cDNA also designated as "UNQ264" and/or "DNA40628-1216".

FIGS. 6A, 6B and 6C show a nucleotide sequence DNA45416 (SEQ ID NO: 7) which is a native sequence PRO362 cDNA also designated as "UNQ317" and/or "DNA45416-1251". Also presented is the initiator methionine and the protein translation for a full-length PRO362 polypeptide (SEQ ID NO: 2).

FIG. 7 shows the nucleotide sequence (SEQ ID NO: 8) of a native sequence PRO245 cDNA, wherein the nucleotide sequence is designated as "UNQ219" and/or "DNA35638".

FIG. 8 shows the oligonucleotide sequences OLI2162 (35936.f1)(SEQ ID NO: 12), OLI2163 (35936.p1)(SEQ ID NO: 13), OLI2164 (35936.f2)(SEQ ID NO: 14), OLI2165 (35936.r1) (SEQ ID NO: 15), OLI2166 (35936.f3)(SEQ ID NO: 16), OLI2167 (35936.r2)(SEQ ID NO: 17) which were used in the isolation of DNA40628.

FIGS. 9A and 9B show a double stranded representation of the DNA42257 (consen02) (SEQ ID NO: 5) along with the locations of five oligonucleotide primers, showed in underline, all used in the isolation of DNA45416 (SEQ ID NO: 7). The oligonucleotides depicted are: 42257.f1 (SEQ ID NO: 18), 42257.f2 (SEQ ID NO: 19), 42257.r1 (SEQ ID NO: 20), 42257.r2 (SEQ ID NO: 21) and 42257.p1 (SEQ ID NO: 22).

FIGS. 10A and 10B describe the Blast score, match and percent homology alignment between 2 overlapping fragments of DNA40628 and A33_HUMAN, a human A33 antigen precursor. FIG. 10A compares the coded residues beginning at nucleotide position 121 to 816 of DNA40628 (SEQ ID NO: 23) with the coded residues beginning at nucleotides 17 to 284 of A33_HUMAN (SEQ ID NO: 24); FIG. 10B compares the coded residues beginning at nucleotides 112 to 810 (SEQ ID NO: 25) with the coded residues beginning at nucleotides 12 to 284 (SEQ ID NO: 26), respectively.

FIG. 11 shows the derived amino acid sequence of a native sequence PRO245 polypeptide (SEQ ID NO: 9) encoded by the nucleotide sequence of FIG. 7 (DNA35638, SEQ ID NO: 8).

FIG. 12 indicates a 25.3% identity between the amino acid sequence encoded by DNA40628 (SEQ ID NO: 1) and A33 antigen (SEQ ID NO: 6).

FIG. 13 indicates a 20.8% identity between the amino acid sequence encoded by DNA45416 (SEQ ID NO: 2) and A33 antigen (SEQ ID NO: 6).

FIG. 14 indicates a 24.3% identity between the amino acid sequence encoded by DNA35638 (SEQ ID NO: 9) and A33 antigen (SEQ ID NO: 6).

FIG. 15 indicates a 67.6% identity between the amino acid sequence encoded by DNA40628 (SEQ ID NO: 1) and JAM (SEQ ID NO: 10).

FIG. 16 indicates a 23.3% identity between the amino acid sequence encoded by DNA45416 (SEQ ID NO: 2) and JAM (SEQ ID NO: 10).

FIG. 17 indicates a 34.2% identity between the amino acid sequence encoded by DNA35638 (SEQ ID NO: 29) and JAM (SEQ ID NO: 10).

FIG. 18 indicates a 26% identity between the amino acid sequence encoded by A33 antigen (SEQ ID NO: 6) and JAM (SEQ ID NO: 10).

FIG. 19 shows the results of the dot blot hybridization procedure described in Example 8

FIG. 20 shows the results of the Taqman MRNA expression assay described in Example 9

FIG. 21 shows the binding of protein encoded by DNA40628 to human neutrophils as described in Example 7.

DETAILED DESCRIPTION OF THE PREFERRED EMBODIMENTS

I. Definitions

The terms "PRO301", "PRO362, "PRO245", or "PRO301 polypeptide," "PRO362 polypeptide," "PRO245 polypeptide" and "cancer associated antigen" when used herein encompass native sequence PRO301, PRO362 or PRO245, respectively and variants thereof (which are further defined herein). The PRO301, PRO362 or PRO245 may be isolated from a variety of sources, such as from human tissue types or from another source, or prepared by recombinant or synthetic methods.

The terms "inflammatory disease" means a disease in which a component of the immune system of a mammal causes, mediates or otherwise contributes to an inflammatory response contributing to the morbidity in the mammal. Also included are diseases in which stimulation or intervention of the inflammatory response has an ameliorative effect on progression of the disease. Included within this term are immune-mediated inflammatory diseases.

The term "T-cell mediated" disease means a disease in which T cells directly or indirectly mediate or otherwise contribute to the morbidity in a mammal. The T cell mediated disease by be associated with cell mediated effects, lymphokine mediated effects, etc. and even effects associated with B cells if the B cells are stimulated, for example; by the lymphokines secreted by T cells.

Examples of immune-related and inflammatory diseases, some of which are T cell mediated, which can be treated according to the invention include: inflammatory bowel disease, systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonias, idiopathic pulmonary fibrosis and hypersensitivity pneumonitis, transplantation associated diseases including graft rejection and graft-verus host disease.

"Tumor", as used herein, refers to all neoplastic cell growth and proliferation whether malignant or benigh, and all pre-cancerous cells and tissues.

The terms "cancer" and "cancerous" refer to or describe the physiological condition in mammals that is typcially characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures.

Those in need of treatment include those already with the disorder as well as those in which the disorder is to be prevented. In treatment of an immune related disease, a therapeutic agent may directly decrease or increase the magnitude of response of a component of the immune response, or render the disease more susceptible to treatment by other therapeutic agents, e.g., antibiotics, antifungals, anti-inflammatory agents, chemotherapeutics, etc.

The "pathology" of an immune related disease includes all phenomena that compromise the well-being of the patient. This includes, without limitation, abnormal or uncontrollable cell growth (neutrophilic, eosinophilic, monocytic, lymphocytic cells), antibody production, autoantibody production, complement production, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into cellular spaces, etc.

The terms "mammal" as used herein refers to any mammal classified as a mammal, including humans, domestic and farm animals, and zoo, sports or pet animals such horses, pigs, cattle, dogs, cats and ferrets, etc. In a preferred embodiment of the invention, the mammal is a human.

Administration "in combination with" one or more further therapeutic agents includes simultaneous (concurrent) and consecutive administration in any order.

The term "cytotoxic agent" as used herein refers to a substance that inhibits or prevents the function of cells and/or causes destruction of cells. The term is intended to include radioactive isotopes (e.g. $I^{131}$, $I^{125}$, $y^{90}$ and $Re^{186}$), chemotherapeutic agents, and toxins such a enzymatically active toxins of bacterial, fungal, plant or animal origin, or fragments thereof.

A "chemotherapeutic agent" is a compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (Taxol®, Bristol-Myers Squibb Oncology, Princeton, N.J.) and doxetaxel (Taxotere®, Rhone-Poulenc Roher, Antony, France), toxotere, methotrexate, cisplatin, melphalan, vinblastine, bleomycin, etoposide, ifosfamide, mitomycin C, mitoxantrone, vincristine (Loucristine), vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormonal action on tumors such as tamoxifen and onapristone.

A "growth inhibitory agent" when used herein refers to a compound or composition which inhibits growth of a cell, especially cancers cells expressing or overexpressing any of the genes identified herein, either in vitro or in vivo. Thus, the growth inhibitory agent is one which significantly reduces the percentage of cells expressing or overexpressing such genes in S phase. Examples of growth inhibitory agents include agents that block cell cycle progression (at a place other than S phase), such as agents that induce G1 arrest and M-phase arrest. Classical M-phase blockers include the vinca alkaloids (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such tamoxifen, prednisone, dacarbazine, mechlorethamine, cisplatin, methotrexate, 5-fluorouracil, and ara-C.

Further information can be found in *The Molecular Basis of Cancer*, Mendelsohn and Israel, eds., Chapter 1, entitled "Cell cycle regulation, oncogens, and antineoplastic drugs" by Murakami et al. (W B Saunders, Philadelphia, 1995), especially page 13.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone, parathyroid hormone, thyroxine, insulin, proinsulin, relaxin, prorelaxin, glycoprotein hormones such as follicle stimulating hormone (FSH), thyroid stimulating hormone (TSH), and luteinizing hormone (LH), hepatic growth factor, fibroblast growth factor, prolactin, placental lactogen, tumor necrosis factor-α and -β, mullerian-inhibiting substance, mouse gonadotropin-associated peptide, inhibin, activin, vascular endothelial growth factor, integrin, thrombopoietin (TPO), nerve growth factors such as NGF-β, platelet-growth factor, transforming growth factors (TGFs) such as TGF-α and TGF-β, insulin-like growth factor-I and -II, erythropoietin (EPO), osteoinductive factors, interferons such as interferon-α, -β, and -γ, colony stimulating factors (CSFs) such as macrophage-CSF (M-CSF), granulocyte-macrophage-CSF (GM-CSF), and granulocyte-CSF (G-CSF), interleukins (ILs) such as IL-1, IL-1α, IL-2, IL-3, IL-4, IL-5, IL-6, IL-7, IL-8, IL-9, IL-11, IL-12, a tumor necrosis factor such as THF-α or TNF-β, and other polypeptide factors including LIF and kit ligand (KL). As used herein, the term cytokine includes proteins from natural sources or from recombinant cell culture and biologically active equivalents of the native sequence cytokines.

"Therapeutically effective amount" is the amount of active PRO301, PRO362 or PRO245 antagonist or agonist which is required to achieve a measureable inhibition or stimulation, as the case may be, of the inflammatory response.

A "native sequence PRO301, PRO362 or PRO245", comprises a polypeptide having the same amino acid sequence as a PRO301, PRO362 or PRO245, respectively, derived from nature. Such native sequence PRO301, PRO362 or PRO245 can be isolated from nature or can be produced by recombinant or synthetic means. The term "native sequence PRO301", "native sequence PRO362" or "native sequence PRO245" specifically encompasses naturally-occurring truncated or secreted forms of PRO301, PRO362 or PRO245, respectively (e.g., an extracellular domain sequence), naturally-occurring variant forms (e.g., alternatively spliced forms) and naturally-occurring allelic variants of PRO301, PRO362 or PRO245, respectively.

In one embodiment, the native sequence PRO301 is a mature or full-length native sequence PRO301 comprising amino acids 1 to 299 of FIG. 2 (SEQ ID NO: 1), with or without the N-terminal signal sequence, with or without the initiating methionine at position 1, with or without the potential transmembrane domain at position 236 to about 258, and with or without the intracellular domain at about position 259 to 299.

In another embodiment, the native sequence PRO362 polypeptide is an extracellular domain of the full-length PRO362 protein comprising amino acids 1 to X of the amino acid sequence shown in FIG. 3 (SEQ ID NO: 2) where X is any amino acid residue 271-280. Optionally, the PRO362 polypeptide is obtained or obtainable by expressing the polypeptide encoded by the cDNA insert of the vector DNA45416-1251 deposited on Feb. 5, 1998 as ATCC Deposit No.: 209620.

In yet another embodiment, the native sequence PRO245 polypeptide is a mature or full-length native sequence PRO245 polypeptide comprising amino acids 1 to 312 of FIG. 11 (SEQ ID NO: 9).

The "PRO301 or PRO362 extracellular domain" or "PRO301 or PRO362 ECD" refers to a form of the PRO301 or PRO362 polypeptide, respectively, which is essentially free of the transmembrane and cytoplasmic domains of the respective full length molecules. Ordinarily, PRO301 ECD or PRO362 ECD will have less than 1% of such transmembrane and/or cytoplasmic domains and preferably, will have less than 0.5% of such domains. Optionally, PRO301 polypeptide ECD will comprise amino acid residues about 28 to about 235 of FIG. 2 (SEQ ID NO: 1), while PRO362 polypeptide ECD will comprise amino acid residues 1 to X of FIG. 3 (SEQ ID NO: 2), where X is any amino acid from 271-280. It will be understood that any transmembrane domain identified for the PRO301 or PRO362 polypeptides of the present invention is identified pursuant to criteria routinely employed in the art for identifying that type of hydrophobic domain. The exact boundaries of a transmembrane domain may vary but most likely by no more than about 5 amino acids at either end of the domain as initially identified. Accordingly, the PRO301 or PRO362 polypeptide ECD may optionally comprise amino acids 1 to X of FIG. 3 (SEQ ID NO: 2), wherein X is any one of amino acid residues 271 to 280 of FIG. 3 (SEQ ID NO: 2).

"PRO301 variant" or "PRO245 variant" means an active PRO301 as defined below having at least about 80% amino acid sequence identity to (a) a DNA molecule encoding a PRO301 polypeptide, with or without its native signal sequence, with or without the initiating methionine, with or without the potential transmembrane domain, and with or without the intracellular domain or (b) the complement of the DNA molecule of (a). In a particular embodiment, the PRO301 variant has at least about 80% amino acid sequence homology with the PRO301 having the deduced amino acid sequence shown in FIG. 1 (SEQ ID NO: 1) for a full-length native sequence PRO301. Such PRO301 variants include, for instance, PRO301 polypeptides wherein one or more amino acid residues are added, or deleted, at the N- or C-terminus of the sequence of FIG. 2 (SEQ ID NO: 1). Preferably, the nucleic acid or amino acid sequence identity is at least about 85%, more preferably at least about 90%, and even more preferably at least about 95%.

"PRO362 variant" means an active PRO362 polypeptide as defined below having at least about 80% amino acid sequence identity with the PRO362 polypeptide having the deduced amino acid sequence shown in FIG. 3 (SEQ ID NO: 2) for a full-length native sequence PRO362 polypeptide. Such PRO362 polypeptide variants include, for instance, PRO362 polypeptides wherein one or more amino acid residues are added, or deleted, at the N- or C-terminus of the sequence of FIG. 3 (SEQ ID NO: 2). Ordinarily, a PRO362 polypeptide variant will have at least about 80% amino acid sequence identity, preferably at least about 85% amino acid sequence identity, more preferably at least about 90% amino acid sequence identity and even more preferably at least about 95% amino acid sequence identity with the amino acid sequence of FIG. 3 (SEQ ID NO: 2).

"Percent (%) amino acid sequence identity" with respect to the PRO301, PRO362 or PRO245 sequences identified herein is defined as the percentage of amino acid residues in a candidate sequence that are identical with the amino acid residues in the PRO301, PRO362 or PRO245 sequence, respectively, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Percent (%) nucleic acid sequence identity" with respect to the PRO301-, PRO362- or PRO245-encoding sequences identified herein (e.g., DNA40628, DNA45416, DNA35638) is defined as the percentage of nucleotides in a candidate sequence that are identical with the nucleotides in the PRO301-, PRO362- or PRO245-encoding sequence, respectively, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO301 natural environment will not be present. Ordinarily, however, isolated polypeptide will be prepared by at least one purification step.

An "isolated" DNA40628 nucleic acid molecule is a nucleic acid molecule that is identified and separated from at least one contaminant nucleic acid molecule with which it is ordinarily associated in the natural source of the DNA40628 nucleic acid. An isolated DNA40628 nucleic acid molecule is other than in the form or setting in which it is found in nature. Isolated DNA40628 nucleic acid molecules therefore are distinguished from the DNA40628 nucleic acid molecule as it exists in natural cells. However, an isolated DNA40628 nucleic acid molecule includes DNA40628 nucleic acid molecules contained in cells that ordinarily express DNA40628 where, for example, the nucleic acid molecule is in a chromosomal location different from that of natural cells.

An "isolated" PRO301-PRO362- or PRO245-polypeptide encoding nucleic acid molecule is a nucleic acid molecule that is identified and separated from at least one contaminant nucleic acid molecule with which it is ordinarily associated in the natural source of the PRO301-PRO362- or PRO245 polypeptide encoding nucleic acid. An isolated PRO301-PRO362- or PRO245 polypeptide encoding nucleic acid molecule is other than in the form or setting in which it is found in nature. Isolated PRO301-PRO362- or PRO245 polypeptide encoding nucleic acid molecules therefore are distinguished from the DNA40628 nucleic acid molecule as it exists in natural cells. However, an isolated PRO301-PRO362- or PRO245 polypeptide encoding nucleic acid molecule includes PRO301-PRO362- or PRO245 polypeptide encoding nucleic acid molecules contained in cells that ordinarily express PRO301-PRO362- or PRO245 polypeptide encoding where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-PRO301, anti-PRO362 or anti-PRO245 monoclonal antibodies (including agonist, antagonist, and neutralizing antibodies) and anti-PRO301, anti-PRO362 or anti-PRO245 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" for the purposes herein refers to form(s) of PRO301, PRO362 or PRO245 which retain the biologic and/or immunologic activities of native or naturally-occurring PRO301. A preferred activity is the ability to bind to and affect, e.g., block or otherwise modulate, an activity of antigen binding. The activity preferably involves the regulation, activity of cancer and or viral associated antigens.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42C; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC sodium chloride/sodium citrate) and 50% formamide at 55C, followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a polypeptide of the invention fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" in the context of variants of the polypeptide of the invention refers to form(s) of proteins of the invention which retain the biologic and/or immunologic activities of a native or naturally-occurring polypeptide of the invention.

"Biological activity" in the context of an antibody or another molecule that can be identified by the screening assays disclosed herein (e.g. an organic or inorganic small molecule, peptide, etc.) is used to refer to the ability of such molecules to induce or inhibit infiltration of inflammatory cells into a tissue, to stimulate or inhibit T-cell proliferation and to stimulate or inhibit lymphokine release by cells. Another preferred activity is increased vascular permeability or the inhibition thereof.

The term "antagonist" is used in the broadest sense, and includes any molecule that partially or fully blocks, inhibits, or neutralizes a biological activity of a native polypeptide of the invention disclosed herein. In a similar manner, the term "agonist" is used in the broadest sense and includes any molecule that mimics a biological activity of a native polypeptide of the invention disclosed herein. Suitable agonist or antagonist molecules specifically include agonist or antagonist antibodies or antibody fragments, fragments or amino acid sequence variants of native polypeptides of the invention, peptides, small organic molecules, etc.

A "small molecule" is defined herein to have a molecular weight below about 600 daltons.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. The term "antibody" is used in the broadest sense and specifically covers, without limitation, intact monoclonal antibodies, polyclonal antibodies, multispecific antibodies (e.g. bispecific antibodies) formed from at least two intact antibodies, and antibody fragments so long as they exhibit the desired biological activity.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., *NIH Publ. No.*91-3242, Vol. I, pages 647-669 (1991)). The constant domains are not involved directly in binding an antibody to an antigen, but exhibit various effector functions, such as participation of the antibody in antibody-dependent cellular toxicity.

"Antibody fragments" comprise a portion of an intact antibody, preferably the antigen binding or variable region of the intact antibody. Examples of antibody fragments include Fab, Fab, F(ab')$_2$, and Fv fragments; diabodies; linear antibodies (Zapata et al., *Protein Eng.* 8(10):1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment. The designation "Fc" reflects the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "monoclonal antibody" as used herein refers to an antibody obtained from a population of substantially homogeneous antibodies, ie., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 [1975], or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 [1991] and Marks et al., *J. Mol. Boil.*, 222: 581-597 (1991), for example. See also U.S. Pat. Nos. 5,750,373, 5,571,698, 5,403,484 and 5,223,409 which describe the preparation of antibodies using phagemid and phage vectors.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which several or all residues from a complementarity-determining region (CDR) of the recipient are replaced by residues from a CDR of a non-human species (donor antibody) such as mouse, rat or rabbit having the desired specificity, affinity, and capacity. In some instances, certain Fv framework region (FR) residues of the human immunoglobulin can also be replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321: 522-525 (1986); Reichmann et al, *Nature*, 332: 323-329 [1988]; and Presta, *Curr. Op. Struct. Biol.*, 2: 593-596 (1992). The humanized antibody includes a "primatized" antibody where the antigen-binding region of the antibody is derived from an antibody produced by immunizing macaque monkeys with the antigen of interest. Antibodies containing residues from Old World monkeys are also possible within the invention. See, for example, U.S. Pat. Nos. 5,658,570; 5,693,780; 5,681,722; 5,750,105; and 5,756,096.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90: 6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the compound of the invention will be purified (1) to greater than 95% by weight of the compound as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated compound, e.g. antibody or polypeptide, includes the compound in situ within recombinant cells since at least one component of the compound's natural environment will not be present. Ordinarily, however, isolated compound will be prepared by at least one purification step.

The word "label" when used herein refers to a detectable compound or composition which is conjugated directly or indirectly to the compound, e.g. antibody or polypeptide, so as to generate a "labeled" compound. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the compound of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG4 subtypes, IgA (including IgA-1 and IgA-2), IgE, IgD or IgM.

II. Compositions and Methods of the Invention

A. Preparation of the PRO301, PRO362 or PRO245 Polypeptides

1. Full-length PRO301, PRO362 or PRO245 Polypeptides

The present invention provides newly identified and isolated nucleotide sequences encoding polypeptides referred to in the present application as PRO301, PRO362 or PRO245. In particular, Applicants have identified and isolated cDNA encoding a PRO301, PRO362 or PRO245 polypeptide, as disclosed in further detail in the Examples below. Using BLAST and FastA sequence alignment computer programs, Applicants found that a full-length native sequence PRO301 (FIG. 2, SEQ ID NO: 1), PRO362 (FIG. 3, SEQ ID NO: 3) and PRO245 (FIG. 11, SEQ ID NO: 9) have significant homology to both A33 antigen and JAM. (See FIGS. 1, 12-18). Accordingly, it is presently believed that PRO301 disclosed in the present application is a newly identified member of the A33 antigen protein family and may be associated with inflammatory disorders such as inflammatory bowel disease as well as human neoplastic diseases such as colorectal cancer.

2. PRO301, PRO362 or PRO245 Variants

In addition to the full-length native sequence PRO301, PRO362 or PRO245 described herein, it is contemplated that PRO301, PRO362 or PRO245 variants can be prepared. PRO301, PRO362 or PRO245 variants can be prepared by introducing appropriate nucleotide changes into the PRO301, PRO362 or PRO245 DNA, respectively, or by synthesis of the desired PRO301, PRO362 or PRO245 polypeptides. Those skilled in the art will appreciate that amino acid changes may alter post-translational processes of the PRO301, PRO362 or PRO245, such as changing the number or position of glycosylation sites or altering the membrane anchoring characteristics.

Variations in the native full-length sequence PRO301, PRO362 or PRO245 or in various domains of the PRO301, PRO362 or PRO245 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO301, PRO362 or PRO245 that results in a change in the amino acid sequence of the PRO301, PRO362 or PRO245 as compared with the native sequence PRO301, PRO362 or PRO245. Optionally the variation is by substitution of at least one amino acid with any other amino acid in one or more of the domains of the PRO301, PRO362 or PRO245. Guidance in determining which amino acid residue may be inserted, substituted or deleted without adversely affecting the desired activity may be found by comparing the sequence of the PRO301, PRO362 or PRO245 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO301 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

3. Modifications of PRO301, PRO362 or PRO245

Covalent modifications of PRO301, PRO362 or PRO245 are included within the scope of this invention. One type of covalent modification includes reacting targeted amino acid residues of the PRO301, PRO362 or PRO245 with an organic derivatizing agent that is capable of reacting with selected side chains or the N- or C-terminal residues of the PRO301, PRO362 or PRO245. Derivatization with bifunctional agents is useful, for instance, for crosslinking PRO301 to a water-insoluble support matrix or surface for use in the method for purifying anti-PRO301 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO301, PRO362 or PRO245 polypeptide included within the scope of this invention comprises altering the native glycosylation pattern of the polypeptide. "Altering the native glycosylation pattern" is intended for purposes herein to mean deleting one or more carbohydrate moieties found in native sequence PRO301, PRO362 or PRO245, and/or adding one or more glycosylation sites that are not present in the native sequence PRO301, PRO362 or PRO245, and/or alteration of the ratio and/or composition of the sugar residues attached to the glycosylation site(s).

Addition of glycosylation sites to the PRO301, PRO362 or PRO245polypeptide may be accomplished by altering the amino acid sequence. The alteration may be made, for example, by the addition of, or substitution by, one or more serine or threonine residues to the native sequence PRO301, PRO362 or PRO245 (for O-linked glycosylation sites). The PRO301, PRO362 or PRO245 amino acid sequence may optionally be altered through changes at the DNA level, particularly by mutating the DNA encoding the PRO301, PRO362 or PRO245 polypeptide at preselected bases such that codons are generated that will translate into the desired amino acids.

Another means of increasing the number of carbohydrate moieties on the PRO301, PRO362 or PRO245 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the PRO301, PRO362 or PRO245 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO301, PRO362 or PRO245 comprises linking the PRO301, PRO362 or PRO245 polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The PRO301, PRO362 or PRO245 of the present invention may also be modified in a way to form a chimeric molecule comprising PRO301, PRO362 or PRO245 fused to another, heterologous polypeptide or amino acid sequence. In one embodiment, such a chimeric molecule comprises a fusion of the PRO301, PRO362 or PRO245 with a tag polypeptide which provides an epitope to which an anti-tag antibody can selectively bind. The epitope tag is generally placed at the amino- or carboxyl-terminus of the PRO301, PRO362 or PRO245. The presence of such epitope-tagged forms of the PRO301, PRO362 or PRO245 can be detected using an antibody against the tag polypeptide. Also, provision of the epitope tag enables the PRO301, PRO362 or PRO245 to be readily purified by affinity purification using an anti-tag antibody or another type of affinity matrix that binds to the epitope tag. In an alternative embodiment, the chimeric molecule may comprise a fusion of the PRO301, PRO362 or PRO245 with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3 C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

4. Production and Isolation of PRO301, PRO362 or PRO245

The description below relates primarily to production of PRO301, PRO362 or PRO245 by culturing cells transformed or transfected with a vector containing PRO301, PRO362 or PRO245 nucleic acid. It is, of course, contemplated that alternative methods, which are well known in the art, may be employed to prepare PRO301, PRO362 or PRO245. For instance, the PRO301, PRO362 or PRO245 sequence, or portions thereof, may be produced by direct peptide synthesis using solid-phase techniques [see, e.g., Stewart et al., *Solid-Phase Peptide Synthesis*, W. H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO301, PRO362 or PRO245 may be chemically synthesized separately and combined using chemical or enzymatic methods to produce the full-length PRO301, PRO362 or PRO245.

a. Isolation of DNA Encoding PRO301, PRO362 or PRO245

DNA encoding PRO301, PRO362 or PRO245 may be obtained from a cDNA library prepared from tissue believed to possess the PRO301, PRO362 or PRO245 mRNA and to express it at a detectable level. Accordingly, human PRO301, PRO362 or PRO245 DNA can be conveniently obtained from a cDNA library prepared from human tissue, such as described in the Examples. The PRO301-, PRO362- or PRO245-encoding gene may also be obtained from a genomic library or by oligonucleotide synthesis.

Libraries can be screened with probes (such as antibodies to the PRO301, PRO362 or PRO245 or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO301, PRO362 or PRO245 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$p-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as Gen-Bank or other private sequence databases. Sequence identity (at either the amino acid or nucleotide level) within defined regions of the molecule or across the full-length sequence can be determined through sequence alignment using computer software programs such as BLAST, BLAST-2, ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of MRNA that may not have been reverse-transcribed into cDNA.

b. Selection and Transformation of Host Cells

Host cells are transfected or transformed with expression or cloning vectors described herein for PRO301, PRO362 or PRO245 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general., principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for PRO301-, PRO362- or PRO245-encoding vectors. *Saccharomyces cerevisiae* is a commonly used lower eukaryotic host microorganism.

Suitable host cells for the expression of glycosylated PRO301, PRO362 or PRO245 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

C. Selection and Use of a Replicable Vector

The nucleic acid (e.g., cDNA or genomic DNA) encoding PRO301, PRO362 or PRO245 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO301, PRO362 or PRO245 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO30 1, PRO362 or PRO245 DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces*"—factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO301. PRO362 or PRO245 nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO301, PRO362 or PRO245 nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding PRO301, PRO362 or PRO245.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO301, PRO362 or PRO245 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO301, PRO362 or PRO245 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO301, PRO362 or PRO245 coding sequence, but is preferably located at a site 5' from the promoter.

Expression vectors used in eukaryotic host cells (yeast, fungi, insect, plant, animal., human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO301, PRO362 or PRO245.

Still other methods, vectors, and host cells suitable for adaptation to the synthesis of PRO301, PRO362 or PRO245 in recombinant vertebrate cell culture are described in Gething et al., *Nature*, 293:620-625 (1981); Mantei et al., *Nature*, 281:40-46 (1979); EP 117,060; and EP 117,058.

d. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO301, PRO362 or PRO245 polypeptide or against a synthetic peptide based on the DNA sequences provided herein or against exogenous sequence fused to PRO301, PRO362 or PRO245 DNA and encoding a specific antibody epitope.

e. Purification of Polypeptide

Forms of PRO301, PRO362 or PRO245 may be recovered from culture medium or from host cell lysates. If membrane-bound, it can be released from the membrane using a suitable detergent solution (e.g. Triton-X 100) or by enzymatic cleavage. Cells employed in expression of PRO301, PRO362 or PRO245 can be disrupted by various physical or chemical means, such as freeze-thaw cycling, sonication, mechanical disruption, or cell lysing agents.

It may be desired to purify PRO301, PRO362 or PRO245 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO301, PRO362 or PRO245. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO301, PRO362 or PRO245 produced.

2. Tissue Distribution

The location of tissues expressing the polypeptides of the invention can be identified by determining mRNA expression in various human tissues. The location of such genes provides information about which tissues are most likely to be affected by the stimulating and inhibiting activities of the polypeptides of the invention. The location of a gene in a specific tissue also provides sample tissue for the activity blocking assays discussed below.

Gene expression in various tissues may be measured by conventional Southern blotting, Northern blotting to quantitate the transcription of mRNA (Thomas, *Proc. Natl. Acad. Sci. USA*, 77:5201-5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of a polypeptide of the invention or against a synthetic peptide based on the DNA sequences encoding the polypeptide of the invention or against an exogenous sequence fused to a DNA encoding a polypeptide of the invention and encoding a specific antibody epitope. General techniques for generating antibodies, and special protocols for Northern blotting and in situ hybridization are provided below.

3. Antibody Binding Studies

The activity of the polypeptides of the invention can be further verified by antibody binding studies, in which the ability of anti-PRO301, anti-PRO362 or anti-PRO245 antibodies to inhibit the effect of the PRO301, PRO362 or PRO245 polypeptides on tissue cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

4. Cell-Based Assays

Cell-based assays and animal models for immune related diseases can be used to further understand the relationship between the genes and polypeptides identified herein and the development and pathogenesis of immune related disease.

In a different approach, cells of a cell type known to be involved in a particular immune related disease are transfected with the cDNAs described herein, and the ability of these cDNAs to stimulate or inhibit immune function is analyzed. Suitable cells can be transfected with the desired gene, and monitored for immune function activity. Such transfected cell lines can then be used to test the ability of poly- or monoclonal antibodies or antibody compositions to inhibit or stimulate immune function, for example to modulate T-cell proliferation or inflammatory cell infiltration. Cells transfected with the coding sequences of the genes identified herein can further be used to identify drug candidates for the treatment of immune related diseases.

In addition, primary cultures derived from transgenic animals (as described below) can be used in the cell-based assays herein, although stable cell lines are preferred. Techniques to derive continuous cell lines from transgenic animals are well known in the art (see, e.g. Small et al., *Mol. Cell. Biol.* 5, 642-648 [1985]).

One suitable cell based assay is the mixed lymphocyte reaction (MLR). *Current Protocols in Immunology*, unit 3.12; edited by J E Coligan, A M Kruisbeek, D H Marglies, E M Shevach, W Strober, National Institutes of Health, Published by John Wiley & Sons, Inc. In this assay, the ability of a test compound to stimulate the proliferation of activated T cells is assayed. A suspension of responder T cells is cultured with allogeneic stimulator cells and the proliferation of T cells is measured by uptake of tritiated thymidine. This assay is a general measure of T cell reactivity. Since the majority of T cells respond to and produce IL-2 upon activation, differences in responsiveness in this assay in part reflect differences in IL-2 production by the responding cells. The MLR results can be verified by a standard lymphokine (IL-2) detection assay. *Current Protocols in Immunology*, supra, 3.15, 6.3.

A proliferative T cell response in an MLR assay may be due to a mitogenic response or may be due to a stimulatory response by the T cells. Additional verification of the T cell stimulatory activity of the polypeptides of the invention can be obtained by a costimulation assay. T cell activation requires an antigen specific signal mediated through the major histocompatability complex (MHC) and a costimulatory signal mediated through a second ligand binding interaction, for example, the B7(CD80, CD86)/CD28 binding interaction. CD28 crosslinking increases lymphokine secretion by activated T cells. T cell activation has both negative and positive controls through the binding of ligands which have a negative or positive effect. CD28 and CTLA-4 are related glycoproteins in the Ig superfamily which bind to B7. CD28 binding to B7 has a positive costimulation effect of T cell activation; conversely, CTLA-4 binding to B7 has a negative T cell deactivating effect. Chambers, C. A. and Allison, J. P., *Curr. Opin. Immunol.* (1997) 9:396. Schwartz, R. H., *Cell* (1992) 71:1065; Linsey, P. S. and Ledbetter, J. A., *Annu. Rev. Immunol.* (1993) 11:191; June, C. H. et al., *Immunol. Today* (1994) 15:321; Jenkins, M. K., *Immunity* (1994) 1:405. In a costimulation assay, the polypeptides of the invention are assayed for T cell costimulatory or inhibitory activity.

Polypeptides of the invention, as well as other compounds of the invention, which are stimulators (costimulators) of T cell proliferation, as determined by MLR and costimulation assays,for example, are useful in treating immune related diseases characterized by poor, suboptimal or inadequate immune function. These diseases are treated by stimulating the proliferation and activation of T cells (and T cell mediated immunity) and enhancing the immune response in a mammal through administration of a stimulatory compound, such as the stimulating polypeptides of the invention. The stimulating polypeptide may be a PRO301, PRO362 or PRO245 polypeptide or an agonist antibody therefor. Immunoadjuvant therapy for treatment of tumors, described in more detail below, is an example of this use of the stimulating compounds of the invention. Antibodies which bind to inhibitory polypeptides function to enhance the immune response by removing the inhibitory effect of the inhibiting polypeptides. This effect is seen in experiments using anti-CTLA-4 antibodies which enhance T cell proliferation, presumably by removal of the inhibitory signal caused by CTLA-4 binding. Walunas, T. L. et al., *Immunity* (1994) 1:405. This use is also validated in experiments with 4-1BB glycoprotein, a member of the tumor necrosis factor receptor family which binds to a ligand (4-1BBL) expressed on primed T cells and signals T cell activation and growth. Alderson, M. E. et al., *J. Immunol.* (1994) 24:2219. Inhibition of 4-1BB binding by treatment with an anti-4-1BB antibody increases the severity of graft-versus-host disease and may be used to eradicate tumors. Hellstrom, I. and Hellstrom, K. E., *Crit. Rev. Immunol.* (1998) 18:1.

On the other hand, polypeptides of the invention, as well as other compounds of the invention, which are inhibitors of T cell proliferation/activation and/or lymphokine secretion, can be directly used to suppress the immune response. These compounds are useful to reduce the degree of the immune response and to treat immune related diseases characterized by a hyperactive, superoptimal., or autoimmune response. Alternatively, antibodies which bind to the stimulating polypeptides of the invention and block the stimulating effect of these molecules can be used to suppress the T cell mediated immune response by inhibiting T cell proliferation/activation and/or lymphokine secretion. Blocking the stimulating effect of the polypeptides suppresses the immune response of the mammal.

5. Animal Models

The results of the cell based in vitro assays can be further verified using in vivo animal models and assays for T-cell function. A variety of well known animal models can be used to further understand the role of the genes identified herein in the development and pathogenesis of immune related disease, and to test the efficacy of candidate therapeutic agents, including antibodies, and other antagonists of the native polypeptides, including small molecule antagonists. The in vivo nature of such models makes them particularly predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g. subcutaneous injection, tail vein injection, spleen implantation, intraperitoneal implantation, implantation under the renal capsule, etc.

Contact hypersensitivity is a simple in vivo assay of cell mediated immune function. In this procedure, epidermal cells are exposed to exogenous haptens which give rise to a delayed type hypersensitivity reaction which is measured and quantitated. Contact sensitivity involves an initial sensitizing phase followed by an elicitation phase. The elicitation phase occurs when the epidermal cells encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons, Inc., 1994, unit 4.2. See also Grabbe, S. and Schwarz, T, *Immun. Today* 19(1):37-44 (1998).

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in *Current Protocols in Immunology*, supra, unit 4.3.

An animal model for skin allograft rejection is a means of testing the ability of T cells to mediate in vivo tissue destruction which is indicative of and a measure of their role in anti-viral and tumor immunity. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology*, 2nd ed., W. E. Paul ed., Raven Press, N.Y., 1989, 889-992. A suitable procedure is described in detail in *Current Protocols in Immunology*, supra, unit 4.4. Other transplant rejection models which can be used to test the compounds of the invention are the allogeneic heart transplant models described by Tanabe, M.

et al., Transplantation (1994) 58:23 and Tinubu, S. A. et al., *J. Immunol.* (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multiple Sclerosis* (1995) 1:143. Both acute and relapsing-remitting models have been developed. The compounds of the invention can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al., *Molec. Med. Today* (1997) 554-561.

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The compounds of the invention can be tested for activity against autoimmune arthritis using the protocols described in Current Protocols in Immunology, above, units 15.5. See also the model using a monoclonal antibody to CD18 and VLA-4 integrins described in Issekutz, A. C. et al., *Immunology* (1996) 88:569.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compounds of the invention for activity and effectiveness in the treatment of asthma are described by Wolyniec, W. W. et al., *Am. J. Respir. Cell Mol. Biol.* (1998) 18:777 and the references cited therein.

Additionally, the compounds of the invention can be tested on animal models for psoriasis like diseases. Evidence suggests a T cell pathogenesis for psoriasis. The compounds of the invention can be tested in the scid/scid mouse model described by Schon, M. P. et al, *Nat. Med.* (1997) 3:183, in which the mice demonstrate histopathologic skin lesions resembling psoriasis. Another suitable model is the human skin/scid mouse chimera prepared as described by Nickoloff, B. J. et al., *Am. J. Path.* (1995) 146:580.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci USA* 82, 6148-615 [1985]); gene targeting in embryonic stem cells (Thompson et al., *Cell* 56, 313-321 [1989]); electroporation of embryos (Lo, *Mol. Cel. Biol.* 3, 1803-1814 [1983]); sperm-mediated gene transfer (Lavitrano et al., *Cell* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 623-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with the compounds of the invention to determine the extent of the T cell proliferation stimulation or inhibition of the compounds. In these experiments, blocking antibodies which bind to the polypeptide of the invention, prepared as described above, are administered to the animal and the effect on immune function is determined.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

6. Immuno Adjuvant Therapy

In one embodiment, compounds of the invention having an immunostimulatory effect can be used in immunoadjuvant therapy for the treatment of tumors (cancer). It is now well established that T cells recognize human tumor specific antigens. One group of tumor antigens, encoded by the MAGE, BAGE and GAGE families of genes, are silent in all adult normal tissues, but are expressed in significant amounts in tumors, such as melanomas, lung tumors, head and neck tumors, and bladder carcinomas. DeSmet, C. et al., (1996) *Proc. Natl. Acad. Sci. USA*, 93:7149. It has been shown that costimulation of T cells induces tumor regression and an antitumor response both in vitro and in vivo. Melero, I. et al., *Nature Medicine* (1997) 3:682; Kwon, E. D. et al., *Proc. Natl. Acad. Sci. USA* (1997) 94:8099; Lynch, D. H. et al., *Nature Medicine* (1997) 3:625; Finn, O. J. and Lotze, M. T., *J. Immunol.* (1998) 21:114. The stimulatory compounds of the invention can be administered as adjuvants, alone or together with a growth regulating agent, cytotoxic agent or chemotherapeutic agent, to stimulate T cell proliferation/activation and an antitumor response to tumor antigens. The growth regulating, cytotoxic, or chemotherapeutic agent may be administered in conventional amounts using known administration regimes. Immunostimulating activity by the compounds of the invention allows reduced amounts of the growth regulating, cytotoxic, or chemotherapeutic agents thereby potentially lowering the toxicity to the patient.

Cancer is characterized by the increase in the number of abnormal., or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites (metastasis). In a cancerous state a cell proliferates under conditions in which normal cells would not grow. Cancer manifests itself in a wide variety of forms, characterized by different degrees of invasiveness and aggressiveness.

Alteration of gene expression is intimately related to the uncontrolled cell growth and de-differentiation which are a common feature of all cancers. The genomes of certain well studied tumors have been found to show decreased expression of recessive genes, usually referred to as tumor suppression genes, which would normally function to prevent malignant cell growth, and/or overexpression of certain dominant genes, such as oncogenes, that act to promote malignant growth. Each of these genetic changes appears to be responsible for importing some of the traits that, in aggregate, represent the full neoplastic phenotype (Hunter, *Cell* 64, 1129 [1991]; Bishop, *Cell* 64, 235-248 [1991]).

A well known mechanism of gene (e.g. oncogene) overexpression in cancer cells is gene amplification. This is a process where in the chromosome of the ancestral cell multiple copies of a particular gene are produced. The process involves unscheduled replication of the region of chromosome comprising the gene, followed by recombination of the replicated segments back into the chromosome (Alitalo et al., *Adv. Cancer Res.* 47, 235-281 [1986]). It is believed that the overexpression of the gene parallels gene amplification, i.e. is proportionate to the number of copies made.

Proto-oncogenes that encode growth factors and growth factor receptors have been identified to play important roles in the pathogenesis of various human malignancies, including breast cancer. For example, it has been found that the human ErbB2 gene (erbB2, also known as her2, or c-erbB-2), which encodes a 185-kd transmembrane glycoprotein receptor ($p185^{HER2}$; HER2) related to the epidermal growth factor receptor (EGFR), is overexpressed in about 25% to 30% of human breast cancer (Slamon et al., *Science* 235: 177-182 [1987]; Slamon et al., *Science* 244:707-712 [1989]).

It has been reported that gene amplification of a protooncogen is an event typically involved in the more malignant forms of cancer, and could act as a predictor of clinical outcome (Schwab et al., *Genes Chromosomes Cancer* 1, 181-193 [1990]; Alitalo et al., supra). Thus, erbB2 overexpression is commonly regarded as a predictor of a poor prognosis, especially in patients with primary disease that involves axillary lymph nodes (Slamon et al., [1987] and [1989], supra; Ravdin and Chamness, *Gene* 159:19-27 [1995]; and Hynes and Stern, *Biochim Biophys Acta* 1198: 165-184 [1994]), and has been linked to sensitivity and/or resistance to hormone therapy and chemotherapeutic regimens, including CMF (cyclophosphamide, methotrexate, and fluoruracil) and anthracyclines (Baselga et al., *Oncology* 11(3 Suppl 1):43-48 [1997]). However, despite the association of erbB2 overexpression with poor prognosis, the odds of HER2-positive patients responding clinically to treatment with taxanes were greater than three times those of HER2-negative patients (Ibid). A recombinant humanized anti-ErbB2 (anti-HER2) monoclonal antibody (a humanized version of the murine anti-ErbB2 antibody 4D5, referred to as rhuMAb HER2 or Herceptin7) has been clinically active in patients with ErbB2-overexpressing metastatic breast cancers that had received extensive prior anticancer therapy. (Baselga et al., *J. Clin. Oncol.* 14:737-744 [1996]).

7. Screening Assays for Drug Candidates

Screening assays for drug candidates are designed to identify compounds that bind or complex with the polypeptides encoded by the genes identified herein or a biologically active fragment thereof, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art.

All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g. on a microtiter plate, by covalent or non-covalent attachments. Non-covalent attachment generally is accomplished by coating the solid surface with a solution of the polypeptide and drying. Alternatively, an immobilized antibody, e.g. a monoclonal antibody, specific for the polypeptide to be immobilized can be used to anchor it to a solid surface. The assay is performed by adding the non-immobilized component, which may be labeled by a detectable label, to the immobilized component, e.g. the coated surface containing the anchored component. When the reaction is complete, the non-reacted components are removed, e.g. by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular protein encoded by a gene identified herein, its interaction with that protein can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature* (London) 340, 245-246 (1989); Chien et al., *Proc. Natl. Acad. Sci. USA* 88, 9578-9582 (1991)] as disclosed by Chevray and Nathans [*Proc. Natl. Acad. Sci. USA* 89, 5789-5793 (1991)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for γ-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In order to find compounds that interfere with the interaction of a gene identified herein and other intra- or extracellular components can be tested, a reaction mixture is usually prepared containing the product of the gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described above. The formation of a complex in the control reaction(s) but not in the reaction mixture containing the test compound indicates that the test compound interferes with the interaction of the test compound and its reaction partner.

8. Compositions and Methods for the Treatment of Immune Related Diseases

The compositions useful in the treatment of immune related diseases include, without limitation, antibodies, small organic and inorganic molecules, peptides, phosphopeptides, antisense and ribozyme molecules, triple helix molecules, etc. that inhibit or stimulate immune function, for example, T cell proliferation/activation, lymphokine release, or immune cell infiltration.

For example, antisense RNA and RNA molecule act to directly block the translation of mRNA by hybridizing to targeted mRNA and preventing protein translation. When antisense DNA is used, oligodeoxyribonucleotides derived from the translation initiation site, e.g. between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g. Rossi, *Current Biology* 4, 469-471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g. PCT publication No. WO 97/3355 1, supra.

These molecules can be identified by any or any combination of the screening assays discussed above and/or by any other screening techniques well known for those skilled in the art.

9. Antibodies

Among the most promising drug candidates according to the present invention are antibodies and antibody fragments which may inhibit (antagonists) or stimulate (agonists) T cell proliferation, leucocyte infiltration, etc. Exemplary antibodies include polyclonal, monoclonal, humanized, bispecific and heteroconjugate antibodies.

a. Polyclonal Antibodies

Methods of preparing polyclonal antibodies are known to skilled artisan. Polyclonal antibodies can be raised in a mammal, for example, by one or more injections of an immunizing agent, and, if desired, an adjuvant. Typically, the immunizing agent and/or adjuvant will be injected in the mammal by multiple subcutaneous or intraperitoneal injections. The immunizing agent may include the PRO301, PRO362 or PRO245 polypeptide of the invention or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

b. Monoclonal Antibodies

Antibodies which recognize and bind to the polypeptides of the invention or which act as antagonists thereto may, alternatively be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal., is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO301, PRO362 or PRO245 polypeptide of the invention, an antigenic fragment or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, California and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against the polypeptide of the invention or having similar activity as the polypeptide of the invention. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxyapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies are preferably monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

c. Human and Humanized Antibodies

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general., the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and coworkers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985); Boerner et al., *J. Immunol.*, 147(1):86-95 (1991); U.S. Pat. No. 5,750,373]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

d. Bispecific Antibodies

Bispecific antibodies are monoclonal, preferably human or humanized, antibodies that have binding specificities for at least two different antigens. In the present case, one of the binding specificities may be for the polypeptide of the invention, the other one is for any other antigen, and preferably for a cell-surface protein or receptor or receptor subunit.

Methods for making bispecific antibodies are known in the art. Traditionally, the recombinant production of bispecific antibodies is based on the coexpression of two immunoglobulin heavy-chain/light-chain pairs, where the two heavy chains have different specificities (Milstein and Cuello, *Nature*, 305:537-539 [1983]). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are cotransfected into a suitable host organism. For further details of generating bispecific antibodies see, for example, Suresh et al., *Methods in Enzymology*, 121:210 (1986).

e. Heteroconjugate Antibodies

Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl4-mercaptobutyrimidate and those disclosed, for example, in U.S. Pat. No. 4,676,980.

f Effector Function Engineering

It may be desirable to modify the antibody of the invention with respect to effector function, so as to enhance the effectiveness of the antibody in treating an immune related disease, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B., *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design*, 3:219-230 (1989).

g. Immunoconjugates

The invention also pertains to immunoconjugates comprising an antibody conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins,

*Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tisue pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

h. Immunoliposomes

The proteins, antibodies, etc. disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent (such as doxorubicin) may be optionally contained within the liposome. See Gabizon et al., *J. National Cancer Inst*. 81(19)1484 (1989).

10. Pharmaceutical Compositions

The active molecules of the invention, polypeptides and antibodies, as well as other molecules identified by the screening assays disclosed above, can be administered for the treatment of inflammatory diseases, in the form of pharmaceutical compositions.

Therapeutic formulations of the active molecule, preferably a PRO301, PRO362 or PRO245 polypeptide or antibody of the invention, are prepared for storage by mixing the active molecule having the desired degree of purity with optional pharmaceutically acceptable carriers, excipients or stabilizers (*Remington's Pharmaceutical Sciences* 16th edition, Osol, A. Ed. [1980])), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Compounds identified by the screening assays of the present invention can be formulated in an analogous manner, using standard techniques well known in the art.

Lipofections or liposomes can also be used to deliver the polypeptide, antibody, or an antibody fragment, into cells. Where antibody fragments are used, the smallest inhibitory fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad. Sci. USA* 90, 7889-7893 [1993]).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active molecules may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37C, resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

11. Methods of Treatment

It is contemplated that the polypeptides, antibodies and other active compounds of the present invention may be used to treat various inflammatory diseases and conditions, such as T cell mediated diseases, including those characterized by infiltration of leucocyte cells into a tissue, stimulation of T-cell proliferation, inhibition of T-cell proliferation, increased or decreased vascular permeability or the inhibition thereof.

The compounds of the invention (e.g., PRO301, PRO362, PRO245) encode new members of a family of proteins characterized by homology to A33 antigen. The proinflammatory nature of the compounds of the invention is indicated in the in vitro assays below.

The proteins encoded by the DNA40628, DNA45416 and DNA35638 compounds of the invention [(SEQ ID NO: 1, SEQ ID NO: 2 and SEQ ID NO: 9), respectively], share homology with identity with junctional adhesion molecule (JAM), Martin-Padura et al., *J. Cell Biol.* 1998 142(1): 117-27. The most substantial identity is shared by the PRO301 protein encoded by DNA40628 (SEQ ID NO: 1) at 67%. JAM is involved in the recruitment of monocytes in response to MCP-1, MCP-3 and LPS in vivo. Antibodies to JAM block monocyte transmigration in vivo. JAM is localized to the murine epithelia and endothelia as a junctional adhesion molecule for monocyte transmigration. Other leukocytes may also use JAM, but no information supports this notion. JAM is elevated in the colon of mice with colitis and likely plays a role in the recruitment of monocytes or leukocytes into the colonic lesion.

Exemplary conditions or disorders to be treated with the polypeptides, antibodies and other compounds of the invention, include, but are not limited to inflammatory bowel disease (i.e, ulcerative colitis, Crohn's disease), systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as cystic fibrosis, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

In systemic lupus erythematosus, the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, intestitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rhematoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of anti-nuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet β cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barr syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+T lymphocytes are the predominant cell type at lesions. The mechanism of oligodendrocyte cell death and subsequent demyelination is not known but is likely T lymphocyte driven.

Inflammatory and Fibrotic Lung Disease, including eosinophilic pneumonias, idiopathic pulmonary fibrosis and hypersensitivity pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

Other diseases in which intervention of the immune and/or inflammatory response have benefit are Infectious disease including but not limited to viral infection (including but not limited to AIDS, hepatitis A, B, C, D, E) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e. as from chemotherapy) immunodeficiency), and neoplasia.

It has been demonstrated that some human cancer patients develop an antibody and/or T lymphocyte response to antigens on neoplastic cells. It has also been shown in animal models of neoplasia that enhancement of the immune response can result in rejection or regression of that particular neoplasm. Molecules that enhance the T lymphocyte response in the MLR have utility in vivo in enhancing the immune response against neoplasia. Molecules which enhance the T lymphocyte proliferative response in the MLR (or small molecule agonists or antibodies that affected the same receptor in an agonistic fashion) can be used therapeutically to treat cancer. Molecules that inhibit the lymphocyte response in the MLR also function in vivo during neoplasia to suppress the immune response to a neoplasm; such molecules can either be expressed by the neoplastic cells themselves or their expression can be induced by the neoplasm in other cells. Antagonism of such inhibitory molecules (either with antibody, small molecule antagonists or other means) enhances immune-mediated tumor rejection.

Additionally, inhibition of molecules with proinflammatory properties may have therapeutic benefit in reperfusion injury; stroke; myocardial infarction; atherosclerosis; acute lung injury; hemorrhagic shock; burn; sepsis/septic shock; acute tubular necrosis; endometriosis; degenerative joint disease and pancreatis.

The PRO301, 362 and PRO245 compounds of the present invention, e.g. polypeptides or antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation (intranasal, intrapulmonary) routes. Intravenous or inhaled administration of polypeptides and antibodies is preferred.

In immunoadjuvant therapy, other therapeutic regimens, such administration of an anti-cancer agent, may be combined with the administration of the proteins, antibodies or compounds of the instant invention. For example, the patient to be treated with the immunoadjuvants of the invention may also receive an anti-cancer agent (chemotherapeutic agent) or radiation therapy. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the immunoadjuvant or may be given simultaneously therewith. Additionally, an anti-oestrogen compound such as tamoxifen or an anti-progesterone such as onapristone (see, EP 616812) may be given in dosages known for such molecules.

It may be desirable to also administer antibodies against other immune disease associated or tumor associated antigens, such as antibodies which bind to CD20, CD11a, CD 18, ErbB2, EGFR, ErbB3, ErbB4, or vascular endothelial factor (VEGF). Alternatively, or in addition, two or more antibodies binding the same or two or more different antigens disclosed herein may be coadministered to the patient. Sometimes, it may be beneficial to also administer one or more cytokines to the patient. In one embodiment, the polypeptides of the invention are coadministered with a growth inhibitory agent. For example, the growth inhibitory agent may be administered first, followed by a polypeptide of the invention. However, simultaneous administration or administration first is also contemplated. Suitable dosages for the growth inhibitory agent are those presently used and may be lowered due to the combined action (synergy) of the growth inhibitory agent and the polypeptide of the invention.

For the treatment or reduction in the severity of immune related disease, the appropriate dosage of an a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments. Preferably, it is desireable to determine the dose-response curve and the pharmaceutical composition of the invention first in vitro, and then in useful animal models prior to testing in humans.

For example, depending on the type and severity of the disease, about 1 μg/kg to 15 mg/kg (e.g. 0.1-20 mg/kg) of polypeptide or antibody is an initial candidate dosage for administration to the patient, whether, for example, by one or more separate administrations, or by continuous infusion. A typical daily dosage might range from about 1 ug/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

12. Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually a polypeptide or an antibody of the invention. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

13. Diagnosis and Prognosis of Immune Related Disease

Cell surface proteins, such as proteins which are overexpressed in certain immune related diseases, are excellent targets for drug candidates or disease treatment. The same proteins along with secreted proteins encoded by the genes amplified in immune related disease states find additional use in the diagnosis and prognosis of these diseases. For example, antibodies directed against the protein products of genes amplified in multiple sclerosis, rheumatoid arthritis, or another immune related disease, can be used as diagnostics or prognostics.

For example, antibodies, including antibody fragments, can be used to qualitatively or quantitatively detect the expression of proteins encoded by amplified or overexpressed genes ("marker gene products"). The antibody preferably is equipped with a detectable, e.g. fluorescent label, and binding can be monitored by light microscopy, flow cytometry, fluorimetry, or other techniques known in the art. These techniques are particularly suitable, if the overexpressed gene encodes a cell surface protein Such binding assays are performed essentially as decribed above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that-a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

Example 1

Isolation of cDNA clones Encoding Human PRO301

The extracellular domain (ECD) sequences (including the secretion signal sequence, if any) from about 950 known secreted proteins from the Swiss-Prot public database were used to search EST databases. The EST databases included public EST databases (e.g., GenBank), a proprietary EST database (LIFESEQ®, Incyte Pharmaceuticals, Palo Alto, Calif. ). The search was performed using the computer program BLAST or BLAST2 [Altschul et al., *Methods in Enzymology*, 266:460-480 (1996)] as a comparison of the ECD protein sequences to a 6 frame translation of the EST sequences. Those comparisons resulting in a BLAST score of 70 (or in some cases, 90) or greater that did not clustered and assembled into consensus DNA sequences with the program "phrap" (Phil Green, University Washington, Seattle, Wash.

A consensus DNA sequence encoding DNA35936 was assembled using phrap. In some cases, the consensus DNA sequence was extended using repeated cycles of blast and phrap to extend the consensus sequence as far as possible using the three sources of EST sequences listed above.

Based on this consensus sequence, oligonucleotides were synthesized: 1) to identify by PCR a cDNA library that contained the sequence of interest, and 2) for use as probes to isolate a clone of the full-length coding sequence. Forward and reverse PCR primers (notated as *.f and *.r, respectively) may range from 20 to 30 nucleotides (typically about 24), and are designed to give a PCR product of 100-1000 bp in length. The probe sequences (notated as *.p) are typically 40-55 bp (typically about 50) in length. In some cases, additional oligonucleotides are synthesized when the consensus sequence is greater than 1-1.5 kbp. In order to screen several libraries for a source of a full-length clone, DNA from the libraries was screened by PCR amplification, as per Ausubel et al., *Current Protocols in Molecular Biology*, with the PCR primer pair. A positive library was then used to isolate clones encoding the gene of interest by the in vivo cloning procedure suing the probe oligonucleotide and one of the PCR primers.

In order to screen several libraries for a source of a full-length clone, DNA from the libraries was screened by PCR amplification with the PCR primer pair identified above. A positive library was then used to isolate clones encoding the PRO301 gene using the probe oligonucleotide and one of the PCR primers.

RNA for construction of the cDNA libraries was isolated from human fetal kidney. The cDNA libraries used to isolated the cDNA clones were constructed by standard methods using commercially available reagents (e.g., Invitrogen, San Diego, Calif.; Clontech, etc.) The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

A cDNA clone was sequenced in its entirety. The full length nucleotide sequence of native sequence DNA40628 is shown in FIG. 5 (SEQ ID NO: 11). Clone DNA40628 contains a single open reading frame with an apparent translational initiation site at nucleotide positions 52-54 (FIG. 5; SEQ ID NO: 11). The predicted polypeptide precursor is 299 amino acids long with a predicted molecular weight of 32583 daltons and pI of 8.29. Clone DNA40628 has been deposited with ATCC and is assigned ATCC deposit No. 209432.

Based on a BLAST and FastA sequence alignment analysis of the full-length sequence, PRO301 encoded by DNA40628 shows amino acid sequence identity to A33 antigen precursor (30%) and coxsackie and adenovirus receptor protein (29%).

The oligonucleotide sequences used in the above procedure were the following:

```
OLI2162 (35936.f1)(SEQ ID NO: 12)
TCGCGGAGCTGTGTTCTGTTTCCC

OLI2163 (35936.p1)(SEQ ID NO: 13)
TGATCGCGATGGGGACAAAGGCGCAAGCTCGAGAGGAAACTGTTGTGCCT
```

```
-continued
OLI2164 (35936.f2)(SEQ ID NO: 14)
ACACCTGGTTCAAAGATGGG

OLI2165 (35936.r1)(SEQ ID NO: 15)
TAGGAAGAGTTGCTGAAGGCACGG

OLI2166 (35936.f3)(SEQ ID NO: 16)
TTGCCTTACTCAGGTGCTAC

OLI2167 (35936.r2)(SEQ ID NO: 17)
ACTCAGCAGTGGTAGGAAAG
```

Example 2

Isolation of cDNA Clones Encoding Human PRO362

The extracellular domain (ECD) sequences (including the secretion signal, if any) of about 950 known secreted proteins from the Swiss-Prot public protein database were used to search expressed sequences tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST-2 (e.g., Altshul et al., *Methods in Enzymology* 266: 460-480 (1996)) as a comparison of the ECD protein sequences to a 6 frame translation of the EST sequence. Those comparisons resulting in a BLAST score 70 (or in some cases 90) or greater that did not encode known proteins were clustered and assembled into consensus DNA sequences with the program "phrap" (Phil Green, University of Washington, Seattle, Wash.

A consensus DNA sequence was assembled relative to other EST sequences using phrap. This consensus sequence is herein designated DNA42257 (SEQ ID NO: 5) (see FIG. 4C). Based on the DNA42257 (SEQ ID NO: 5) consensus sequence shown in FIG. 4C, oligonucleotides were sythesized: 1) to identify by PCR a cDNA library that contained the sequence of interest, and 2) for use as probes to isolate a clone of the full-length coding sequence for PRO362. Forward and reverse PCR primers generally range from 20 to 30 mucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

PCR primers (forward and reverse) were synthesized:

```
forward PCR primer 1 (42257.f1) 5'-TATCCCTCCAATTGAGCACCCTGG-3'   (SEQ ID NO: 18)

forward PCR primer 2 (42257.f2) 5'-GTCGGAAGACATCCCAACAAG-3'      (SEQ ID NO: 19)

reverse PCR primer 1 (42257.r1) 5'-CTTCACAATGTCGCTGTGCTGCTC-3'   (SEQ ID NO: 20)

reverse PCR primer 2 (42257.r2  5'-AGCCAAATCCAGCAGCTGGCTTAC-3'   (SEQ ID NO: 21)
```

Additionally, a synthetic oligonucleotide hybridization probe was constructed from the consenus DNA42257 sequence which had the following nucleotide sequence:

Hybridization probe (42257.p1)
5'-TGGATGACCGGAGCCACTACACGTGT-GAAGTCACCTGGCAGACTCCTGAT-3' (SEQ ID NO: 22).

In order to screen several libraries for a source of a full-length clone, DNA from the libraries was screened by PCR amplification with the PCR primer pairs identified above. A positive library was then used to isolate clones encoding the PRO362 gene using the probe oligonucleotide and one of the PCR primers.

RNA for construction of the cDNA libraries was isolated from human fetal brain tissue (LIB 153). The cDNA libraries used to isolate the cDNA clones were constructed by standard methods using commercially available reagents such as those from Invitrogen, San Diego, Calif. The cDNA was primed with oligo dT containing a NotI site linked with blunt to SalI hemikinased adaptors, cleaved with NotI, sized appropriately be gel electrophoresis, and cloned in a defined orientation into a suitable cloning vector (such as pRKB or pRKD; pRKSB is a precursor of pRK5D that does not contain the SfiI site; see Holmes et al., *Science* 253: 1278-1280 (1991)) in the unique XhoI and NotI sites.

DNA sequencing of the clones isolated as described gave the full-length DNA sequence for an isolated PRO362 [herein designated as UNQ317 (DNA45416-1251)(SEQ ID NO: 7).

The entire nucleotide sequence of UNQ317 (DNA45416-1251) is shown in FIG. 6 (SEQ ID NO: 7). Clone UNQ367 (DNA45416-1251) (SEQ ID NO: 7) contains a single open reading frame with an apparent translational initiation site at nucleotide positions 1082-1084 (FIG. 6, SEQ ID NO: 7). The predicted polypeptide precursor is 321 amino acids long (FIG. 3, SEQ ID NO: 2). The full-length PRO362 protein shown if FIG. 3 has an estimated molecular weight of about 35,544 daltons and a pI of about 8.51. Analysis of the full-length PRO362 polypeptide as shown in FIG. 3 (SEQ ID NO: 2) evidences the presence of a glycosaminoglycan attachment site at about amino acid 149 to about amino acid 152 and a transmembrane domain from about amino acid 276 to about amino acid 306. Clone UTNQ317 (DNA45416-1251) has been deposited with ATCC desposit No.: 209620.

Example 3

Isolation of cDNA Clones Encoding Human PRO245

The extracellular domain (ECD) sequences (including the secretion signal., if any) of about 950 known secreted proteins from the Swiss-Prot public protein database were used to search expressed sequences tag (EST) databases. The EST databases included public EST databases (e.g., GenBank) and a proprietary EST DNA database (LIFESEQ®, Incyte Pharmaceuticals, Palo Alto, Calif.). The search was performed using the computer program BLAST or BLAST-2 (e.g., Altshul et al., *Methods in Enzynology* 266: 460-480 (1996)) as a comparison of the ECD protein sequences to a 6 frame translation of the EST sequence. Those comparisons resulting in a BLAST score 70 (or in some cases 90) or greater that did not encode known proteins were clustered and assembled into consensus DNA sequences with the program "phrap" (Phil Green, University of Washington, Seattle, Wash.

A consensus DNA sequence was assembled relative to other EST sequences, wherein the consensus sequence is herein designated DNA30954 (SEQ ID NO: 27). Based on the DNA30954 consensus sequence, oligonucleotides were synthesized to identify by PCR a cDNA library that contained the sequence of interest and for use as probes to isolate a clone of the full-length coding sequence for PRO245.

A pair of PCR primers (forward and reverse) were synthesized:

```
forward PCR 5'-ATCGTTGTGAAGTTAGTGCCCC-3'   (SEQ ID
primer                                      NO: 28)

reverse PCR 5'-ACCTGCGATATCCAACAGAATTG-3'  (SEQ ID
primer                                      NO: 29)
```

Forward and reverse PCR primers generally range from 20 to 30 mucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair.

Additionally, a synthetic oligonucleotide hybridization probes was constructed from the consensus DNA30954 sequences which had the following nucleotide sequence:

hybridization probe:
5'-GGAAGAGGATACAGTCACTCTGGAAG-TATTAGTGGCTCCAGCAGTTCC-3' (SEQ ID NO: 30)

In order to screen several libraries for a source of a full-length clone, DNA form the libraries was screened by PCR amplification with the PCR primer pair identified above. A positive library was then used to isolated clones encoding the PRO245 gene using the probe oligonucleotide and one of the PCR primers.

RNA for construction of the cDNA libraries was isolated from human fetal liver tissue. The cDNA libraries used to isolate the cDNA clones were constructed by standrd methods using commercially available reagents such as those from Invitrogen, San Diego, CA. The cDNA was primed with oligo cT containing a notI site, linked with blunt to SalI hemokinased adaptors, cleaved with NotI, sized appropriately by gel electrophoresis, and cloned in a defined orientation into a suitable cloning vector (such as pRKB or pRKD; pRKSB is a precursor of pRKSD that does not contain the SfiI site; see Holmes et al., *Science* 253: 1278-1280 (1991)) in the unique XhoI and NotI sites.

DNA sequencing of the clones isolated as described above gave the full-length DNA sequence for a native sequence PRO245 [herein designated as UNQ219 (DNA35638)(SEQ ID NO: 8)] and the derived protein sequence (SEQ ID NO: 9).

The entire nucleotide sequence of UNQ219 (DNA35638) is shown in FIG. 7 (SEQ ID NO: 8). Clone UNQ219 (DNA35638)(SEQ ID NO: 8) contains a single open reading frame with an apparent translational initiation site at nucleotide positions 89-91 [Kozak et al., supra] and ending at the stop codon at nucleotide positions 1025-1027 (FIG. 7, SEQ ID NO: 8). The predicted polypeptide precursor is 312 amino acids long (FIG. 11)(SEQ ID NO: 9). Clone UNQ219 (DNA35638) has been deposited with the ATCC on Sep. 17, 1997 and is assigned ATCC deposit No. 209265.

Example 4

Inhibition of VEGF Stimulated Proliferation of Endothelial Cell Growth

Bovine adrenal cortical capillary endothelial (ACE) cells (from primary culture, maximum 12-14 passages) were plated on 96-well microtiter plates (Amersham Life Science) at a density of 500 cells/well per 100 µL in low glucose DMEM, 10% calf serum, 2 mM glutamine, 1× pen/strept and fungizone, supplemented with 3 ng/mL VEGF. Controls were plated the same way but some did not include VEGF. A test sample of the PRO301 and PRO245 polypeptide was added in a 100 µl volume for a 200 mcL final volume. Cells were incubated for 6-7 days at 37° C. The media was aspirated and the cells washed 1× with PBS. An acid phosphatase reaction mixture (100 µL, 0.1M sodium acetate, pH 5.5, 0.1% Triton-100, 10 mM p-nitrophenyl phosphate) was added. After incubation for 2 hours at 37° C., the reaction was stopped by addition of 10 mcL 1N NaOH. OD was measured on microtiter plate reader at 405 nm. Controls were no cells, cells alone, cells+FGF (5 ng/mL), cells+VEGF (3 ng/mL), cells+VEGF (3 ng/ml)+TGF-β (1 ng/ml), and cells+VEGF (3ng/mL)+LIF (5 ng/mL). (TGF-β at a 1 ng/ml concentration is known to block 70-90% of VEGF stimulated cell proliferation.)

The results were assessed by calculating the percentage inhibition of VEGF (3 ng/ml) stimulated cells proliferation, determined by measuring acid phosphatase activity at $OD_{405}$ nm, (1) relative to cells without stimulation, and (2) relative to the reference TGF-β inhibition of VEGF stimulated activity. The results, shown in Table 1, are indicative of the utility of the PRO301 and PRO245 polypeptide in the inhibition of cell growth, especially cancer therapy and specifically in inhibiting tumor angiogenesis.

TABLE 1

| Compound Tested | Concentration | % Proliferation relative to control |
|---|---|---|
| DNA40628 protein (SEQ ID NO: 1) | 7.0 nM | 1.02 |
| DNA40628 protein (SEQ ID NO: 1) | 70.0 nM | 0.88 |
| DNA40628 protein (SEQ ID NO: 1) | 700.0 nM | 0.44 |
| DNA40628 protein (SEQ ID NO: 1) | 0.01% | 0.92 |
| DNA40628 protein (SEQ ID NO: 1) | 0.1% | 0.85 |
| DNA40628 protein (SEQ ID NO: 1) | 1.0% | 0.68 |
| DNA35638 protein (SEQ ID NO: 9) | 0.01% | 0.76 |
| DNA35638 protein (SEQ ID NO: 9) | 0.1% | 0.35 |
| DNA35638 protein (SEQ ID NO: 9) | 1.0% | 0.11 |
| DNA35638 protein (SEQ ID NO: 9) | 0.48 nM | 1.03 |
| DNA35638 protein (SEQ ID NO: 9) | 4.8 nM | 0.95 |
| DNA35638 protein (SEQ ID NO: 9) | 48.0 nM | 0.49 |

Example 5

Stimulatory Activity in Mixed Lymphocyte Reaction (MLR) Assay

This example shows that the polypeptides of the invention are active as a stimulator of the proliferation of stimulated T-lymphocytes. Compounds which stimulate proliferation of lymphocytres are useful therapeutically where enhancement of an inflammatory response is beneficial. Compounds which inhibit proliferation of lymphocytes are useful therapeutically where suppression of inflammatory response. A therapeutic agent may take the form of antagonists of the polypeptide of the invention, for example, murine-human chimeric, humanized or human antibodies against the polypeptide.

The basic protocol for this assay is described in *Current Protocol in Immunology*, Unit 3.12, J. E. Coligan, A. M. Kruisbeek, D H Marglies, E M Shevach and W Strober, Eds, National Institute of Health, Published by John Wiley & Sons, Inc.

More specifically, in one assay variant, peripheral blood mononuclear cells (PBMC) are isolated from mammalian individuals, for example a human volunteer, by leukopheresis (one done will supply stimulatory PBMCs, the other donor will supply responder PBMCs). If desired, the cells are frozen in fetal bovine serum and DMSO after isolation. Frozen cells may be thawed overnight in assay media (37° C., 5% $CO_2$) and then washed and resuspended to $3\times10^6$ cells/ml of assay media (RPMI; 10% fetal bovine serum, 1% penicillin/streptomycin, 1% glutamine, 1% HEPES, 1% non-essential amino acids, 1% pyruvate).

The stimulator of PBMCs are prepared by irradiating the cells (about 3000 Rads). The assay is prepared by plating in triplicate wells a mixture of: 100 μl of test sample diluted to 1% of 0.1%; 50 μl of irradiated stimulator cells and 50 μl of responder PBMC cells. 100 μL of cell culture media or 100 ml of CD4-IgG is used as the control. The wells are then incubated at 37° C., 5% $CO_2$ for 4 days. On day 5, each well is pulsed with tritiated thymidine (1.0 mC/well; Amersham). After hours the cells are washed 3 times and then the uptake of the label is evaluated.

In another variant of this assay, PBMC's are isolated from the spleens of Balb/c mice and C57B6 mice. The cells are teased from freshly harvested spleens in assay media (RPMI; 10% fetal bovine serum, 1% penicillin/streptomycin, 1% glutamine, 1% HEPES, 1% non-essential amino acids, 1% pyruvate) and the PBMCs are isolated by overlaying these cells over Lympholyte M (Organon Teknika), centrifuging at 2000 rpm for 20 minutes, collecting ans washing the mononuclear cell layer in assay media and resuspending the cells to $1\times10^7$ cells/ml of asssay media. The assay is then conducted as described above. The results of this assay for compounds of the invention are shown below in Table 2. Positive increases over control are considered positive with increases of greater than or equal to 180% being preferred. However, any value greater than control indicates a stimulatory effect for the test protein.

TABLE 2

| Compound | Concentration | Percent Increase over Control |
|---|---|---|
| DNA40628 protein (SEQ ID NO: 1) | 0.1% | 181.7 |
| DNA40628 protein (SEQ ID NO: 1) | 1.0% | 187.3 |
| DNA40628 protein (SEQ ID NO: 1) | 0.1% | 193.4 |
| DNA40628 protein (SEQ ID NO: 1) | 1.0% | 204.1 |
| DNA45416 protein (SEQ ID NO: 2) | 0.1% | 87.4 |
| DNA45416 protein (SEQ ID NO: 2) | 1.0% | 180.2 |
| DNA35638 protein (SEQ ID NO: 9) | 0.1% | 189.7 |
| DNA35638 protein (SEQ ID NO: 9) | 0.1% | 193.7 |
| DNA35638 protein (SEQ ID NO: 9) | 1.0% | 212.5 |
| DNA35638 protein (SEQ ID NO: 9) | 1.0% | 300.5 |

Example 6

Inflammatory Cell Infiltrates into Guinea Pig Skin

The following example shows that the polypeptides of the invention are proinflammatory in that they stimulate inflammatory cell infiltrates (i.e., neutrophilic, eosinophilic, monocytic or lymphocytic) into guinea pig skin. The assay described herein monitors the capacity of each protein to induce an inflammatory cell infiltrate into the skin of a guinea pig. Compounds which stimulate inflammatory infiltration are useful therapeutically were enhancement of an inflammatory response is beneficial. Compounds which inhibit proliferation of lymphocytes are useful therapeutically where suppression of an inflammatory response is beneficial. A therapeutic agent may take the form of antagonists of the polypeptides of the invention, for example, murine-human chimeric, humanized or human antibodies against the polypeptide.

Hairless guinea pigs (Charles River Labs) weighing 350 grams or more are anesthetized with ketamine (75-80 mg/kg body weight) and Xylazine (5 mg/kg body weight) intramuscularly. The protein samples are injected intradermally onto the backs of each animal at a volume of 100 μl per injection site. There are approximately 16-24 injection sites per animal. One mL of Evans blue dye (1% in physiological buffered saline) is injected intracardially. The animals are euthanized after 6 hours. Each skin injection site is biopsied and fixed in formalin. The skins are prepared for histopathological evaluation. Each site is evaluated for inflammatory cell infiltration into the skin. Sites with visible inflammatory cells are scored as positive. Samples inducing an inflammatory cell infiltrate are scored as proinflammatory substances.

TABLE 3

| Compound | Proinflammatory activity |
| --- | --- |
| DNA40628 protein (SEQ ID NO: 1) | + |
| DNA45416 protein (SEQ ID NO: 2) | + |
| DNA35638 protein (SEQ ID NO: 9) | + |
| Negative control | − |

Example 7

Interaction with Human Neutrophils

The following example shows the ability of the polypeptides of the invention to bind to human neutrophils, a molecule associated with inflammation and the inflammatory response.

Neutrophils isolated from the blood of human donors (PMN) as described in Scan. J. Clin. Lab Invest. Suppl. 97: 51-76 (1968), were incubated with an Ig-fusion of protein encoded by DNA40628 (prepared as discussed in the following examples) or a negative control humanized antibody.

The PMNs were resuspended in a microfuge tube in PBS at a density of $2 \times 10^6$ cell equivalents per condition. The cells were washed twice with ice cold PBS and pelleted at 400×g between washes. The PMN cells were blocked with 0.5% BSA in PBS (blocking reagent) at 4° C. for 1 hour. After the incubation, the cells were further washed two additional times with blocking reagent. The PMNs were pelleted after the final wash and resuspended in 1 ml of blocking buffer at 0.1 µg/ml in both DNA40628 protein and control antibody. The incubation was carried out for 2 hours at 4° C. The PMN cells were gently resuspended every 15 minutes on ice, then washed and pelleted 5 times in blocking buffer, with each wash lasting 5 minutes at 4° C. and pelleting occurring at 400×g. A 1:1000 dilution of goat and anti-human IgG Fc specific-alkaline phosphatase-conjugated in the blocking buffer was then applied to the PMN cells. The PMN cells were incubated for 1 hour at 4° C., with gently mixing every 15 minutes on ice. The PMN cells were then washed 5 times with blocking buffer, resuspended in the appropriate substrate for alkaline phosphatase and distributed in 4 equi-100 µl aliquots onto a microtiter plate. Color development was read at O.D. 405. The results are shown in FIG. 21.

Example 8

Dot Blot Tissue Hybridization

A human RNA master blot (Clontech) was hybridized overnight at 65° C. in Expresshyb® buffer (Clontech) per the manufacturer's instructions with 100 nM of psoralen-biotin labeled DNA40628 cDNA probe (SEQ ID NO: 7). Streptavidin-alkaline phosphatase was used to detect the biotinylated probe. The blot was developed with CDP-star substrate (Ambion) and exposed for various times on Biomax film (Kodak). A cDNA hybridization analysis of human tissues show that DNA40628 mRNA is expressed in many tissues except the cerebellum and spinal cord FIG. 19. DNA40628 mRNA is highly expressed in the colon, prostate, stomach, ovary, salivary gland, kidney, lung, trachea and placenta.

Example 9

Gene Product Overexpression

This example shows that genes encoding various proteins indicated in FIG. 20 are overexpressed in colitic colon of CRF2-4-/- "knock out" mice. Therapeutic agents may take the form of antagonists of the indicated gene products, for example, murine-human chimeric, humanized or human antibodies thereagainst.

CRF 2-4-/- mice (Spencer et al., J. Exp. Med. 187, 571-578 (1998)), are animals which have a subunit of the gene encoding the IL-10 receptor removed. The mice are unresponsive to the downregulatory functions of IL-10 for macrophage activation, and cannot downregulate response to lipopolysaccharide triggering of macrophage TNF-α secretion. They develop a chronic colitis which can lead to colonic adenocarcinoma.

The probes for the proteins indicated in FIG. 20 were created from mRNA templates for the indicated gene products and used in the 5'-nuclease assay (e.g., TaqMan™) and real-time quantitative PCR (e.g., ABI Prizm 7700 Sequence Detection System™ (Perkin-Elmer, Applied Biosystems Division, Foster City, Calif.). The results are resported in delta CT units. One unit corresponds to 1 PCR cycle or approximately a 2-fold amplification relative to normal, two units correspond to 4-fold, 3 units to 8-fold, etc. Quantitation was obtained using primers and a TaqMan™ fluorescent tagged-mRNA derived from the tested inflammatory-related gene products indicated in FIG. 20. Regions of the indicated gene products which are most likely to contain unique nucleic acid sequences and which are least likely to have spliced out introns are preferred for the primer derivation, e.g. 3'-untranslated region.

The 5'-nuclease assay reaction is a fluorescent PCR-based technique which makes use of the 5'-exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reported fluorescent dye and a quencher fluorescent dye. Any laser-induced emission from the reporter dye is quenched by the quenching dye when the two dyes are located close together as they are on the probe. During the amplification reaction, the probe is cleaved by the Taq DNA polymerase enzyme in a template-dependent manner. The resultant probe fragments disassociate in solution, and the signal from the release reporter dye is free from the quenching effect of the second fluorophore. One molecule of reporter dye is liberated for each new moleucle synthesized, and detection of the unquenched reporter dye provided the basis for quantitative interpretation of the data.

The 5'-nuclease procedure is run on a real-time quantiative PCR device such as the ABI Prism 7700™ Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The 5'-nuclease assay data are initially expressed as Ct, or the threshold cycle. This is defined as the cycle at which the reporter signal accumulates above the background level of fluorescence. The Ct values are used as quantitative measurement of the relative number of starting copies of a particular target sequence in a nucleic acid sample.

The results of the mRNA amplification are shown in FIG. 20. Expression in wild-type animals were compared with CRF2.4 KO animals with beta-actin as the reference standard. Four animals were measured in each group. All four KO animals were diagnosed with colitis and in addition, three of these had colon adenocarcinoma.

FIG. 18 shows that JAM mRNA is increased 3.3-fold in the colon of CRF2-4–/– mice with colitis. These mice are IL-10 receptor knock outs that develop a spontaneous colitis mediated by lymphocytes, monocytes and neutrophils. IL-10 suppresses the inflammatory response by modulating expression of certain inflammatory cytokines.

As a result, it is likely that PRO301, PRO362 and PRO245 would also have elevated expression in inflammatory human disease, such as inflammatory bowel disease and other inflammatory diseases of the gut.

Example 10

Induction of Endothelial Cell Apoptosis

The ability of the polypeptides of the invention to induce apoptosis in endothelial cells was tested in human venous umbilical vein endothelial cells (HUVEC, Cell Systems). The first day, the cells were plated on 96-well microtiter plates (Amersham Life Sciences, cytostar-T scintillating microplate, RPNQ160, sterile, tissue-culture treated, individually wrapped), in 10% serum (CSG-medium, Cell Systems), at a density of $2\times10^4$ cells per well in a total volume of 100 µl. The second day, PRO301 and PRO245 polypeptide encoded by DNA40628 and DNA35638, respectively, was added in triplicate at dilutions of 1%, 0.33% and 0.11%. On the third day, the ability of the PRO301 and PRO245 polypeptides to induce apoptosis was determined using a commerically available kit, Apoptosis Detection Kit (R&D Systems, Minnesota) in which annexin V, a member of the calcium and phospholipid binding proteins, is used to detect apoptosis, following the protocol recommended by the manufacturer. Fluroescein-labeled annexin V and propidium iodide were added to the cells. Analysis was performed with cytometers equipped with a single laser emitting excitation light at 488 nm. In this test, live cells will not stain with either fluorochrome, necrotic cells will stain with both fluorochromes, and cells undergoing apoptosis will stain only with the annexin V-FITC reagent. The annexin V-FITC generated signal was detected in the FITC signal detector. The results are indicated in the Table 4 below.

TABLE 4

| Compound tested | Concentration | % over background fluorescence |
|---|---|---|
| DNA40628 protein (SEQ ID NO: 1) | 0.11% | 115.8 |
| DNA40628 protein (SEQ ID NO: 1) | 0.33% | 199.3 |
| DNA40628 protein (SEQ ID NO: 1) | 1.0% | 335.6 |
| DNA35638 protein (SEQ ID NO: 9) | 0.11% | 77.6 |
| DNA35638 protein (SEQ ID NO: 9) | 0.33% | 143.7 |
| DNA35638 protein (SEQ ID NO: 9) | 1.0% | 146.0 |
| DNA35638 protein (SEQ ID NO: 9) | 6.82 nM | 67.2 |
| DNA35638 protein (SEQ ID NO: 9) | 20.46 nM | 102.6 |
| DNA35638 protein (SEQ ID NO: 9) | 62.0 nM | 118.8 |

The ability of the protein compounds of the invention to induce endothelial cell apoptosis, particularly in combination with the disruption of cell junction formation as indicated in Example 4 is indicative that the compounds play roles in cell adhesion and transmigration. Similar to murine JAM, the compounds are likely cell junction molecules in epithelia and endothelia, which explains their broad tissue distribution. The disruption of the induction of endothelial cell apoptosis supports a role in cell growth and apoptosis.

Example 11

In Vitro Antitumor Assay

The antiproliferative activity of the PRO301 and PRO362 polypeptides of the invention was determined in the investigational., disease-orientated in vitro anti-cancer drug discovery assay of the National Cancer Institute (NCI), using sulforhodamine B (SRB) dye binding assay essentially as described by Skehan et al., *J. Natl. Cancer Inst.* 82: 1107-1112 (1990). The 60 tumor cell lines employed in this study ("the NCI panel") as well as conditions for their maintenance and culture in vitro have been described by Monks et al., *J. Natl. Cancer Inst.* 83: 757-766 (1991). The purpose of this screen is to initially evaluate the cytotoxic and/or cytostatic activity of the test compounds against different types of tumors (Monks et al., supra, *Boyd, Cancer: Princ. Pract. Oncol. Update* 3(10): 1-12 (1989)).

Cell from approximately 60 human tumor cell lines were harvested with trypsin/EDTA (Gibco), washed once, resuspended in IMEM and their viability was determined. The cell suspensions were added by pipet (100 µL volume) into separate 96-well microtiter plates. The cell density for the 60-day incubation was less than for the 20 day incubation to prevent overgrowth. Inoculates were allowed a preincubation period of 24 hours at 37° C. for stabilization. Dilutions at twice the intended test concentration were added at time zero in 100 ml aliquots to the microtiter plates wells (1:2 dilution). Test compounds were evaluated at give half-log dilutions (1000 to 100,000 fold). Incubations took place for two days and six days in a 5% $CO_2$ atmosphere and 100% humidity.

After incubation, the medium was removed and the cells were fixed in 0.1 ml of 10% trichloroacetic acid at 40° C. The plates were rinsed five times with deionized water, dried, stained for 30 minutes with 0.1 ml of 0.4% sulforhodamine B dye (Sigma) dissolved in 1% acetic acid, rinsed four times with 1% acetic acid to remove unbound dye, dried, and the stain was extracted for five minutes with 0.1 ml of 10 mM Tris base [tris(hydroxymethyl)aminomethane], pH 10.5. The absorbance (OD) of sulforhodamine B at 492 nm was measured using a computer-interfaced, 96-well microtiter plate reader.

A test sample is considered positive if it shows at least 50% growth inhibitory effect at one or more concentrations. The results are shown in the following tables, where the abbreviations are as follows:

NSCL=non-small lung carcinoma

CNS=central nervous system

Leuk=leukemia

TABLE 5

| Test compound | Concentration | Length of assay | Tumor cell line Type | Tumor cell line Designation |
|---|---|---|---|---|
| DNA40628 protein (SEQ ID NO: 1) | 0.075 nM | 6 | Colon<br>Melanoma | HCC-2998<br>M14 |
| DNA40638 protein (SEQ ID NO: 1) | 700 nM | 6 | Melanoma | M14 |
| DNA40628 protein (SEQ ID NO: 1) | 152 nM | 6 | Colon<br>Melanoma | SR<br>LOX IMVI |
| DNA40628 protein (SEQ ID NO: 1) | 15.2 nM | 6 | Melanoma | LOX IMVI |
| DNA40628 protein (SEQ ID NO: 1) | 0.85 nM | 6 | NSCL<br>Ovarian<br>Prostate | HOP62<br>OVCAR-3<br>PC3 |
| DNA45416 protein (SEQ ID NO: 2) | 15 nM | 2 | Ovarian | SK-OV-3 |
| DNA45416 protein (SEQ ID NO: 2) | 15 nM | 6 | NSCL<br>Prostate | NCI-H322M<br>PC-3 |
| DNA45416 protein (SEQ ID NO: 2) | 4.7 nM | 6 | Melanoma | LOX IMVI |
| DNA45416 protein (SEQ ID NO: 2) | 47 nM | 6 | NSCL<br>Colon | NCI-H322M<br>Colo 205 |
| DNA45416 protein (SEQ ID NO: 2) | 152 nM | 2 | CNS<br>Breast | SR-295<br>T047D |
| DNA45416 protein (SEQ ID NO: 2) | 152 nM | 6 | Leuk<br><br>NSCL<br>Colon<br>CNS<br>Melanoma | SR, HL-60 (TB), MOLT-4, K-562<br>NCI-H23, EKVX<br>HCC-2998<br>U251<br>UACC-62, UACC-257, LOX LMVI |
| DNA35638 protein (SEQ ID NO: 9) | 0.35 nM | 2 | NSCL<br>Ovarian | HOP92<br>OVCAR-4 |
| DNA35638 protein (SEQ ID NO: 9) | 0.35 nM | 2 | Leuk | SR |
| DNA35638 protein (SEQ ID NO: 9) | 0.35 nM | 6 | Colon | HCC-2998 |
| DNA35638 protein (SEQ ID NO: 9) | 3.5 nM | 6 | Leuk<br>Colon | SR<br>SW-620 |
| DNA35638 protein (SEQ ID NO: 9) | 6.2 nM | 6 | Colon | HCT-116 |
| DNA35638 protein (SEQ ID NO: 9) | 6.2 nM | 6 | Leuk | RPMI-8226 |

Example 12

Use of PRO301, PRO362 or PRO245 as a Hybridization Probe

The following method describes use of a nucleotide sequence encoding a PRO301, PRO362 or PRO245 as a hybridization probe.

DNA comprising the coding sequence of native sequence PRO301, PRO362 or PRO245 (as shown in FIGS. 5-7, SEQ ID NO: 11, 7 and 8), respectively, is employed as a probe to screen for homologous DNAs (such as those encoding naturally-occurring variants of PRO301, PRO362 or PRO245, respectively) in human tissue cDNA libraries or human tissue genomic libraries.

Hybridization and washing of filters containing either library DNAs is performed under the following high stringency conditions. Hybridization of radiolabeled PRO301-, PRO362- or PRO245-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding a full-length native sequence PRO301, PRO362 or PRO245 can then be identified using standard techniques known in the art.

Example 13

Expression of PRO301, PRO362 or PRO245 in *E. coli*

This example illustrates preparation of an unglycosylated form of PRO301, PRO362 or PRO245 by recombinant expression in *E. coli*.

The DNA sequence encoding PRO301, PRO362 or PRO245 is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO301, PRO362 or PRO245 coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO301, PRO362 or PRO245 protein can then be purified using a metal chelating column under conditions that allow tight binding of the protein.

PRO301 was expressed in E. coli in a poly-His tagged form, using the following procedure. The DNA encoding PRO301 was initially amplified using selected PCR primers. The primers contained restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences were then ligated into an expression vector, which was used to transform an E. coli host based on strain 52 (W3110 fuhA(tonA) lon galE rpoHts(htpRts) clpP(lacIq). Transformants were first grown in LB containing 50 mg/ml carbenicillin at 30° C. with shaking until an O.D.600 of 3-5 was reached. Cultures were then diluted 50-100 fold into CRAP media (prepared by mixing 3.57 g $(NH_4)_2SO_4$, 0.71 g sodium citrate. 2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples were removed to verify expression by SDS-PAGE analysis, and the bulk culture is centrifuged to pellet the cells. Cell pellets were frozen until purification and refolding.

E. coli paste from 0.5 to 1 L fermentations (6-10 g pellets) was resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution was stirred overnight at 4° C. This step results in a denatured protein with all cysteine residues blocked by sulfitolization. The solution was centrifuged at 40,000 rpm in a Beckman Ultracentifuge for 30 min. The supernatant was diluted with 3-5 volumes of metal chelate column buffer (6 M guanidine, 20 mM Tris, pH 7.4) and filtered through 0.22 micron filters to clarify. Depending the clarified extract was loaded onto a 5 ml Qiagen Ni-NTA metal chelate column equilibrated in the metal chelate column buffer. The column was washed with additional buffer containing 50 mM imidazole (Calbiochem, Utrol grade), pH 7.4. The protein was eluted with buffer containing 250 mM imidazole. Fractions containing the desired protein were pooled and stored at 4° C. Protein concentration was estimated by its absorbance at 280 nm using the calculated extinction coefficient based on its amino acid sequence.

The protein was refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes were chosen so that the final protein concentration was between 50 to 100 micrograms/ml. The refolding solution was stirred gently at 4° C. for 12-36 hours. The refolding reaction was quenched by the addition of TFA to a final concentration of 0.4% (pH of approximately 3). Before further purification of the protein, the solution was filtered through a 0.22 micron filter and acetonitrile was added to 2-10% final concentration. The refolded protein was chromatographed on a Poros R1/H reversed phase column using a mobile buffer of 0.1% TFA with elution with a gradient of acetonitrile from 10 to 80%. Aliquots of fractions with A280 absorbance were analyzed on SDS polyacrylamide gels and fractions containing homogeneous refolded protein were pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO301 protein, respectively, were pooled and the acetonitrile removed using a gentle stream of nitrogen directed at the solution. Proteins were formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 14

Expression of PRO301, PRO362 or PRO245 in Mammalian Cells

This example illustrates preparation of a glycosylated form of a PRO301, PRO362 or PRO245 by recombinant expression in mammalian cells.

The vector, pRK5 (see EP 307,247, published Mar. 15, 1989), is employed as the expression vector. Optionally, the PRO301, PRO362 or PRO245 DNA is ligated into pRK5 with selected restriction enzymes to allow insertion of the PRO301, PRO362 or PRO245 DNA using ligation methods such as described in Sambrook et al., supra. The resulting vector is called pRK5-PRO301, pRK5-PRO362 or pRK5-PRO245, respectively.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO301, pRK5-PRO362 or pRK5-PRO245 DNA is mixed with about 1 µg DNA encoding the VA RNA gene [Thimmappaya et al., Cell, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO301, PRO362 or PRO245 polypeptide. The cultures containing transfected cells may undergo further incubation (in serum free medium) and the medium is tested in selected bioassays.

In an alternative technique, PRO301, PRO362 or PRO245 DNA may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-PRO301, pRK5-PRO362 or pRK5-PRO245 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO301, PRO362 or PRO245 can then be concentrated and purified by any selected method, such as dialysis and/or column chromatography.

In another embodiment, PRO301, PRO362 or PRO245 can be expressed in CHO cells. The pRK5-PRO301, pRK5-PRO362 or pRK5-PRO245 can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of PRO301, PRO362 or PRO245 polypeptide, the culture medium may be replaced with serum free medium. Preferably, the cultures are incubated for about 6 days, and then the conditioned medium is harvested. The medium containing the expressed PRO301, PRO362 or PRO245 can then be concentrated and purified by any selected method.

Epitope-tagged PRO301, PRO362 or PRO245 may also be expressed in host CHO cells. The PRO301, PRO362 or PRO245 may be subcloned out of the pRK5 vector. The subclone insert can undergo PCR to fuse in frame with a selected epitope tag such as a poly-his tag into a Baculovirus expression vector. The poly-his tagged PRO301, PRO362 or PRO245 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO301, PRO362 or PRO245 can then be concentrated and purified by any selected method, such as by Ni$^{2+}$-chelate affinity chromatography.

PRO301, PRO362 and PRO245 were expressed in CHO cells by both a transient and stable expression procedure.

Stable expression in CHO cells was performed using the following procedure. The proteins were expressed as an IgG construct (immunoadhesin), in which the coding sequences for the soluble forms (e.g. extracellular domains) of the respective proteins were fused to an IgG1 constant region sequence containing the hinge, CH2 and CH2 domains and/or as a poly-His tagged form.

Following PCR amplification, the respective DNAs were subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5☐ and 3☐ of the DNA of interest to allow the convenient shuttling of cDNA☐s. The vector used expression in CHO cells is as described in Lucas et al., *Nucl. Acids Res.* 24: 9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA were introduced into approximately 10 million CHO cells using commercially available transfection reagents Superfect☐ (Quiagen), Dosper☐ or Fugene☐ (Boehringer Mannheim). The cells were grown and described in Lucas et al., supra. Approximately $3 \times 10^{-7}$ cells are frozen in an ampule for further growth and production as described below.

The ampules containing the plasmid DNA were thawed by placement into water bath and mixed by vortexing. The contents were pipetted into a centrifuge tube containing 10 mLs of media and centrifuged at 1000 rpm for 5 minutes. The supernatant was aspirated and the cells were resuspended in 10 mL of selective media (0.2 μm filtered PS20 with 5% 0.2 μm diafiltered fetal bovine serum). The cells were then aliquoted into a 100 mL spinner containing 90 mL of selective media. After 1-2 days, the cells were transferred into a 250 mL spinner filled with 150 mL selective growth medium and incubated at 37° C. After another 2-3 days, a 250 mL 500 mL and 2000 mL spinners were seeded with $3 \times 10^5$ cells/mL. The cell media was exchanged with fresh media by centrifugation and resuspension in production medium. Although any suitable CHO media may be employed, a production medium described in U.S. Pat. No. 5,122,469, issued Jun. 16, 1992 was actually used. 3L production spinner is seeded at $1.2 \times 10^6$ cells/mL. On day 0, the cell number and pH were determined. On day 1, the spinner was sampled and sparging with filtered air was commenced. On day 2, the spinner was sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion). Throughout the production, pH was adjusted as necessary to keep at around 7.2. After 10 days, or until viability dropped below 70%, the cell culture was harvested by centrifugation and filtering through a 0.22 μm filter. The filtrate was either stored at 4° C. or immediately loaded onto columns for purification.

For the poly-His tagged constructs, the proteins were purified using a Ni-NTA column (Qiagen). Before purification, imidazole was added to the conditioned media to a concentration of 5 mM. The conditioned media was pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column was washed with additional equilibration buffer and the protein eluted with equilibration buffer containing 0.25 M imidazole. The highly purified protein was subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc containing) constructs of were purified from the conditioned media as follows. The conditioned medium was pumped onto a 5 ml Protein A column (Pharmacia) which had been equilibrated in 20 mM Na phosphate buffer, pH 6.8. After loading, the column was washed extensively with equilibration buffer before elution with 100 mM citric acid, pH 3.5. The eluted protein was immediately neutralized by collecting 1 ml fractions into tubes containing 275 μL of 1 M Tris buffer, pH 9. The highly purified protein was subsequently desalted into storage buffer as described above for the poly-His tagged proteins. The homogeneity was assessed by SDS polyacrylamide gels and by N-terminal amino acid sequencing by Edman degradation.

PRO301, PRO362 and PRO245 was also produced by transient expression in COS cells.

Example 15

Expression of PRO301, PRO362 or PRO245 in Yeast

The following method describes recombinant expression of PRO301, PRO362 or PRO245 in yeast.

First, yeast expression vectors are constructed for intracellular production or secretion of PRO301, PRO362 or PRO245 from the ADH2/GAPDH promoter. DNA encoding PRO301, PRO362 or PRO245, a selected signal peptide and the promoter is inserted into suitable restriction enzyme sites in the selected plasmid to direct intracellular expression of PRO301, PRO362 or PRO245. For secretion, DNA encoding PRO301, PRO362 or PRO245 can be cloned into the selected plasmid, together with DNA encoding the ADH2/GAPDH promoter, the yeast alpha-factor secretory signal/leader sequence, and linker sequences (if needed) for expression of PRO301, PRO362 or PRO245.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO301, PRO362 or PRO245 can subsequently be isolated and purified by removing the yeast cells from the fermentation medium by centrifugation and then concentrating the medium using selected cartridge filters. The concentrate containing PRO301, PRO362 or PRO245 may further be purified using selected column chromatography resins.

Example 16

Expression of PRO301, PRO362 or PRO245 in Baculovirus-Infected Insect Cells

The following method describes recombinant expression of PRO301, PRO362 or PRO245 in Baculovirus-infected insect cells.

The PRO301, PRO362 or PRO245 is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the PRO301, PRO362 or PRO245 or the desired portion of the PRO301, PRO362 or PRO245 (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged PRO301, PRO362 or PRO245 can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 Fm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes non-specifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged PRO301, PRO362 or PRO245 are pooled and dialyzed against loading buffer.

Alternatively, purification of the IgG tagged (or Fc tagged) PRO301, PRO362 or PRO245 can be performed using known chromatography techniques, including for instance, Protein A or protein G column chromatography.

PRO301, PRO362 and PRO245 were expressed in baculovirus infected Sf9 insect cells. While the expression was actually performed in a 0.5-2 L scale, it can be readily scaled up for larger (e.g. 8 L) preparations. The proteins were expressed as an IgG construct (immunoadhesin), in which the protein extracellular region was fused to an IgG1 constant region sequence containing the hinge, CH2 and CH3 domains and/or in poly-His tagged forms.

Following PCR amplification, the respective coding sequences were subcloned into a baculovirus expression vector (pb.PH.IgG for IgG fusions and pb.PH.His.c for poly-His tagged proteins), and the vector and Baculogold□ baculovirus DNA (Pharmingen) were co-transfected into 105 *Spodoptera frugiperda* ("Sf9") cells (ATCC CRL 1711), using Lipofectin (Gibco BRL). pb.PH.IgG and pb.PH.His are modifications of the commercially available baculovirus expression vector pVL1393 (Pharmingen), with modified polylinker regions to include the His or Fc tag sequences. The cells were grown in Hink's TNM-FH medium supplemented with 10% FBS (Hyclone). Cells were incubated for 5 days at 28° C. The supernatant was harvested and subsequently used for the first viral amplification by infecting Sf9 cells in Hink's TNM-FH medium supplemented with 10% FBS at an approximate multiplicity of infection (MOI) of 10. Cells were incubated for 3 days at 28° C. The supernatant was harvested and the expression of the constructs in the baculovirus expression vector was determined by batch binding of 1 ml of supernatant to 25 mL of Ni-NTA beads (QIAGEN) for histidine tagged proteins or Protein-A Sepharose CL4B beads (Pharmacia) for IgG tagged proteins followed by SDS-PAGE analysis comparing to a known concentration of protein standard by Coomassie blue staining.

The first viral amplification supernatant was used to infect a spinner culture (500 ml) of Sf9 cells grown in ESF-921 medium (Expression Systems LLC) at an approximate MOI of 0.1. Cells were incubated for 3 days at 28° C. The supernatant was harvested and filtered. Batch binding and SDS-PAGE analysis was repeated, as necessary, until expression of the spinner culture was confirmed.

The conditioned medium from the transfected cells (0.5 to 3 L) was harvested by centrifugation to remove the cells and filtered through 0.22 micron filters. For the poly-His tagged constructs, the protein construct were purified using a Ni-NTA column (Qiagen). Before purification, imidazole was added to the conditioned media to a concentration of 5 mM. The conditioned media were pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column was washed with additional equilibration buffer and the protein eluted with equilibration buffer containing 0.25 M imidazole. The highly purified protein was subsequently desalted into a storage buffer containing 10 mM Hepes, 0.14 M NaCl and 4% mannitol, pH 6.8, with a 25 ml G25 Superfine (Pharmacia) column and stored at –80° C.

Immunoadhesin (Fc containing) constructs of proteins were purified from the conditioned media as follows. The conditioned media were pumped onto a 5 ml Protein A column (Pharmacia) which had been equilibrated in 20 mM Na phosphate buffer, pH 6.8. After loading, the column was washed extensively with equilibration buffer before elution with 100 mM citric acid, pH 3.5. The eluted protein was immediately neutralized by collecting 1 ml fractions into tubes containing 275 mL of 1 M Tris buffer, pH 9. The highly purified protein was subsequently desalted into storage buffer as described above for the poly-His tagged proteins. The homogeneity of the proteins was verified by SDS polyacrylamide gel (PEG) electrophoresis and N-terminal amino acid sequencing by Edman degradation.

PRO301, PRO362 and PRO245 were also expressed in baculovirus infected High-5 cells using an analogous procedure. High-5 cells were grown to a confluency of 50% at 27° C., no $CO_2$, no penicillin and no streptomycin. For each 150 mm plate, 30 μg of pIE based vector containing PRO301, PRO362 or PRO245 was mixed with 1 ml Ex-Cell medium (Media: Ex-cell 401, 1/100 L-Glu JRH Biosciences, #14401-78P, note: medium is light sensitive), and in a separate tube, 100 μl of Cell Fectin (GibcoBRL #10362-010) was mixed with 1 ml of Ec-Cell medium. The pIE1-1 and pIE1-2 vectors are designed for constitutive expression of recombinant proteins from the baculovirus ie 1 promoter in stably-transformed insect cells (Cartier, J. L., et al., *J. Virol.* 68, 7728-7737)(1994). The plasmids differ only in the orientation of the multiple cloning sites and contain all promoter sequences known to be important for ie 1-mediated gene expression in uninfected insect cells as well as the hr5 enhancer element. pIE1-1 and pIE1-2 include the ie1 translation initiation site and can be used to produce fusion proteins.

The two solutions were combined and allowed to incubate at room temperature for 15 minutes. 8 ml of Ex-Cell media was added to the 2 ml of DNA/CellFectin mix and is layered on High-5 cells previously washed with Ex-Cell media. The plate was incubated in darkness for 1 hour at room temperature. The DNA/CellFectin mix was aspirated, and the cells washed once with Ex-Cell to remove excess Cellfectin. Fresh Ex-cell medium (30 ml) was added and the cells incubated for 3 days at 28° C. The supernatent was harvested and the expression of PRO301, PRO362 or PRO245 was determined by batch binding in a manner simliar to that described for Sf9 cells.

Example 17

Preparation of Antibodies that Bind PRO301, PRO362 and PRO245

This example illustrates preparation of monoclonal antibodies which can specifically bind PRO301, PRO362 and PRO245.

Techniques for producing the monoclonal antibodies are known in the art and are described, for instance, in Goding, supra. Immunogens that may be employed include purified PRO301, PRO362 and PRO245, fusion proteins containing PRO301, PRO362 and PRO245, and cells expressing recombinant PRO301, PRO362 and PRO245 on the cell surface. Selection of the immunogen can be made by the skilled artisan without undue experimentation.

Mice, such as Balb/c, are immunized with the PRO301, PRO362 and PRO245 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect PRO301, PRO362 and PRO245 antibodies.

After a suitable antibody titer has been detected, the animals "positive" for antibodies can be injected with a final intravenous injection of PRO301, PRO362 and PRO245. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO301, PRO362 and PRO245. Determination of "positive" hybridoma cells secreting the desired monoclonal antibodies against PRO301, PRO362 and PRO245 is within the skill in the art.

The positive hybridoma cells can be injected intraperitoneally into syngeneic Balb/c mice to produce ascites containing the anti-PRO301, anti-PRO362 or anti-PRO245 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Deposit of Material

The following materials have been deposited with the American Type Culture Collection, 10801 University Boulevard, Manassas, Va. 20110-2209, USA (ATCC):

| Designation | ATCC Dep. No. | Deposit Date |
|---|---|---|
| pRK5-based plasmid DNA40628-1216 | 209432 | Nov. 7, 1997 |
| DNA45416-1251 | 209620 | Feb. 5, 1998 |
| DNA35638-1141 | 209265 | Sep. 16, 1997 |

These deposits were made under the provisions of the Budapest Treaty on the International Recognition of the Deposit of Microorganisms for the Purpose of Patent Procedure and the Regulations there under (Budapest Treaty). This assures maintenance of a viable culture of the deposit for 30 years from the date of deposit and for at least five (5) years after the most recent request for the furnishing of a sample of the deposit received by the depository. The deposits will be made available by ATCC under the terms of the Budapest Treaty, and subject to an agreement between Genentech, Inc. and ATCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated nucleic acid molecule comprising:
   (a) a nucleotide sequence encoding the polypeptide of SEQ ID NO:9,
   (b) a nucleotide sequence encoding the polypeptide of SEQ ID NO:9 lacking its associated signal sequence,
   (c) the nucleotide sequence of SEQ ID NO:8,
   (d) the full-length coding sequence of the nucleic acid sequence of SEQ ID NO:8, or
   (e) the full-length coding sequence of the cDNA deposited under ATCC accession number 209265.

2. A vector comprising the nucleic acid molecule of claim 1.

3. An isolated host cell comprising the vector of claim 2.

4. The host cell of claim 3 which is a CHO cell, an *E. Coli*, a yeast cell or a Baculovirus-infected insect cell.

5. A process for producing a polypeptide of SEQ ID NO:9 comprising culturing the host cell of claim 3 under conditions suitable for expression of said polypeptide and recovering said polypeptide from the cell culture.

* * * * *